United States Patent
Crockett et al.

(10) Patent No.: US 12,390,812 B2
(45) Date of Patent: Aug. 19, 2025

(54) APPARATUS AND METHODS FOR MOLECULAR DIAGNOSTICS

(71) Applicant: NUCLEIN, LLC, Austin, TX (US)

(72) Inventors: Richard Crockett, Austin, TX (US); Alan Blake, Austin, TX (US); Michael Karberg, Austin, TX (US); John Lupher, Austin, TX (US); Chris Clever Nee, Austin, TX (US); Matthew Flint Kepler, Austin, TX (US)

(73) Assignee: NUCLEIN, LLC, Austin, TX (US)

( * ) Notice: Subject to any disclaimer, the term of this patent is extended or adjusted under 35 U.S.C. 154(b) by 910 days.

(21) Appl. No.: 17/309,709

(22) PCT Filed: Dec. 19, 2019

(86) PCT No.: PCT/US2019/067537
§ 371 (c)(1),
(2) Date: Jun. 16, 2021

(87) PCT Pub. No.: WO2020/132279
PCT Pub. Date: Jun. 25, 2020

(65) Prior Publication Data
US 2022/0080427 A1    Mar. 17, 2022

Related U.S. Application Data

(60) Provisional application No. 62/781,735, filed on Dec. 19, 2018.

(51) Int. Cl.
*B01L 7/00* (2006.01)
*B01L 3/00* (2006.01)
*C12Q 1/686* (2018.01)

(52) U.S. Cl.
CPC ......... *B01L 7/525* (2013.01); *B01L 3/502707* (2013.01); *B01L 3/502715* (2013.01);
(Continued)

(58) Field of Classification Search
CPC ............. B01L 2200/04; B01L 2200/16; B01L 2300/0627; B01L 2300/0832;
(Continued)

(56) References Cited

U.S. PATENT DOCUMENTS

| | | |
|---|---|---|
| 5,229,297 A | 7/1993 | Schnipelsky et al. |
| 5,786,182 A | 7/1998 | Catanzariti et al. |

(Continued)

FOREIGN PATENT DOCUMENTS

| | | |
|---|---|---|
| AU | 2015210344 | 8/2015 |
| CN | 103614290 A | 3/2014 |

(Continued)

OTHER PUBLICATIONS

Extended European Search Report issued in European Patent Application No. 21767713.7, dated Mar. 26, 2024.
(Continued)

*Primary Examiner* — Kathryn Elizabeth Limbaugh
(74) *Attorney, Agent, or Firm* — Parker Highlander PLLC

(57) ABSTRACT

This disclosure relates to apparatus and methods for molecular diagnostics. Certain embodiments include a piston cycled from a first position proximal to a first end of a housing, to a second position proximal to a second end of the housing, and back to the first position proximal to the first end of the housing. In some embodiments, the present disclosure relates to devices, methods, and systems for molecular diagnostics that do not comprise a piston.

15 Claims, 21 Drawing Sheets

(52) U.S. Cl.
CPC ......... *B01L 3/50273* (2013.01); *B01L 3/5029* (2013.01); *C12Q 1/686* (2013.01); *B01L 2200/04* (2013.01); *B01L 2200/16* (2013.01); *B01L 2300/0627* (2013.01); *B01L 2300/0832* (2013.01); *B01L 2300/1805* (2013.01); *B01L 2400/043* (2013.01); *B01L 2400/0478* (2013.01)

(58) Field of Classification Search
CPC ..... B01L 2300/1805; B01L 2400/0473; B01L 2400/0478; B01L 3/502715; B01L 3/50273; B01L 7/525; C12Q 1/686; C12Q 2561/113; G01N 1/38; G01N 2001/382; G01N 2035/00366; G01N 21/6428; G01N 35/00
See application file for complete search history.

(56) References Cited

U.S. PATENT DOCUMENTS

| | | | |
|---|---|---|---|
| 5,985,651 | A | 11/1999 | Hunicke-Smith |
| 6,001,611 | A | 12/1999 | Will |
| 6,126,904 | A | 10/2000 | Zuellig et al. |
| 6,132,996 | A | 10/2000 | Hunicke-Smith |
| 6,372,484 | B1 | 4/2002 | Ronchi et al. |
| 6,453,242 | B1 | 9/2002 | Eisenberg et al. |
| 6,482,590 | B1 | 11/2002 | Ullman et al. |
| 6,503,717 | B2 | 1/2003 | Case et al. |
| 6,534,261 | B1 | 3/2003 | Cox, III et al. |
| 6,537,256 | B2 | 3/2003 | Santini et al. |
| 6,551,838 | B2 | 4/2003 | Santini et al. |
| 6,599,692 | B1 | 7/2003 | Case et al. |
| 6,689,558 | B2 | 2/2004 | Case |
| 6,794,136 | B1 | 9/2004 | Eisenberg et al. |
| 7,030,215 | B2 | 4/2006 | Liu et al. |
| 7,067,317 | B2 | 6/2006 | Rebar et al. |
| 7,070,592 | B2 | 7/2006 | Santini et al. |
| 7,070,934 | B2 | 7/2006 | Cox, III et al. |
| 7,253,273 | B2 | 8/2007 | Collingwood |
| 7,262,054 | B2 | 8/2007 | Jamieson et al. |
| 7,361,635 | B2 | 4/2008 | Miller et al. |
| 7,524,652 | B2 | 4/2009 | Ammann et al. |
| 7,888,015 | B2 | 2/2011 | Toumazou et al. |
| 8,133,451 | B2 | 3/2012 | Yuan |
| 8,133,703 | B2 | 3/2012 | Ching et al. |
| 8,211,202 | B2 | 7/2012 | Hirai et al. |
| 8,232,091 | B2 | 7/2012 | Maltezos et al. |
| 8,394,608 | B2 | 3/2013 | Ririe et al. |
| 8,398,940 | B2 | 3/2013 | Silverbrook et al. |
| 8,640,555 | B2 | 2/2014 | Zenhausern et al. |
| 8,720,198 | B2 | 5/2014 | Wood |
| 8,795,965 | B2 | 8/2014 | Zhang |
| 8,883,088 | B2 | 11/2014 | Malik et al. |
| 8,894,946 | B2 | 11/2014 | Nielsen et al. |
| 9,044,755 | B2 | 6/2015 | Park et al. |
| 9,105,384 | B2 | 8/2015 | Fullerton et al. |
| 9,427,739 | B2 | 8/2016 | Suhl |
| 9,476,895 | B2 | 10/2016 | Self et al. |
| 9,519,000 | B2 | 12/2016 | Wilson et al. |
| 9,623,415 | B2 | 4/2017 | Andreyev et al. |
| 9,669,409 | B2 | 6/2017 | Dority et al. |
| 9,686,395 | B2 | 6/2017 | Erickson et al. |
| 9,719,134 | B2 | 8/2017 | Yoon et al. |
| 9,932,634 | B2 | 4/2018 | Wittwer et al. |
| 10,011,841 | B2 | 7/2018 | Cuero Rengifo et al. |
| 10,017,807 | B2 | 7/2018 | Srinivasan et al. |
| 10,040,071 | B2 | 8/2018 | Bird et al. |
| 10,052,629 | B2 | 8/2018 | Andreyev et al. |
| 10,058,868 | B2 | 8/2018 | Ririe et al. |
| 10,112,196 | B2 | 10/2018 | Andreyev et al. |
| 10,196,678 | B2 | 2/2019 | Pennathur et al. |
| 10,245,590 | B2 | 4/2019 | Kim et al. |
| 10,519,492 | B2 | 12/2019 | DeJohn et al. |
| 10,626,453 | B2 | 4/2020 | Huber et al. |
| 2002/0068357 | A1 | 6/2002 | Mathies et al. |
| 2003/0092172 | A1 | 5/2003 | Oh et al. |
| 2004/0014117 | A1 | 1/2004 | Slepnev |
| 2004/0053290 | A1 | 3/2004 | Terbrueggen et al. |
| 2004/0191830 | A1 | 9/2004 | Hwang et al. |
| 2005/0013732 | A1 | 1/2005 | Battrell et al. |
| 2005/0064474 | A1 | 3/2005 | Urnov et al. |
| 2005/0267061 | A1 | 12/2005 | Martin |
| 2006/0188987 | A1 | 8/2006 | Gushin et al. |
| 2007/0128621 | A1 | 6/2007 | Lao et al. |
| 2007/0218528 | A1 | 9/2007 | Miller et al. |
| 2010/0137152 | A1 | 6/2010 | Gorfinkel et al. |
| 2010/0291536 | A1 | 11/2010 | Viljoen et al. |
| 2011/0059502 | A1 | 3/2011 | Chalsani et al. |
| 2011/0312071 | A1 | 12/2011 | Silberbrook et al. |
| 2011/0312072 | A1 | 12/2011 | Azimi et al. |
| 2011/0318728 | A1 | 12/2011 | Phan et al. |
| 2013/0203634 | A1 | 8/2013 | Jovanovich et al. |
| 2013/0272087 | A1 | 10/2013 | Carrera Fabra et al. |
| 2015/0079598 | A1 | 3/2015 | Yasuda et al. |
| 2015/0136602 | A1 | 5/2015 | Jovanovich et al. |
| 2015/0273472 | A1 | 10/2015 | Murayama |
| 2016/0016171 | A1 | 1/2016 | Goel |
| 2016/0263579 | A1 | 9/2016 | Corbett et al. |
| 2017/0074258 | A1 | 3/2017 | Amirouche et al. |
| 2017/0173588 | A1 | 6/2017 | Tang et al. |
| 2017/0203297 | A1 | 7/2017 | Andreyev et al. |
| 2017/0218431 | A1 | 8/2017 | Breidenthal et al. |
| 2017/0232441 | A1 | 8/2017 | Nazzareth et al. |
| 2017/0247745 | A1 | 8/2017 | Shultz et al. |
| 2017/0304829 | A1 | 10/2017 | Andreyev et al. |
| 2018/0154364 | A1 | 6/2018 | Handique et al. |
| 2018/0193834 | A1 | 7/2018 | Mauk et al. |
| 2018/0280975 | A1 | 10/2018 | Kilcoin et al. |
| 2019/0168219 | A1 | 6/2019 | Caplin et al. |
| 2019/0169677 | A1 | 6/2019 | Andreyev et al. |
| 2019/0232293 | A1 | 8/2019 | Tang et al. |
| 2019/0299207 | A1 | 10/2019 | Lee et al. |
| 2020/0047184 | A1 | 2/2020 | Beer et al. |
| 2020/0157607 | A1 | 5/2020 | Nagai et al. |

FOREIGN PATENT DOCUMENTS

| | | |
|---|---|---|
| CN | 103 614 290 B | 3/2015 |
| CN | 107653300 | 2/2018 |
| CN | 110004024 | 7/2019 |
| CN | 110358681 | 10/2019 |
| CN | 107405621 B | 11/2019 |
| CN | 210176845 | 3/2020 |
| JP | 2011-508589 A | 4/2005 |
| JP | 2005-509424 A | 3/2011 |
| JP | 2018-505660 A | 3/2018 |
| KR | 102046943 | 11/2019 |
| KR | 102050161 | 11/2019 |
| KR | 102113957 | 5/2020 |
| MX | 2017013215 | 4/2019 |
| WO | WO 2009/108501 | 9/2009 |
| WO | WO 2013/123035 | 8/2013 |
| WO | WO 2014/113663 | 7/2014 |
| WO | WO 2016/035817 A1 | 3/2016 |
| WO | WO 2018/005710 | 1/2018 |
| WO | WO 2018/005870 | 1/2018 |
| WO | WO 2018/111782 | 6/2018 |
| WO | WO 2019/155488 | 8/2019 |
| WO | WO 2020/068910 | 4/2020 |
| WO | WO 2020/132279 | 6/2020 |
| WO | WO 2021/198476 A1 | 10/2021 |

OTHER PUBLICATIONS

Chien et al., "A micro circulating PCR chip using a suction-type membrane for fluidic transport," *Biomed. Microdevices*, 11(2):359-67, 2009. (Abstract).

Cho et al., "Nanophotonic Cell Lysis and Polymerase Chain Reaction with Gravity-Driven Cell Enrichment for Rapid Detection of Pathogens," *ACS Nano*, 13(12):13866-138974, 2019.

(56) References Cited

OTHER PUBLICATIONS

Choi et al., "Sample-to-answer palm-sized nucleic acid testing device towards low-cost malaria mass screening," *Biosensors and Bioelectronics*, 115:83-90, 2018.

Jie et al., "Portable and Battery-Powered PCR Device for DNA Amplification and Fluorescence Detection," Sensors (Basel), 20(9):2627, 14 pages, 2020.

Kimura et al., "3D microdevices that perform sample purification and multiplex qRT-PCR for early cancer detection with confirmation of specific RNAs," *Sci. Rep.*, 8(17480), 10 pages, 2018.

Legendre et al., "A Simple, Valveless Microfluidic Sample Preparation Device for Extraction and Amplification of DNA from Nanoliter-Volume Samples," *Anal. Chem.*, 78(5):1444-51, 2006.

Lim et al., "Battery-operated portable PCR system with enhanced stability of Pt RTD," *PLoS One*, 14(6): e0218571, 2019.

Liu et al., "Self-Contained, Fully Integrated Biochip for Sample Preparation, Polymerase Chain Reaction Amplification, and DNA Microarray Detection," Anal. Chem., 76:1824-1831, 2004.

Niemz et al., "Point-of-care nucleic acid testing for infectious diseases," *Trends Biotechnol.*, 29(5):24-250, 2011.

Ouyang et al., "One-Step Nucleic Acid Purification and Noise-Resistant Polymerase Chain Reaction by Electrokinetic Concentration for Ultralow-Abundance Nucleic Acid Detection," *Angew. Chem. Int. Ed. Engl.*, 59(27):10981-10988, 2020.

PCT International Search Report and Written Opinion issued in International Application No. PCT/US2019/067537, dated May 5, 2020.

Sciuto et al., "An integrated biosensor platform for extraction and detection of nucleic acids," *Biotechnology and Bioengineering*, 117(5):1554-1561, 2020.

Yang et al., "A sample-in-digital-answer-out system for rapid detection and quantitation of infectious pathogens in bodily fluids," *Analytical and Bioanalytical Chemistry*, 410:7019-7030, 2018.

Yin et al., "A fast nucleic acid extraction system for point-of-care and integration of digital PCR," *Analyst*, 144:7032-7040, 2019.

Zhu et al., "A Lab-on-a-Chip Device Integrated DNA Extraction and Solid Phase PCR Array for the Genotyping of High-Risk HPV in Clinical Samples," *Micromachines (Basel)*, 10(8):537, 12 pages, 2019.

Zhu et al., "A Novel Microfluidic Device Integrated with Chitosan-Modified Capillaries for Rapid ZIKV Detection," *Micromachines (Basel)*, 11(2):186, 17 pages, 2020.

Supplemental Search Report issued in European Application No. 19900283.3, dated Sep. 9, 2022.

Mokany, et al., "MNAzymes, a Versatile New Class of Nucleic Acid Enzymes that can Function as Biosensors and Molecular Switches", *J. Am. Chem. Soc.*, 132(3):1051-1059, 2010.

Extended European Search Report issued in European Application No. 19900283.3, dated Jan. 25, 2023.

Office Action issued in Indian Application No. 202127031881, dated Feb. 8, 2023.

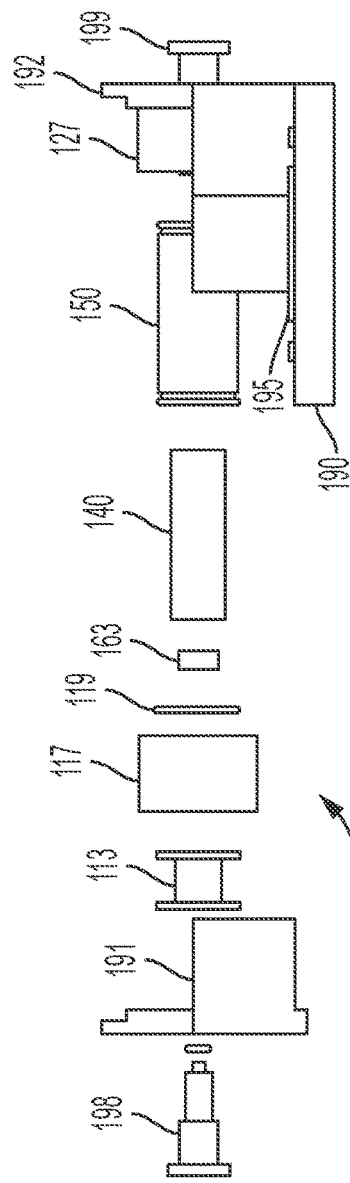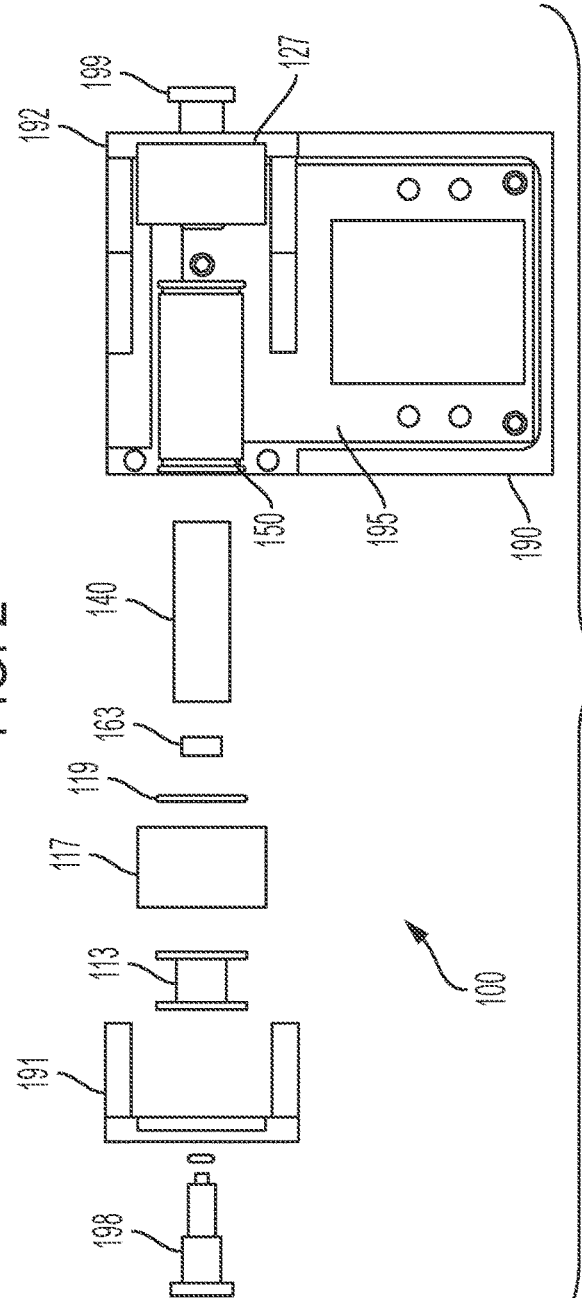

APPARATUS AND METHODS FOR MOLECULAR DIAGNOSTICS

CROSS-REFERENCE TO RELATED APPLICATIONS

This application is a national phase application under 35 U.S.C. § 371 of International Application No. PCT/US2019/067537, filed Dec. 19, 2019, which claims priority to U.S. Provisional Patent Application Ser. No. 62/781,735 filed Dec. 19, 2018, the entire contents of each of which are incorporated by reference herein.

BACKGROUND

A. Field

This disclosure relates to apparatus and methods for molecular diagnostics. More particularly, this disclosure relates to performing molecular diagnostics via a portable device that can provide point-of-care diagnostics.

B. Related Art

Molecular diagnostics can provide many benefits including early detection of diseases, disorders, or other genetic health-related conditions. Many molecular diagnostic techniques are based on the detection and identification of specific nucleic acids, both deoxyribonucleic acid (DNA) and ribonucleic acid (RNA), extracted and amplified from a biological specimen (e.g. blood, saliva or other substances as disclosed herein). Accordingly, while molecular diagnostics provide many benefits, typical molecular diagnostic devices are complicated, expensive, non-portable and require additional equipment and technical expertise for sample preparation, analysis, etc.

Despite barriers associated with typical devices, molecular diagnostic tests have the potential to improve health care services, enhance patient outcomes and individualized patient care. In view of the above, there is a need for molecular diagnostics provided by a stand-alone, inexpensive, simple-to-use, portable device suitable for point-of-care use.

SUMMARY

Briefly, the present disclosure provides devices, methods, and systems for molecular diagnostics comprising a piston that moves between two or more positions to cycle a fluid between two or more temperatures. In some embodiments, the present disclosure provides devices, methods, and systems for molecular diagnostics that do not comprise a piston.

Certain embodiments comprise an apparatus for performing molecular diagnostics, where the apparatus comprises: a housing comprising a first end and a second end; a piston disposed within the housing; a first heat source disposed proximal to the first end of the housing; and an actuator configured to move the piston in a cycle between a first position and a second position proximal to the second end of the housing, and back to the first position proximal to the first end of the housing. In some embodiments, the actuator may, after cycling the piston multiple times between the first and second positions, stop the piston at either the first position or the second position when the cycling process is completed. In particular embodiments, at least a portion of the fluid moves in an opposite direction to the piston during the cycle. In certain embodiments the detection module detects a response from the analyte in real time during amplification. In particular embodiments the detection module detects a response from the analyte within an amplification cycle. In some embodiments the amplification cycle has a variable length.

Some embodiments further comprise a second heat source proximal to the second end of the housing. In specific embodiments, the first heat source comprises a first heating coil configured to increase the temperature of the first end of the housing when electric current is applied to the first heating coil; and the second heat source comprises a second heating coil configured to increase the temperature of the second end of the housing when electric current is applied to the second heating coil. Certain embodiments further comprise a reaction chamber insert or cartridge configured to be inserted into the housing. In particular embodiments, the reaction chamber insert contains a reaction fluid during use. In some embodiments, the reaction fluid does not contact the piston and the housing during use (for example, when a liner, insert, or other intermediary material is used). In specific embodiments, the housing comprises a fluid configured to replicate (i.e., amplify) a nucleic acid sequence or sequences via thermal cycling. In certain embodiments, the nucleic acid is DNA or RNA or XNA.

In particular embodiments, the piston is configured to direct at least a portion of the fluid to the second end of the housing when the piston is in the first position; and the piston is configured to direct at least a portion of the fluid to the first end of the housing when the piston is in the second position. In some embodiments, the fluid comprises reagents for amplification or replication (e.g., via qualitative, quantitative, or semi-quantitative PCR, RT-PCR or other thermal cycling or isothermal techniques). In some embodiments, the fluid comprises polymerase chain reaction (PCR) reagents, such as reagents for reverse transcriptase polymerase chain reaction (RT-PCR), multiplex PCR, nested PCR, asymmetric PCR, hot-start PCR, methylation-specific PCR, allele-specific PCR, assembly PCR, convective PCR, dial-out PCR, digital PCR, helicase-dependent amplification, in silico PCR, intersequence-specific PCR, inverse PCR, ligation-mediated PCR, miniprimer PCR, multiplex ligation-dependent probe amplification, nanoparticle-assisted PCR, overlap-extension PCR, PAN-AC, RNA H-dependent PCR, single specific primer PCR, solid phase PCR, suicide PCR, thermal asymmetric interlaced PCR, isothermal PCR, touchdown PCR, universal fast walking PCR, extreme PCR, photonic PCR, cold PCR, or heat pulse extension PCR. Specific embodiments further comprise an illumination module configured to illuminate one or more analytes contained in the fluid. Certain embodiments further comprise a detection module configured to detect a response from the one or more analytes contained in the fluid. Particular embodiments further comprise a controller configured to control the actuator, and the first heat source. Particular other embodiments further comprise the controller configured to control more than one heat source.

In some embodiments the controller is configured to: control the first heat source to heat the fluid proximal to the first end of the housing to a temperature between about 85 and 100 degrees Celsius, such as between 85 and 90 degrees Celsius, or between 90 and 99 degrees Celsius; and control the second heat source to heat the fluid proximal to the second end of the housing to a temperature between about 50 and 75 degrees Celsius, such as between about 55 and 70 degrees; and cycle the piston from the first position to the second position and back to the first position between about 20 and 60 cycles, such as between about 25 and 55 cycles.

In some embodiments the controller is configured to: control the first heat source to heat the fluid proximal to the first end of the housing to a temperature between about 92 and 98 degrees Celsius; and control the second heat source to heat the fluid proximal to the second end of the housing to a temperature between about 60 and 65 degrees Celsius; and cycle the piston from the first position to the second position and back to the first position between about 30 and 50 cycles. In some embodiments the controller is configured to: control the first heat source to heat the fluid proximal to the first end of the housing to a temperature of about 92° C., 93° C., 94° C., 95° C., 96° C., 97°, or 98° C.; and control the second heat source to heat the fluid proximal to the second end of the housing to a temperature about 60° C., 61° C., 62° C., 63° C., 64° C., or 65° C.; and cycle the piston from the first position to the second position and back to the first position between about 30 and 35 cycles, between 35 and 40 cycles, between 40 and 45 cycles, or between 45 and 50 cycles. In specific embodiments, the actuator comprises: at least one coil; and a magnetic element disposed within the piston, wherein the at least one coil is configured to exert a force on the magnetic element when electric current is applied to the at least one coil.

In some embodiments, the controller is configured to control the first heat source to heat the fluid proximal to the first end of the housing to an initial temperature of between 90° C. to 99° for one or more cycle(s), and subsequently to the aforementioned one or more cycle(s) to an average temperature between about 78° C. and 98° C. and control the second heat source to heat at least a portion of the fluid proximal to the second end of the housing to an average temperature between about 34° C. and 75° C. and cycle the piston between the first and second positions at least 5-10 cycles. In some embodiments, the piston is cycled between the first and second positions at least 3 cycles, such as 4, 5, 6, 7, 8, 9, 10, 11, 12, 13, 14, 15, or more cycles. In some embodiments, the controller is configured to control the first heat source to heat the fluid proximal to the first end of the housing to an initial temperature of between 90° C. to 99° C. (e.g., 90° C., 91° C., 92° C., 93° C., 94° C., 95° C., 96° C., 97° C., 98° C., or 99° C.) for one or more cycle(s), and subsequently to the aforementioned one or more cycle(s) to an average temperature between about 78° C. and 98° C. (e.g., between about 78° C. and 80° C., between about 80° C. and 85° C., between about 85° C. and 90° C., between about 90° C. and 95° C., or between about 95° C. and 98° C.) and control the second heat source to heat at least a portion of the fluid proximal to the second end of the housing to an average temperature between about 34° C. and 75° C. (e.g., between about 34° C. and 40° C., between about 40° C. and 45° C., between about 45° C. and 50° C., between about 50° C., and 55° C., between about 55° C. and 60° C., between about 60° C. and 65° C., between 65° C. and 70° C., or between about 70° C. and 75° C.) and cycle the piston between the first and second positions at least 5-10 cycles. In some embodiments, piston is cycled between the first and second positions at least 3 cycles, such as 4, 5, 6, 7, 8, 9, 10, 11, 12, 13, 14, 15, or more cycles. In some embodiments, the temperature range can be optimized based on the histone acetylation or methylation of the target nucleic acid. In other embodiments, the temperature range can be optimized based on the base-pairing dynamics, for example the GC content or differential sequencing of base-pairs (Lorenz, Polymerase Chain Reaction: Basic Protocol Plus Troubleshooting and Optimization Strategies, J Vis Exp. 2012; (63): 3998; Roux, Optimization and troubleshooting in PCR, Cold Spring Harb Protoc. 2009; Robertson J. M., Walsh-Weller J. (1998) An Introduction to PCR Primer Design and Optimization of Amplification Reactions. In: Lincoln P. J., Thomson J. (eds) Forensic DNA Profiling Protocols. Methods in Molecular Biology, vol 98. Humana Press, each incorporated herein by reference).

In certain embodiments, the actuator comprises: a first coil proximal to the first end of the housing; a second coil proximal to the second end of the housing; and a first magnetic element disposed within the housing; and a second magnetic element disposed within the housing wherein: the first coil is configured to exert a first force on the first magnetic element when electric current is applied to the first coil; and the second coil is configured to exert a second force on the second magnetic element when electric current is applied to the second coil. In some embodiments, the second magnetic element is not present and the first and second coils can be configured to exert a first and second force on the first magnetic element, which may be disposed within or coupled to a piston. In other embodiments, the second magnetic coil is not present and the first magnetic coil can exert a first force on the first magnetic element, which may be disposed within or coupled to a piston or, alternatively, the first and second magnetic elements, for example through reversing the polarity of an H-bridge or similar electromagnetic element. In other embodiments, the force exerted from the coil or coils may act upon elements within the housing, which are formed from more than two portions, for example if the piston comprises multiple sections or granules. In particular embodiments, the first coil is configured to increase the temperature of the first end of the housing when electric current is applied to the first coil; and the second coil is configured to increase the temperature of the second end of the housing when electric current is applied to the second coil. In certain embodiments, the temperature can be modified (for example, decreased) by reducing or discontinuing current. Some embodiments further comprise an input port in fluid communication with the housing. In specific embodiments, the input port comprises a collection piston, rod assembly or plunger configured to advance a sample. In certain embodiments, the housing comprises lyophilized pellets. In other embodiments, a pressure difference such as partial or complete vacuum is employed to advance a sample, sometimes in concert with the plunge. In other embodiments, the apparatus contains a valve or aspect which allows residual air to escape the chamber. In some aspects, the rod assembly or plunger rotates, follows a screw path, or is actuated by a camshaft or other component of mechanical linkage to convert rotating motion into a sliding or linear path. In some embodiments, the actuator comprises one or more elements such as a piezoelectric, Stirling engine, memory wire, actuator wire, or thin wire made from Nitinol, nickel-titanium alloy (e.g. Muscle Wire) and is configured to exert a first force on the element when electric current is applied to the element, or when temperature gradients are applied against it.

In particular embodiments, the piston has an outer diameter; the housing or chamber has an inner diameter; and the ratio of the outer diameter of the piston to the inner diameter of the housing is between 0.90 and 0.999. In some embodiments, the ratio of the outer diameter of the piston to the inner diameter of the housing is between 0.90 and 0.91, between 0.91 and 0.92, between 0.93 and 0.94, between 0.94 and 0.95, between 0.95 and 0.96, between 0.96 and 0.97, between 0.97 and 0.98, or between 0.98 and 0.999. In some embodiments, the piston comprises a channel that may permit the passage of fluid. In specific embodiments, the channel is a central capillary channel, the channel having a diameter than can be 0.3 mm to 2 mm. In some embodiments, the channel has a diameter of less than about 0.2 mm, or about 0.2 mm, 0.3 mm, 0.4 mm, 0.5 mm, 0.6 mm, 0.7 mm, 0.8 mm, 0.9 mm, 1.0 mm, 1.1 mm, 1.2 mm, 1.3 mm, 1.4 mm, 1.5 mm, 1.6 mm, 1.7 mm, 1.8 mm, 1.9 mm, 2 mm or greater. In certain embodiments, the channel is a central capillary channel, the channel having a diameter of 1 mm, but optionally to a diameter that is bounded on the lower end by the minimal practical diameter achievable through high-volume injection molding, e.g. 0.2 mm. In some embodiments, the diameters of the piston are tolerant of low precisions, such that mass-production injection molding techniques may be used. Specifically, some embodiments the tolerance of the inner diameter of the housing is plus or minus 1, 2, 3, 4, 5, 6, 7, 8, 9, 10, 15, 20 mils or more. In some embodiments, the tolerance of the outer diameter of the piston is plus or minus 1, 2, 3, 4, 5, 6, 7, 8, 9, 10, 15, 20 mils or more.

Particular embodiments include a method of thermally cycling a fluid for replicating (i.e., amplifying) a nucleic acid sequence or sequence(s), the method comprising: moving a piston disposed within a housing from a first end of the housing to a second end of the housing, wherein a fluid is disposed within the housing and wherein the fluid comprises components for replicating a nucleic acid; displacing at least a portion of the fluid within the housing from the second end of the housing to a first end of the housing; controlling a temperature of the fluid at a first average temperature range for a first period of time; moving the piston from the second end of the housing to a first end of the housing; displacing the fluid opposite to the location of the piston within the housing from the second end of the housing to a first end of the housing; and controlling the temperature of the fluid to a second average temperature range for a second period of time.

In certain embodiments of the method, the piston comprises a channel; and displacing the fluid within the housing from the second end of the housing to the first end of the housing comprises directing at least a portion of the fluid through the channel. In specific embodiments, the channel in the piston is a central channel. In some embodiments, moving the piston disposed within the housing (sometimes referred to herein as a chamber or cylinder) from the first end of the housing to the second end of the housing comprises applying current to a coil and exerting a force on a magnetic element disposed within the housing. In specific embodiments, the coil is a first coil proximal to the first end of the housing; the magnetic element is a first magnetic element disposed between the piston and the first end of the housing; and moving the piston disposed within the housing from the second end of the housing to the first end of the housing comprises applying current to a second coil near the second end of the housing and exerting a force on a second magnetic element disposed between the piston and the second end of the housing.

In certain embodiments of the method, controlling the temperature of the fluid at the first temperature range for the first period of time comprises applying current to a first heating coil proximal to the first end of the housing; and controlling the temperature of the fluid at the second temperature range for the second period of time comprises applying current to a second heating coil proximal to the second end of the housing. The first temperature range may be between about 90 degrees Celsius and 100 degrees Celsius (e.g., about 90° C., 91° C., 92° C., 93° C., 94° C., 95° C., 96° C., 97° C., 98° C., 99° C., or 100° C.) and the second temperature range is between about 50 and 75 degrees Celsius (e.g., about 50 to 55° C., between about 55 and 60° C., between about 60 and 65° C., between about 65 and 70° C., or between about 70 and 75° C.); the first time period is less than 2 seconds, or between about 2 and 10 seconds (e.g., 2, 3, 4, 5, 6, 7, 8, 9, or 10 seconds); and the second time period is less than 5 seconds, or between about 5 and 15 seconds (e.g., 5, 6, 7, 8, 9, 10, 11, 12, 13, 14, or 15 seconds). The first temperature range is between about 92 and 98 degrees Celsius and the second temperature range is between about 60 and 65 degrees Celsius; the first time period is less than 2 seconds, or less than 2 seconds, or less than 2 seconds, or between about 4 and 6 seconds (or in some embodiments, 6 to 10 seconds, 10 to 15 seconds, 15 to 20 seconds, 20 to 25 seconds, 25 to 30 seconds or more); and the second time period is between about 8 and 12 seconds (or in some embodiments, 4 to 8 seconds, 12 to 15 seconds, 15 to 20 seconds, 20 to 25 seconds, 25 to 30 seconds or more). In some embodiments, the piston is cycled from the first position to the second position and back to the first position between about 2 and 15 cycles, 20 and 60 cycles (e.g., between about 20 and 25 cycles, between about 25 and 30 cycles, between about 30 and 35 cycles, between about 35 and 40 cycles, between about 40 and 45 cycles, between about 45 and 50 cycles, between about 50 and 55 cycles, and between about 55 and 60 cycles). In particular embodiments of the method, the piston is cycled from the first position to the second position and back to the first position between about 30 and 50 cycles.

Specific embodiments include a method of analyzing a biological sample, the method comprising: placing the biological sample within the above-described (or otherwise herein-described) diagnostic apparatus; lysing the biological sample; introducing reagents to the biological sample; operating the diagnostic apparatus to thermally cycle the lysed biological sample, wherein the diagnostic apparatus comprises: a housing comprising a first end and a second end; a piston disposed within the housing; a first heat source proximal to a first end of the housing; a second heat source proximal to a second end of the housing; and an actuator configured to move the piston between a first position proximal to the first end of the housing to a second position proximal to the second end of the housing and back to the first position proximal to the first end of the housing. In certain embodiments, the reagents comprise reagents for replicating a nucleic acid in the biological sample.

In specific embodiments of the method, operating the diagnostic apparatus to thermally cycle the biological sample comprises: moving the piston disposed within the housing from a first end of the housing towards a second end of the housing; displacing at least a portion of the biological sample and the reagents opposite from the location of piston from the second end of the housing towards the first end of the housing; moving the piston disposed within the housing from the second end of the housing towards the first end of the housing; and displacing at least a portion of the biological sample and the reagents from the first end of the housing towards the second end of the housing; moving the piston disposed within the housing from a first end of the housing towards a second end of the housing; and displacing at least a portion of the biological sample and the reagents from the second end of the housing towards the first end of the housing, wherein: the first end of the housing is controlled to a temperature within a first average temperature range; and the second end of the housing is controlled to a temperature within a second average temperature range.

In certain embodiments of the method, the piston comprises a channel; displacing the fluid within the housing from the second end of the housing to the first end of the housing comprises directing at least a portion of the fluid through the channel in a first direction; and displacing at least a portion of the fluid within the housing from the first end of the housing to the second end of the housing comprises directing at least a portion of the fluid through the channel in a second direction different than the first direction. In particular embodiments, the channel in the piston is a central channel. In some embodiments, moving the piston disposed within the housing from the first end of the housing towards the second end of the housing comprises applying current to a coil and exerting a force on a magnetic element disposed within the housing.

In specific embodiments of the method, the coil is a first coil proximal to the first end of the housing; the magnetic element is a first magnetic element disposed within the piston and the first end of the housing or between the piston and first end of the housing; and moving the piston disposed within the housing from the second end of the housing towards the first end of the housing comprises applying current to a second coil proximal to the second end of the housing and exerting a force on a second magnetic element disposed within or between the piston and the second end of the housing. In certain embodiments, controlling the temperature of the first end of the housing comprises applying current to a first heating coil proximal to the first end of the housing; and controlling the temperature of the second end of the housing comprises applying current to a second heating coil proximal to the second end of the housing.

In particular embodiments of the method, the first temperature range is sufficient to heat the biological sample and the reagents to a first sample average temperature between about 90 degrees Celsius and 100 degrees Celsius (e.g., about 90° C., 91° C., 92° C., 93° C., 94° C., 95° C., 96° C., 97° C., 98° C., 99° C., or 100° C.); the second average temperature range is sufficient to heat the biological sample and the reagents to a second sample average temperature between about 34 and 75 degrees Celsius (e.g., about 34-40° C., about 40-45° C., about 50 to 55° C., between about 55 and 60° C., between about 60 and 65° C., between about 65 and 70° C., or between about 70 and 75° C.); at least a portion of the biological sample and the reagents are maintained near the first sample temperature for a time of about 2 and 10 seconds (e.g., 3, 4, 5, 6, 7, 8, 9, or 10 seconds); and the biological sample and the reagents are maintained at the second sample average temperature for a time of about 5 and 15 seconds (e.g., 5, 6, 7, 8, 9, 10, 11, 12, 13, 14, or 15 seconds). In some embodiments, the biological sample and the reagents are cycled from the first sample average temperature to the second sample average temperature and back to the first sample average temperature between about 20 and 60 cycles (e.g., between about 20 and 25 cycles, between about 25 and 30 cycles, between about 30 and 35 cycles, between about 35 and 40 cycles, between about 40 and 45 cycles, between about 45 and 50 cycles, between about 50 and 55 cycles, and between about 55 and 60 cycles).

In particular embodiments of the method, the first temperature range is sufficient to heat the biological sample and the reagents to a first sample average temperature between about 92 and 98 degrees Celsius; the second average temperature range is sufficient to heat the biological sample and the reagents to a second sample average temperature between about 60 and 65 degrees Celsius; at least a portion of the biological sample and the reagents are maintained at the first sample temperature for a time of about 4 and 6 seconds (or in some embodiments, 6 to 10 seconds, 10 to 15 seconds, 15 to 20 seconds, 20 to 25 seconds, 25 to 30 seconds or more); and the biological sample and the reagents are maintained at the second sample average temperature for a time of about 8 and 12 seconds (or in some embodiments, 4 to 8 seconds, 12 to 15 seconds, 15 to 20 seconds, 20 to 25 seconds, 25 to 30 seconds or more). In some embodiments, the biological sample and the reagents are cycled from the first sample average temperature to the second sample average temperature and back to the first sample average temperature between about 30 and 50 cycles.

Particular embodiments include a method of analyzing a biological sample, where the method comprises: placing the biological sample within a diagnostic apparatus; combining a defined volume of the biological sample to a defined volume of a fluid to produce a defined volume of biological sample fluid mixture; and operating the diagnostic apparatus to thermally cycle the biological sample fluid mixture, where the diagnostic apparatus comprises: a housing comprising a piston chamber; a piston disposed within the piston chamber; a first heat source proximal to the piston chamber; and an actuator configured to move the piston between a first position proximal to the first heat source and a second position distal to the first heat source.

In some embodiments the housing comprises a first end a second end; the first position of the piston is proximal to the first end of the housing; and the second position of the piston is proximal to the second end of the housing. In specific embodiments the volume of the biological sample placed within the diagnostic apparatus is not measured prior to placing the biological sample within the diagnostic apparatus. In certain embodiments the fluid comprises polymerase chain reaction (PCR) reagents or reverse transcriptase polymerase chain reaction (RT-PCR) reagents. In particular embodiments the fluid comprises a lysing agent and/or a diluting agent. In some embodiments the defined volume of the biological sample is introduced to the defined volume of the fluid via a pressure differential. In specific embodiments the defined volume of the fluid is at a higher pressure than the defined volume of the biological sample.

In certain embodiments the defined volume of the fluid is at a lower pressure than the defined volume of the biological sample. In particular embodiments the defined volume of the fluid is introduced to the defined volume of the biological sample via manual power provided by a user. In some embodiments the defined volume of the fluid is introduced to the defined volume of fluid without electrical power. In specific embodiments the defined volume of the biological sample is introduced to the defined volume of fluid without electrical power. In certain the defined volume of biological sample is introduced to the defined volume of fluid via rotation of a threaded component. In particular embodiments the diagnostic apparatus comprises a collection chamber; and placing the biological sample within the diagnostic apparatus comprises expectorating in the collection chamber. In some embodiments the diagnostic apparatus comprises a collection chamber; and placing the biological sample within the diagnostic apparatus comprises placing a swab in the collection chamber. In specific embodiments the swab contains a dilution liquid.

Certain embodiments include an apparatus comprising: a housing comprising a piston chamber; a piston located in the piston chamber; a first heat source proximal to the piston chamber; an actuator configured to move the piston between a first position proximal to the first heat source and a second position distal to the first heat source; and a rod assembly coupled to the housing, where: the rod assembly comprises a sample chamber and a fluid chamber; the sample chamber is in fluid communication with the piston chamber when the rod assembly is in a first position; the fluid chamber is in fluid communication with the piston chamber when the rod assembly is in a second position; and the sample chamber and the fluid chamber are not in fluid communication with the piston chamber when the rod assembly is in a third position. In particular embodiments the housing comprises a first end a second end; the first position of the piston is proximal to the first end of the housing; and the second position of the piston is proximal to the second end of the housing. In some embodiments the piston chamber is under vacuum. Specific embodiments further comprise a collection chamber configured to collect a biological sample. Certain embodiments further comprise a sensor configured to detect a biological sample in the collection chamber. In particular embodiments the sensor is an optical sensor. In some embodiments the sensor detects a change in electrical conductivity. In specific embodiments the apparatus automatically moves the rod assembly when the sensor detects a biological sample in the collection chamber. In certain embodiments the rod assembly is threadably coupled to the housing. In particular embodiments the rod assembly can be moved from the first position, to the second position and the third position by rotating at least a portion of the rod assembly.

Specific embodiments include an apparatus comprising: a chamber comprising a fluid configured to amplify a nucleic acid via thermal cycling; a light source configured to illuminate an analyte contained in the fluid; and a light detector, wherein the maximum distance between light source and the chamber is less than or equal to 2.0 centimeters. In some embodiments the maximum distance between the light source and the chamber is less than or equal to 1.0 centimeters, or more particularly less than or equal to 0.5 centimeters. In particular embodiments, the analyte is bound to a surface of the chamber. In some embodiments, the apparatus comprises a light path from the light source to the chamber, and the light path is less than or equal to 2.0 centimeters. In specific embodiments, the light path is less than or equal to 1.0 centimeters, or more particularly less than or equal to 0.5 centimeters.

In certain embodiments the light detector has an optical efficiency between 0.0025 percent and 0.025 percent, or more particularly between 0.005 percent and 0.0125 percent. In some embodiments the light source is configured to illuminate the fluid without a collimating lens. In particular embodiments, the light detector is configured to detect light without a collimating lens. In specific embodiments, the apparatus does not comprise a collimating lens. In specific embodiments the light source is configured to illuminate the fluid without a dichroic mirror. In certain embodiments the light source is configured to illuminate the fluid without a mirror. In some embodiments the light detector is configured to detect a signal light from an analyte contained in the fluid; the light detector is configured to detect background light when the signal light is not present; and the ratio of the signal light to the background light is at least 1.5:1. In specific embodiments the ratio of the signal light to the background light is at least 2:1, or at least 5:1, or at least 100:1 or at least 1000:1. In certain embodiments the light detector is configured to produce a current in response to light detected by the light detector.

In particular embodiments the current produced by the light detector comprises signal current in response to the signal light; the current produced by the light detector comprises dark current in response to the background light; and the ratio of signal current to background current is at least 1.5:1. In some embodiments the ratio of signal current to background current is at least 2:1, or at least 5:1, or at least 100:1. In specific embodiments the nucleic acid is deoxyribonucleic acid (DNA), and in particular embodiments the DNA is bacterial DNA and/or pathogenic DNA. In certain embodiments the nucleic acid is ribonucleic acid (RNA). In particular embodiments, fluid comprises polymerase chain reaction (PCR) reagents or reverse transcriptase polymerase chain reaction (RT-PCR) reagents. Some embodiments further comprise a piston disposed within the chamber. In specific embodiments: the chamber comprises a first end and a second end; the apparatus comprises an actuator configured to move the piston in a cycle from a first position near the first end of the chamber, to a second position near the second end of the chamber, and back to the first position near the first end of the chamber; the piston is configured to direct the fluid to the second end of the chamber when the piston is in the first position; and the piston is configured to direct the fluid to the first end of the chamber when the piston is in the second position.

In certain embodiments the piston is configured to direct the fluid to the second end of the chamber when the piston is in the first position; and the piston is configured to direct the fluid to the first end of the chamber when the piston is in the second position.

Particular embodiments include an apparatus comprising: a chamber comprising a fluid configured to amplify a nucleic acid via thermal cycling; a light source configured to illuminate an analyte contained in the fluid; and a light detector, wherein the light detector has an optical efficiency between 0.0025 percent and 0.025 percent. In some embodiments the detector has an optical efficiency between 0.005 percent and 0.0125 percent. In specific embodiments the maximum distance between light source and the chamber is less than or equal to 2.0 centimeters; and the light source is configured to illuminate the fluid without a collimating lens a collimating lens. In certain embodiments the maximum distance between the light source and the chamber is less than or equal to 1.0 centimeters, or more particularly less than or equal to 0.5 centimeters. In particular embodiments the light source is configured to illuminate the fluid without a collimating lens a dichroic mirror.

In some embodiments: the light detector is configured to detect a signal light from the analyte contained in the fluid; the light detector is configured to detect background light when the signal light is not present; and the ratio of the signal light to the background light is at least 1.5:1, or at least 2:1, or at least 5:1, or at least 100:1, or at least 1000:1. In specific embodiments the light detector is configured to produce a current in response to light detected by the light detector. In certain embodiments the current produced by the light detector comprises signal current in response to the signal light; the current produced by the light detector comprises dark current in response to the background light; and the ratio of signal current to background current is at least 1.5:1, or at least 2:1, or at least 5:1, or at least 100:1. In particular embodiments the nucleic acid is deoxyribonucleic acid (DNA), and in particular embodiments the DNA is bacterial DNA and/or pathogenic DNA. In some embodiments the nucleic acid is ribonucleic acid (RNA).

In specific embodiments the fluid comprises polymerase chain reaction (PCR) reagents or reverse transcriptase polymerase chain reaction (RT-PCR) reagents. Certain embodiments further comprise a piston disposed within the chamber. In particular embodiments the chamber comprises a first end and a second end; the apparatus comprises an actuator configured to move the piston in a cycle from a first position near the first end of the chamber, to a second position near the second end of the chamber, and back to the first position near the first end of the chamber; the piston is configured to direct the fluid to the second end of the chamber when the piston is in the first position; and the piston is configured to direct the fluid to the first end of the chamber when the piston is in the second position.

Specific embodiments include an apparatus comprising: a chamber comprising a fluid configured to amplify a nucleic acid via thermal cycling; a light source configured to illuminate an analyte contained in the fluid; and a light detector, where the maximum distance between light source and the chamber is less than or equal to 2.0 centimeters, where: the light detector is configured to detect a signal light from the analyte contained in the fluid; the light detector is configured to detect background light when the signal light is not present; the ratio of the signal light to the background light is at least 1.5:1; the light detector has an optical efficiency between 0.0025 percent and 0.025 percent; the light source is configured to illuminate the fluid without a collimating lens or a dichroic mirror; the chamber comprises a first end and a second end; the apparatus comprises an actuator configured to move the piston in a cycle from a first position near the first end of the chamber, to a second position near the second end of the chamber, and back to the first position near the first end of the chamber; the piston is configured to direct the fluid to the second end of the chamber when the piston is in the first position; and the piston is configured to direct the fluid to the first end of the chamber when the piston is in the second position.

Certain embodiments include an apparatus comprising: a chamber comprising a fluid configured to amplify a nucleic acid via thermal cycling; a light source configured to illuminate an analyte contained in the fluid; and a light detector, where: the light detector is configured to detect a signal light from the analyte contained in the fluid; the light detector is configured to detect background light when the signal light is not present; the ratio of the signal light to the background light is at least 1.5:1; the light detector has an optical efficiency between 0.0025 percent and 0.025 percent; the light source is configured to illuminate the fluid without a collimating lens or a dichroic mirror; the chamber comprises a first end and a second end; the apparatus comprises an actuator configured to move the piston in a cycle from a first position near the first end of the chamber, to a second position near the second end of the chamber, and back to the first position near the first end of the chamber; the piston is configured to direct the fluid to the second end of the chamber when the piston is in the first position; and the piston is configured to direct the fluid to the first end of the chamber when the piston is in the second position.

Particular embodiments include apparatus comprising: a chamber comprising a fluid configured to amplify a nucleic acid via thermal cycling; a light source configured to illuminate an analyte contained in the fluid; and a light detector, wherein the maximum distance between light source and the chamber is less than or equal to 2.0 centimeters, where: the light detector is configured to detect a signal light from the analyte contained in the fluid; the light detector is configured to detect background light when the signal light is not present; the ratio of the signal light to the background light is at least 1.5:1; the light source is configured to illuminate the fluid without a collimating lens or a dichroic mirror; the chamber comprises a first end and a second end; the apparatus comprises an actuator configured to move the piston in a cycle from a first position near the first end of the chamber, to a second position near the second end of the chamber, and back to the first position near the first end of the chamber; the piston is configured to direct the fluid to the second end of the chamber when the piston is in the first position; and the piston is configured to direct the fluid to the first end of the chamber when the piston is in the second position.

Specific embodiments include an apparatus comprising: a chamber comprising a fluid configured to amplify a nucleic acid via thermal cycling; a light source configured to illuminate an analyte contained in the fluid; and a light detector, where the maximum distance between light source and the chamber is less than or equal to 2.0 centimeters, where: the light detector is configured to detect a signal light from the analyte contained in the fluid; the light detector is configured to detect background light when the signal light is not present; the ratio of the signal light to the background light is at least 1.5:1; the light detector has an optical efficiency between 0.0025 percent and 0.025 percent; the chamber comprises a first end and a second end; the apparatus comprises an actuator configured to move the piston in a cycle from a first position near the first end of the chamber, to a second position near the second end of the chamber, and back to the first position near the first end of the chamber; the piston is configured to direct the fluid to the second end of the chamber when the piston is in the first position; and the piston is configured to direct the fluid to the first end of the chamber when the piston is in the second position.

Particular embodiments include an apparatus comprising: a chamber comprising a fluid configured to amplify a nucleic acid via thermal cycling; a light source configured to illuminate an analyte contained in the fluid; and a light detector, where the maximum distance between light source and the chamber is less than or equal to 2.0 centimeters, where: the light detector has an optical efficiency between 0.0025 percent and 0.025 percent; and the light source is configured to illuminate the fluid without a collimating lens or a dichroic mirror; the chamber comprises a first end and a second end; the apparatus comprises an actuator configured to move the piston in a cycle from a first position near the first end of the chamber, to a second position near the second end of the chamber, and back to the first position near the first end of the chamber; the piston is configured to direct the fluid to the second end of the chamber when the piston is in the first position; and the piston is configured to direct the fluid to the first end of the chamber when the piston is in the second position.

Specific embodiments include an apparatus comprising: a chamber comprising a fluid configured to amplify a nucleic acid via thermal cycling; a light source configured to illuminate an analyte contained in the fluid; and a light detector, wherein the maximum distance between light source and the chamber is less than or equal to 2.0 centimeters, wherein: the light detector is configured to detect a signal light from the analyte contained in the fluid; the light detector is configured to detect background light when the signal light is not present; the ratio of the signal light to the background light is at least 1.5:1; the light detector has an optical efficiency between 0.0025 percent and 0.025 percent; and the light source is configured to illuminate the fluid without a collimating lens or a dichroic mirror.

Certain embodiments include a sample collection device, where: the sample collection device is configured to accept a biological sample of variable volume and, in a single user-activated step, dilute the biological sample of variable volume in a fixed ratio into a fixed volume of diluted biological sample; and transfer the diluted biological sample into a pressure vessel configured for use in polymerase chain reaction (PCR).

Particular embodiments include an apparatus configured to perform polymerase chain reaction (PCR), where the apparatus comprises a piston. Certain embodiments include an apparatus configured to perform polymerase chain reaction (PCR), where the apparatus comprises a displacer piston. Some embodiments include an apparatus where the piston is in physical contact with at least one polymerase chain reaction (PCR) reagent. Particular embodiments include an apparatus which comprises a displacer piston in physical contact with at least one polymerase chain reaction (PCR) reagent. In specific embodiments, the apparatus is configured to accept a biological sample and in a single user-activated step, perform sample preparation, thermocycling polymerase chain reaction (PCR) amplification, and detection without the need for mechanical pumps or solenoids.

Certain embodiments include an optical system configured to detect a fluorescent signal from polymerase chain reaction (PCR), wherein the optical system has not undergone radiometric calibration prior to detecting the fluorescent signal. Particular embodiments an optical system configured to detect a fluorescent signal from polymerase chain reaction (PCR), where the optical system does not comprise dichroic mirrors. Some embodiments include an optical system configured to detect a fluorescent signal from polymerase chain reaction (PCR), wherein the optical system does not comprise collimating lenses. Specific embodiments include an optical system configured to detect a fluorescent signal from polymerase chain reaction (PCR), where the optical system has an optical efficiency of less than 0.3%.

Certain embodiments include an apparatus configured to perform semi-quantitative detection of a polymerase chain reaction (PCR) product without the use of floating-point mathematics functions. Particular embodiments include an apparatus configured to perform detection of a fluorescent signal from polymerase chain reaction (PCR), where: the apparatus performs a comparison to a relative fluorescence baseline; and the apparatus has not undergone radiometric calibration prior to detecting the fluorescent signal. Some embodiments include apparatus configured to detect nucleic acid in less than 5 minutes. Specific embodiments include an apparatus configured to detect nucleic acid in less than 10 minutes. Certain embodiments include an apparatus configured to detect nucleic acid in less than 15 minutes.

Particular embodiments include a method of detecting a nucleic acid sequence, where the method comprises: receiving into a PCR device a sample, wherein the PCR device uses either a non-radiometrically-calibrated optics or a piston; and determining, with the PCR device, whether the sample includes a nucleic acid sequence by: treating the sample with one or more marking agents useable to bind to the nucleic acid sequence; illuminating the sample with a light source, measuring fluorescence emitted by the marking agents, and determining, based on the measuring, whether the sample includes the nucleic acid sequence.

In some embodiments the nucleic acid sequence is associated with an infection disease. In specific embodiments the nucleic acid sequence is associated with a genetic defect. In certain embodiments the nucleic acid sequence is associated with a blood type. In particular embodiments the nucleic acid sequence is associated with target of a gene therapy treatment. In some embodiments the nucleic acid sequence is associated with concussions. In specific embodiments the sample was collected from an organism, and the nucleic acid sequence is associated with a population of the species of the organism, the method comprising: based on determining whether the sample includes the nucleic acid sequence, determining whether the organism is in the population.

In certain embodiments the organism is a non-human animal and the population is a particular breed of the non-human animal. In particular embodiments the sample is associated with a patient and wherein determining whether the sample includes the nucleic acid sequence includes analyzing biometric data gathered about the patient. In some embodiments the sample is associated with a criminal investigation. In specific embodiments the nucleic acid sequence is associated with a suspect of the criminal investigation. In certain embodiments the sample is associated with an unidentified person. In particular embodiments the sample is associated with a particular environment and wherein the nucleic acid sequence is associated with an invasive species to the particular environment. In some embodiments determining whether the sample includes a nucleic acid sequence is performed by the PCR device without communicating with remote devices. Specific embodiments further comprise communicating results of the determining to a remote device. In certain embodiments the PCR device includes less than 32 kilobytes (kB) of internal memory. In particular embodiments the PCR device includes less than 16 kilobytes (kB) of internal memory, or more particularly less than 8 kilobytes (kB) of internal memory. In some embodiments the PCR device does not receive power from an external source when determining whether the sample includes a nucleic acid sequence. In specific embodiments the sample and reagents are contained within a single-use cartridge.

Other objects, features and advantages of the present invention will become apparent from the following detailed description. It should be understood, however, that the detailed description and the specific examples, while indicating certain embodiments of the invention, are given by way of illustration only, since various changes and modifications within the spirit and scope of the invention will become apparent to those skilled in the art from this detailed description.

Unless defined otherwise herein, all technical and scientific terms used herein have the same meaning as commonly understood to one of ordinary skill in the art to which this invention belongs. Although any methods, devices and materials similar or equivalent to those described herein can be used in the practice or testing of the invention, the exemplified methods, devices and materials are now described.

Although the invention has been described with respect to specific embodiments thereof, these embodiments are merely illustrative, and not restrictive of the invention. The description herein of illustrated embodiments of the invention, including the description in the Abstract and Summary, is not intended to be exhaustive or to limit the invention to the precise forms disclosed herein (and in particular, the inclusion of any particular embodiment, feature or function within the Abstract or Summary is not intended to limit the scope of the invention to such embodiment, feature or function). Rather, the description is intended to describe illustrative embodiments, features and functions in order to provide a person of ordinary skill in the art context to understand the invention without limiting the invention to any particularly described embodiment, feature or function, including any such embodiment feature or function described in the Abstract or Summary. While specific embodiments of, and examples for, the invention are described herein for illustrative purposes only, various equivalent modifications are possible within the spirit and scope of the invention, as those skilled in the relevant art will recognize and appreciate. As indicated, these modifications may be made to the invention in light of the foregoing description of illustrated embodiments of the invention and are to be included within the spirit and scope of the invention. Thus, while the invention has been described herein with reference to particular embodiments thereof, a latitude of modification, various changes and substitutions are intended in the foregoing disclosures, and it will be appreciated that in some instances some features of embodiments of the invention will be employed without a corresponding use of other features without departing from the scope and spirit of the invention as set forth. In addition, the various features and embodiments of the invention contain aspects which may be used in combinations and permutations not described in particular embodiments described herein, but those skilled in the relevant art will recognize and appreciate that such combinations or permutations are within the spirit and scope of the invention. Therefore, many modifications may be made to adapt a particular situation or material to the essential scope and spirit of the invention. The disclosures of all patents, patent applications and publications cited herein are hereby incorporated herein by reference in their entireties, to the extent that they are consistent with the present disclosure set forth herein.

Reference throughout this specification to "one embodiment", "an embodiment", "some embodiments", "particular embodiment", or "a specific embodiment" or similar terminology means that a particular feature, structure, or characteristic described in connection with the embodiment is included in at least one embodiment and may not necessarily be present in all embodiments. Thus, respective appearances of the phrases "in one embodiment", "in an embodiment", or "in a specific embodiment" or similar terminology in various places throughout this specification are not necessarily referring to the same embodiment. Furthermore, the particular features, structures, or characteristics of any particular embodiment may be combined in any suitable manner with one or more other embodiments. It is to be understood that other variations and modifications of the embodiments described and illustrated herein are possible in light of the teachings herein and are to be considered as part of the spirit and scope of the invention. Whether specifically noted as non-limiting examples or not, language describing examples, including "such as", "including", "other instances", "merely exemplary", "for instance", "for example", "etc.", e.g.", "as well as", "the like", and similar terms are understood to be non-limiting.

Titles and headings of sections of this disclosure are for convenience only and shall not affect the scope or interpretation of any aspect of this disclosure.

It is understood that variations of components and/or parameters discussed in relation to one embodiment described herein can be incorporated into other embodiments described herein. In non-limiting examples, ranges and related gradations for different temperatures, pressures, time, number of cycles, ratios, volumes, dimensions, current, voltage, fluorescence, brightness, and/or distances, etc. discussed in relation to one embodiment can also be incorporated into other embodiments disclosed herein. In addition, different configurations of components, including non-limiting examples such as pistons, chambers, cylinders, probes, sensors, power sources, detectors, lysis, and/or reagents, etc. discussed in relation to one embodiment can also be incorporated into other embodiments disclosed herein.

In the description herein, numerous specific details are provided, such as examples of components and/or methods, to provide a thorough understanding of embodiments of the invention. One skilled in the relevant art will recognize, however, that an embodiment may be able to be practiced without one or more of the specific details, or with other apparatus, systems, assemblies, methods, components, materials, parts, and/or the like. In other instances, well-known structures, components, systems, materials, or operations are not specifically shown or described in detail to avoid obscuring aspects of embodiments of the invention. While the invention may be illustrated by using a particular embodiment, this is not and does not limit the invention to any particular embodiment and a person of ordinary skill in the art will recognize that additional embodiments are readily understandable and are a part of this invention.

At least a portion of embodiments discussed herein can be implemented using a computer communicatively coupled to a network (for example, the Internet), another computer, or in a standalone computer, or as an Internet of Things (IoT) device (i.e., a smart device which may function on [i.e., as part of] the Internet of Things). As is known to those skilled in the art, a suitable computer can optionally include a processor or central processing unit ("CPU"), at least one read-only memory ("ROM"), at least one random access memory or volatile memory store ("RAM"), at least one non-volatile memory store, for example flash memory or a hard drive ("HD"), and one or more input/output ("I/O") device(s). The I/O devices can include a keyboard, monitor, LCD screen, input buttons or other actuators, printer, internal sensors related to the physical state, position, activity, history, magnetic field, or other aspects of the device, electronic pointing device (for example, mouse, trackball, stylist, touch pad, etc.), or the like.

ROM, RAM, and HD are computer memories for storing computer-executable instructions executable by the CPU or capable of being complied or interpreted to be executable by the CPU. Suitable computer-executable instructions may reside on a computer readable medium (e.g., ROM, RAM, and/or HD), hardware circuitry or the like, or any combination thereof. Within this disclosure, the term "computer readable medium" or is not limited to ROM, RAM, and HD and can include any type of data storage medium that can be read by a processor. For example, a computer-readable medium may refer to a data cartridge, a data backup magnetic tape, a floppy diskette, a flash memory module or drive, an optical data storage drive, a CD-ROM, ROM, RAM, HD, or the like. Software implementing some embodiments disclosed herein can include computer-executable instructions that may reside on a non-transitory computer readable medium (for example, a disk, CD-ROM, a memory, etc.). Alternatively, the computer-executable instructions may be stored as software code components on a direct access storage device array, magnetic tape, floppy diskette, optical storage device, or other appropriate computer-readable medium or storage device.

Any suitable programming language (e.g. C, Assembler, Perl, Python, Java, PHP, Ruby, Swift, Cobol) can be used to implement the routines, methods or programs of embodiments of the invention described herein, including the custom script. Other software/hardware/network architectures may be used. For example, the software tools and the custom script may be implemented on one computer or shared/distributed among two or more computers in or across a network. Communications between computers implementing embodiments can be accomplished using any electronic, optical, radio frequency signals, or other suitable methods and tools of communication in compliance with known network protocols. Additionally, any signal arrows in the drawings/figures should be considered only as exemplary, and not limiting, unless otherwise specifically noted. Based on the disclosure and teachings provided herein, a person of ordinary skill in the art will appreciate other ways and/or methods to implement the invention.

Any embodiment of any of the present methods, composition, kit, and systems may consist of or consist essentially of—rather than comprise/include/contain/have—the described steps and/or features. Thus, in any of the claims, the term "consisting of" or "consisting essentially of" may be substituted for any of the open-ended linking verbs recited above, in order to change the scope of a given claim from what it would otherwise be using the open-ended linking verb.

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about", "substantially" or "approximately" is used to indicate that a value includes the standard deviation of error for the device or method being employed to determine the value as well as an allowance of plus or minus ten-percent (10%).

As used herein, the terms "proximal to", "near", "adjacent to", "disposed near" are used to indicate that two entities are related spatially and in proximity.

As used herein, the terms "amplify", "amplification", "replicate", "replication", and related terms when used in the context of nucleic acids, means to increase the amount or concentration of an identical or similar nucleic acid or nucleic acid sequence or related compound.

As used herein, "controlling" a temperature is used to indicate the active regulation of an element or elements in an attempt to maintain an approximate temperature range for some portion of the device, or the design elements which permit by passive or regulated loss of heat to the environment or other elements such heat loss as to achieve or attempt to achieve an approximate temperature range.

As used herein, "opposite" is used to indicate in a direction on average that is different to, orthogonal to, or opposing the general net vector of the first direction.

As used herein, when referring to movement of, or action on, a fluid, it is understood that this includes movement of, or action on, a fraction or subset of the fluid.

Following long-standing patent law, the words "a" and "an," when used in conjunction with the word "comprising" in the claims or specification, denotes one or more, unless specifically noted.

As used herein, the terms "comprises," "comprising," "includes," "including," "has," "having," or any other variation thereof, are intended to cover a non-exclusive inclusion. For example, a process, product, article, or apparatus that comprises a list of elements is not necessarily limited only those elements but may include other elements not expressly listed or inherent to such process, process, article, or apparatus.

Furthermore, the term "or" as used herein is generally intended to mean "and/or" unless otherwise indicated. For example, a condition A or B is satisfied by any one of the following: A is true (or present) and B is false (or not present), A is false (or not present) and B is true (or present), and both A and B are true (or present). As used herein, including the claims that follow, a term preceded by "a" or "an" (and "the" when antecedent basis is "a" or "an") includes both singular and plural of such term, unless clearly indicated within the claim otherwise (i.e., that the reference "a" or "an" clearly indicates only the singular or only the plural). Also, as used in the description herein, the meaning of "in" includes "in" and "on" unless the context clearly dictates otherwise.

As used herein, "patient" or "subject" includes (whether living or not) mammalian organisms, such as human and non-human mammals, for example, but not limited to, rodents, mice, rats, non-human primates, companion animals such as dogs and cats as well as livestock, e.g., sheep, cow, horse, etc., as well as non-mammalian animals such as birds, reptiles, fishes, insects, crustaceans, arachnids, echinoderms, worms, mollusks, sponges, and other nucleic acid-bearing life such as Bacteria, viruses, Fungi, Protozoa, Archaea, Chromista and other plant life. Therefore, for example, although the described embodiments illustrate use of the present methods on humans, those of skill in the art would readily recognize that these methods and compositions could also be applied to veterinary medicine as well as on other animals and other types of organisms described herein.

As used herein, the terms "piston", "pistons" and related terms include a mass that moves from a first position to a second position (and potentially back to the first position) in a substantially linear, or by means of mechanical linkage effects motion along such a path. The mass may be a displacer piston, which is a piston that is used to move fluid from one location to another. The mass, in certain embodiments, may be a solid, unitary component, or may comprise multiple components including for example, multiple discs, polyhedrons or coated granules which may be of similar or different shapes.

As used herein, the term "dilution fluid" and related terms include any fluid that is mixed with another substance (e.g. fluid or solid) to dilute the concentration of the substance.

BRIEF DESCRIPTION OF THE DRAWINGS

FIG. 2 is a partially exploded front view of the embodiment of FIG. 1.

FIG. 3 is a partially exploded top view of the embodiment of FIG. 1.

DETAILED DESCRIPTION OF THE INVENTION

Exemplary embodiments of the present disclosure include apparatus and methods for the detection of nucleic acids and performing molecular diagnostics. Particular embodiments are discussed below with reference to the drawings included in the figures. For purposes of clarity, each element referred to in the discussion below of the figures may not be labeled with a reference number in each figure.

Figure 1:
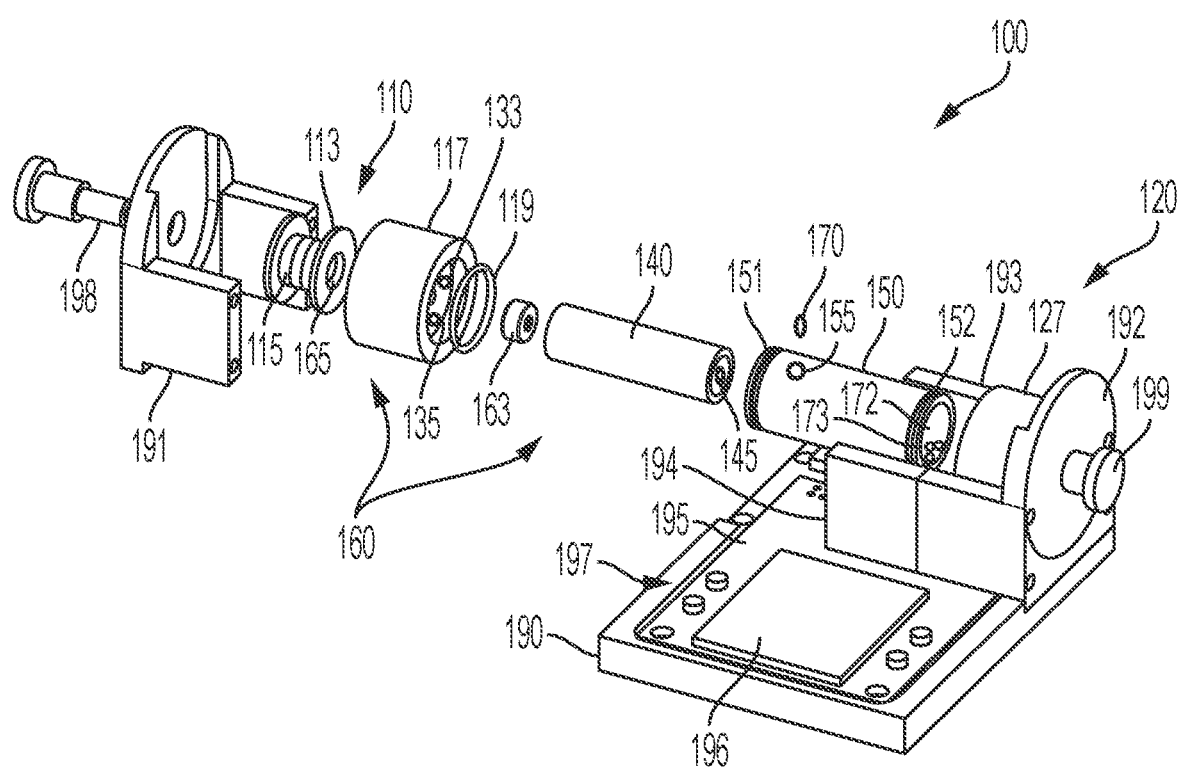
FIG. 1 is a partially exploded perspective view of an apparatus according to a first exemplary embodiment of the present disclosure.

Referring initially to FIGS. 1-3, an apparatus 100 for performing molecular diagnostics is shown in partially-exploded perspective, front and top views, respectively. In this embodiment, apparatus 100 comprises a piston 140 with a central channel 145 disposed within a housing 150 having a first end 151 and a second end 152. In the illustrated embodiment (and other similar embodiments described and/or illustrated herein) piston 140 is an example of a displacer piston. In addition, apparatus 100 comprises a first heat source 110 near first end 151 and an optional second heat source 120 near second end 152.

In the embodiment shown, apparatus 100 also comprises an actuator 160 configured to cycle piston 140 between a first position near first end 151 and a second position near second end 152 of housing 150. In the views shown in FIGS. 1-3, first heat source 110 and a first portion of actuator 160 is shown in an exploded view, while heat source 120 and a second portion of actuator 160 is shown in an assembled view. It is understood the components shown in the figures are merely exemplary of one embodiment, and other embodiments may comprise a different combination of components.

In the illustrated embodiment, apparatus 100 comprises a base 190 supporting a controller 195, a first support member 191, a second support member 192 and spacer members 193 and 194 between the support members. End caps 117 and 127 are coupled to support members 191 and 192 via coupling members 198 and 199, respectively. As shown in the exploded portion of the figures, apparatus 100 comprises a cylinder 113 with an actuation coil 165 and a heating coil 115. As explained in further detail below, actuation coil 165 can be used to provide electromagnetic impulses to position piston 140 within housing 150, while heating coil 115 can be used to heat fluid within housing 150 to a desired temperature. While actuation coil 165 and heating coil 115 are shown and described as separate coils in the illustrated embodiment, other embodiments may comprise a single coil that performs actuation and heating functions. Apparatus 100 further comprises an illumination module 133 and a detection module 135. While the discussion of the figures will be primarily directed to the components shown in the exploded portion near first end 151, it is understood apparatus 100 comprises generally equivalent components near end 152, unless otherwise noted.

Apparatus 100 can be assembled by inserting piston 140 into housing 150, which can then be inserted into end cap 127 via end 152. Magnetic element 163 can then be inserted into housing 150 and end cap 117 coupled to first end 151 of housing 150 with a seal member 119 providing sealing between the components. The magnetic elements can vary in shape, as rings, discs, or mixed into the polymer of the piston as a powder during manufacture, as well as composition, with rare earth magnets preferred to ferrous magnets due to their preferred chemistry and field strength per unit mass, and chromed or otherwise coated magnets preferred, and magnets embedded in the polymer more preferred to prevent chemical inhibition of reagents such as those involved in lysis, extraction, detection, and particularly, amplification, and mitigate the risk of mechanical shifting during operation. An optional embodiment is to use maxels (or magnetic units incorporated through 3D printing or other modes which confer a designable magnetic field, for example see U.S. Pat. No. 9,105,384, incorporated herein by reference). Magnets may also be fixed or induced (for example in the embodiment of the piston using coated granules) and magnets may also be incorporated as a power-saving feature by including fixed magnets at locations such that at the full stroke of the piston, they exert a latching force to passively hold the piston in place during the applicable heating cycle step. This embodiment is also useful in scenarios where the orientation of the apparatus may change during use.

Cylinder 113 is inserted into end cap 117 and support member 191 is coupled to base 190 and spacer members 193 and 194. The order of assembly for the components of apparatus 100 is not required in the order described above, and other assembly sequences may be utilized. In addition, other embodiments may combine into a single component certain elements that are shown in FIGS. 1-3 as separate components.

An overview of the operation of apparatus 100 will be presented initially, followed by more detailed discussion of particular aspects. During operation of apparatus 100, a biological sample 170 is introduced into a sample port 155 of housing 150 for analysis. In certain embodiments, housing 150 can contain buffers 172 and reagents 173 suitable for molecular diagnosis of sample 170, including sample preparation (e.g., sample dilution, lysis, extraction, purification or other isolation techniques) and amplification or replication (e.g., via qualitative, quantitative, or semi-quantitative PCR, RT-PCR or other thermal cycling or isothermal techniques) as well as detection (e.g. hydrolysis probes or molecular beacons). In certain embodiments, reagents 173 and/or buffers 172 may be lyophilized pellets. While certain embodiments of the device, such as the piston model are preferably used in conjunction with thermocycling amplification techniques, the device is also capable of amplification in an isothermal fashion.

Figure 4:
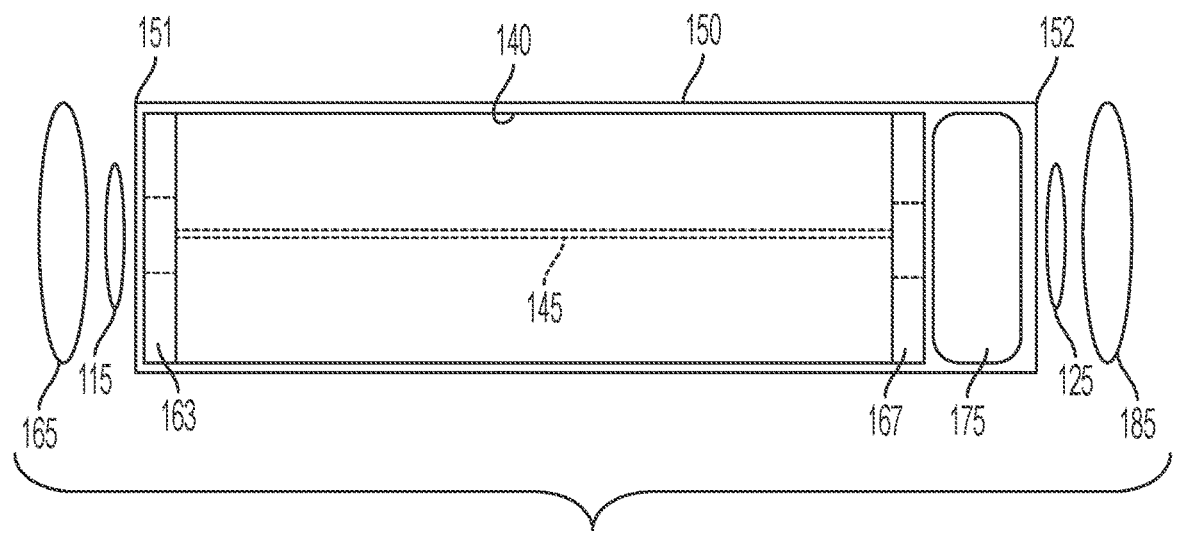
FIG. 4 is a schematic view showing the piston of the embodiment of FIG. 1 in a first position.
Figure 5:
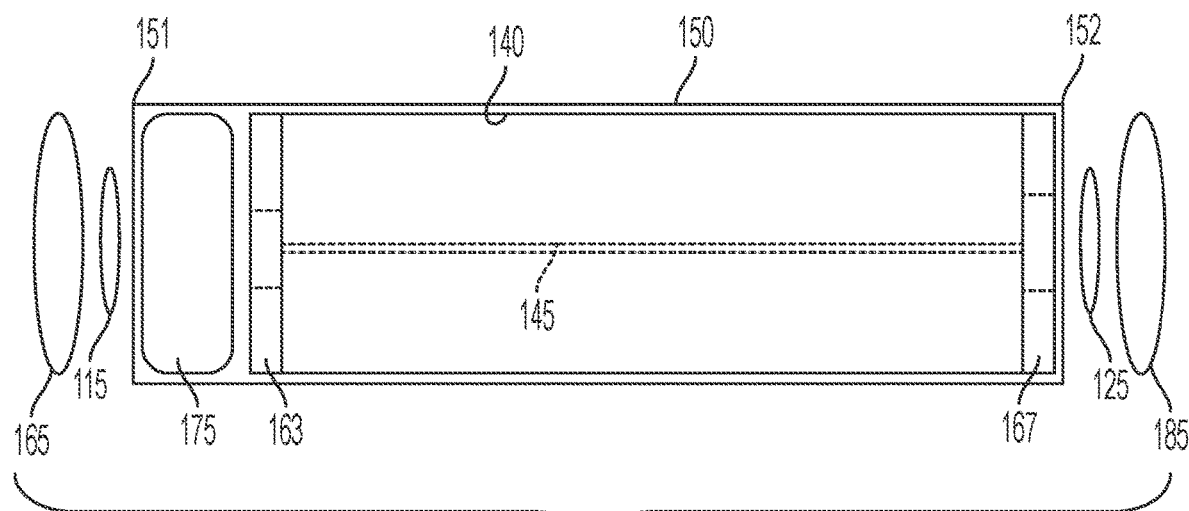
FIG. 5 is a schematic view showing the piston of the embodiment of FIG. 1 in a second position.

Referring additionally to FIGS. 4 and 5, schematic views are shown of piston 140 in a first position near first end 151 and in a second position near second end 152 of housing 150. During operation of apparatus 100, a reaction fluid 175 comprising prepared sample 170, buffers 172 and/or reagents 173 can be thermally cycled to amplify or replicate components of the reaction fluid (e.g. a nucleic acid) for further analysis. As explained in further detail below, controller 195 (shown in FIGS. 1-3) can control the flow of electric current through actuation coil 165 and a second actuation coil 185 to cycle piston 140 between a first position near first end 151 and a second position near second end 152. In addition, controller 195 can control the flow of electric current through heating coil 115 and a second heating coil 125 to control the temperature of first end 151 and second end 152 of housing 150. In exemplary embodiments, electric power may be supplied to apparatus 100 via batteries, a USB power source connected to any enabled device, such as a computer, smart phone, tablet, solar cell or photovoltaic cell, or an alternating current source (e.g. a typical electrical outlet). In other embodiments, electric power may be supplied to apparatus 100 via a wireless a charging mechanism connected to any enabled device, such as a computer, smart phone, tablet, solar cell or photovoltaic cell, or an alternating current source (e.g. a typical electrical outlet).

In the embodiment shown, actuator 160 can exert electromagnetic forces on magnetic element 163 via actuation coil 165 near end 151 of housing 150. In the illustrated embodiment, actuator 160 comprises second actuation coil 185 and magnetic element 167 (located between piston 140 and the second end 152 and not visible in FIGS. 1-3) in the assembled portion of apparatus 100 near second end 152 of housing 150. It is understood that other embodiments may comprise a different number of actuation coils, heating coils, and magnetic elements. Moreover, the placement of coils may be varied to allow a linear acceleration or other behavior as desired, and the heating and movement functions may be performed separately or in tandem, with an optional polarity switch via an H-bridge to minimize the number and complexity of included components. In some embodiments, an H-bridge can obviate the need for a dedicated magnetic coil, and instead direct current to the first end 151 or the second end 152, where the first heating coil 115 and the second heating coil 125 serve as a first heat source 110 and a second heat source 120 respectively, as well as the other magnetic element 167. In some embodiments, the size and spacing of the other magnetic element is adjusted to make the proximity of the magnetic element to the magnetic coil no more than 0.1 mm, 0.2 mm, 0.3 mm, 0.4 mm, 0.5 mm, 0.75 mm, 1 mm, 2 mm, 3 mm, or more radially.

Additional modes of movement may be employed, including gravity, centripetal, lever, camshaft, or manual movement, though for precision and efficiency of components and power, electromagnetic motion is preferred in the embodiment shown.

First heat source 110 comprises heating coil 115 wrapped around cylinder 113. Electric current passing through heating coil 115 increases the temperature of cylinder 113 and nearby components, including first end 151 of housing 150. In particular embodiments, cylinder 113 may be formed from a metal or other suitable material with a high heat transfer coefficient. In a specific embodiment, cylinder 113 may be formed from aluminum. Accordingly, heat from cylinder 113 will be efficiently transferred to housing 150 and the contents of housing 150 (e.g. reaction fluid 175) near first end 151.

Referring back now to FIGS. 1-5, controller 195 can also control the position of piston 140 within housing 150 by controlling the flow of electric current through actuation coil 165 and second actuation coil 185 (also shown in FIGS. 4 and 5, not visible in the assembly within end cap 127 of FIGS. 1-3). Piston 140 is shown initially in a first position near first end 151 in FIG. 4. In this position, reaction fluid 175 is near second end 152 of housing 150. Controller 195 can control an electric current that flows through coil 165, generating an electromagnetic force that acts on magnetic element 163. When the electric current flows through coil 165 in one direction, an electromagnetic force will be exerted on magnetic element 163 that repels magnetic element 163. Magnetic element 163 in turn moves piston 140 toward second end 152 of housing 150. A schematic view of piston 140 shown in this position is shown in FIG. 5. As shown in FIG. 5, when piston 140 is moved toward second end 152, reaction fluid 175 in housing 150 will be displaced such that reaction fluid 175 is near first end 151 of housing 150. In the embodiment shown, channel 145 is a central capillary channel that provides a path for reaction fluid 175 to flow between first end 151 and second end 152 as piston 140 is cycled between the first and second positions shown in FIGS. 4 and 5. In certain embodiments, piston 140 may comprise additional channels or other features to allow for the displacement of reaction fluid 175. For example, in some embodiments the diameter of piston 140 and housing 150 can sized appropriately to provide a desired flow path around piston 140 for reaction fluid 175 as piston moves from a first position near first end 151 to a second position near second end 152. Piston 140 may also comprise channels on the external diameter to allow flow of reaction fluid 175.

Controller 195 can also direct piston 140 back toward first end 151 to the position shown in FIG. 4 so that reaction fluid 175 in housing 150 is displaced near second end 152 of housing 150. In order to move piston 140 from the position shown in FIG. 5 to the second position shown in FIG. 4, controller 195 can stop the flow of current through actuation coil 165 to stop the magnetic force acting on magnetic element 163 via actuation coil 165. In certain embodiments, controller 195 can reverse the flow of current through actuation coil 165 to create a magnetic force that attracts magnetic element 163 via actuation coil 165. In addition, controller 195 can apply an electrical current to second actuation coil 185 near second end 152 of housing 150. This can create an electromagnetic force that repels a second magnetic element 167 positioned between piston 140 and second end 152. Second magnetic element 167 in turn moves piston 140 toward first end 151 of housing 150, displacing reaction fluid 175 near second end 152.

Controller 195 can therefore control the position of piston 140, as well as the temperature at first end 151 and second end 152 of housing 150, by controlling the flow of electric current to the heating and actuation coils as described above. It is understood the configuration of heat source 110 and 120 and actuator 160 shown in the figures is merely exemplary of one embodiment. Other embodiments may include different configurations, including for example, resistor or polyimide heaters and/or linear actuators. Reaction fluid 175 can accordingly be cycled from a first temperature range (e.g. the temperature maintained of first end 151) to a second temperature range (e.g. the temperature maintained of second end 152) in order to amplify or replicate components of the reaction fluid. In some embodiments, including for example certain PCR and RT-PCR processes, reaction fluid 175 can be maintained at a temperature of approximately 92-98° C. when reaction fluid 175 is near first end 151 and maintained at a temperature of approximately 60-65° C. when reaction fluid 175 is near second end 152.

In certain embodiments, apparatus 100 can cycle piston 140 and reaction fluid 175 from the first to the second position and back to the first position between approximately 15 and 60 times, or preferably between about 30 and 50 times. Accordingly, reaction fluid 175 can be cycled from about 92-98° C. to about 50-65° C., particularly about 60-65° C. between about 30 and 50 times. In certain embodiments utilizing a PCR process, reaction fluid can be maintained at about 92-98° C. for approximately two to five minutes initially, and then cycled between about 92-98° C. for approximately 3-30 seconds (or more particularly about 3-15 seconds, or even more particularly about 5 seconds) and about 60-75° C. for approximately 5-30 seconds (or more particularly about 5-15 seconds, or even more particularly about 10 seconds) for about 30-50 cycles. In certain embodiments utilizing a RT-PCR process, reaction fluid can be maintained at approximately 34-60° C. (or more particularly about 45-55° C. or even more particularly about 50° C.) initially, then maintained at about 92-98° C. (or optionally, lower for targets without genomic DNA present, in which case the preferred temperature corresponds to the dissolution temperature of the primer—target sequence) for approximately two to five minutes. The reaction fluid can then be cycled between a first temperature range of about 92-98° C. for approximately 3-30 seconds (or more particularly about 5-15 seconds, or even more particularly about 5 seconds) and a second temperature range of about 50-65° C., particularly about 60-65° C. for approximately 5-30 seconds (or more particularly about 5-15 seconds, or even more particularly about 10 seconds) for approximately 30-50 cycles, or other thermocycling modes as will be apparent to the practitioner. In certain embodiments, the reaction fluid is cycled between the higher temperature range for a specified period of time and the lower temperature range for a specified period of time without an initial period of time at a particular temperature range.

In certain embodiments, controller 195 may include a printed circuit board with a computer processor, computer readable medium and necessary hardware (e.g. electrical switches, voltage transformers, regulators, etc.) configured to execute the steps to automatically operate apparatus 100. For example, controller 195 can include components needed to automatically position piston 140 and control the temperature of first end 151 and second end 152 (and consequently, the temperature of reaction fluid 175 as reaction fluid 175 is displaced by piston 140 as described below) when a user initiates operation (e.g. by pressing a start button).

In the embodiment shown, controller 195 can control the temperature of the contents of housing 150 near first end 151 by controlling the flow of electric current through heating coil 115. Controller 195 can also control the temperature of housing 150 near second end 152 by controlling the flow of electric current through second heating coil 125 (shown in FIGS. 4 and 5, not visible in the assembly within end cap 127 of FIGS. 1-3) wrapped around a second cylinder (not visible within the assembly in end cap 127). For example, the temperature of first end 151 (or fluid within housing 150 near first end 151) can be measured and provided as an input to controller 195. If the measured temperature is lower than a target temperature (e.g. a setpoint stored in controller 195), then controller 195 can increase the flow of electric current to heating coil 115. If the measured temperature is higher than the target temperature, then controller 195 can decrease the flow of electric current to heating coil 115. Controller 195 can similarly control the temperature of second end 152 (or fluid within housing 150 near second end 152).

In another embodiment, referring initially to FIGS. 12-15, an apparatus 200 for performing molecular diagnostics is shown. Several aspects of this embodiment operate in a manner generally equivalent to previously-described embodiments. The embodiment shown in FIGS. 12-15 also includes components to provide for ingress of the sample, as well as mixing of the sample with dilution fluids, buffers and/or reagents used in the amplification and detection of sample analytes. In this embodiment, apparatus 200 comprises a housing 150 which comprises a first end 151 and a second end 152, as well as an optional housing thermal break 253. Electric current passing through a first heating coil (not shown in the figures for purposes of clarity within heat source 110) provides resistive heat for the first heat source 110 and electric current passing through a second heating coil (not shown in the figures for purposes of clarity within heat source 120) optionally provides resistive heat for the second heat source 120. Electrical power can be supplied by one or more batteries 296 retained in in one or more battery holders 297.

In this embodiment, piston 140 comprises a piston thermal break 242, magnetic element 163, and a piston cap 241. In the embodiment shown, magnetic element 163 comprises a small ring magnet, though as described elsewhere there are many additional embodiments that will be readily apparent to include a magnetic element within the piston 140. In this embodiment, magnetic element 163 is between piston cap 241 and piston thermal break 242 as separate components, though as described elsewhere, piston 140 may be formed as a single piece by use of injection molding, press-fit, friction-welded, or any other number of similar suitable techniques. Glues may also be used to construct piston 140, though these are less-preferred as certain chemical elements, such as epoxies, can negatively affect reaction chemistries.

Figure 15:
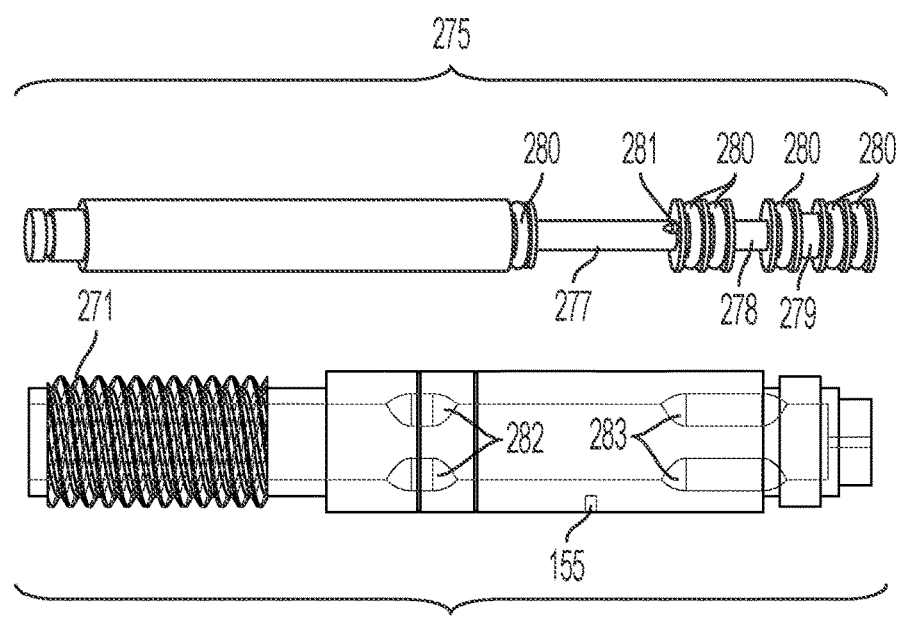
FIG. 15 is an exploded perspective view of components used for sample loading and ingress in the embodiment of FIG. 12.

The piston 140 is located within the housing 150, with the first end of the housing bounded by the ingress housing 274. Ingress housing 274 may be formed from a variety of materials such as polymers (e.g. Delrin) or metals (e.g. aluminum), or a combination thereof, including thin coatings, conformal coatings, spin coatings, dip coatings, film coatings, vacuum deposition coatings, sputter deposition coatings and other types of methods. As shown in FIG. 15, ingress housing 274 may contain an ingress plunger or rod assembly 275, which comprises various chambers and sealing members to allow the proper mixing or fractionation of the biological sample 170. In this particular embodiment, rod assembly 275 may contain an ingress sample chamber 279. In addition, rod assembly 275 may comprise an upper ingress dilution chamber 277 and a lower ingress dilution chamber 278, which are in fluid communication via a dilution channel 281, though in other embodiments, a single dilution chamber may be used. In this embodiment, ingress rod assembly 275 also comprises sealing members 280. In certain embodiments, sealing members 280 may comprise or incorporate O-rings or other components as desired to improve or effect separation of the component chambers, including those which swell or react to hydration or chemical species. The volume of dilution chambers 277 and 278, as well as sample chamber 279, is determined by the dimensions of ingress rod assembly 275 and ingress housing 274. For example, the distance between sealing members 280, as well as the diameter of ingress rod assembly 275 and ingress housing 274 can be selected to determine the desired volume for each chamber.

The ingress housing 274 may also include various contours to assist in the mixing or fractionation of the biological sample, lysate, or other reaction fluids and reagents. In this particular embodiment, the ingress housing 274 comprises an upper ingress bypass 282 and a lower ingress bypass 283. As discussed more fully below, upper ingress bypass 282 and a lower ingress bypass 283 can selectively place chambers within ingress housing 274 (e.g. sample chamber 279 and dilution chambers 277 and 278) in fluid communication with a piston chamber 157. In particular embodiments, the position of ingress rod assembly 275 can place sample chamber 279 and/or dilution chambers 277 and 278 in fluid communication with piston chamber 157. Specifically, the position of sealing members 280 can allow or restrict fluid communication between piston chamber 157 and sample chamber 279 and dilution chambers 277 and 278 or the outside atmospheric pressure.

The dilution chambers 278 and 277 can be filled with a dilution fluid. In some embodiments, the shelf-stable components of the reaction (e.g. salts) can be present in the dilution fluid, while less-stable components (e.g. proteins) can be present in lyophilized components that are separate from the dilution fluid for example in a lyophilized pellet 527. This allows a longer-term storage mode without the need for refrigeration and a wider storage temperature range. In some embodiments, the unrefrigerated shelf-life of the apparatus can be 1 day, 2 days, 3 days, 4 days, 5 days, 6 days, 1 week, 2 weeks, 1 month, 3 months, 6 months, 9 months, 12 months, 18 months, 24 months, 30 months, 36 months, 48 months, 60 months, or more. In other embodiments, the potency loss (or effective chemical action ratio) at each of the above time points is less than 1%, 3%, 5%, 10%, 20%, 25%, 35%, 50%, or more. In some embodiments the acceptable storage temperature range of the self-stable apparatus may include temperatures less than 10° C., between 10-15° C., 15-25° C., 25-35° C., 35-45° C., 45-55° C., 55-65° C., or higher.

Depending on the desired dilution, the relative volume of the dilution chambers to the ingress sample chamber 279 can be adjusted. In this particular embodiment, the ratio of the ingress sample chamber to the dilution fluid in the dilution chambers has a ratio of 1:10. The ratio of the ingress sample chamber to the dilution fluid in the dilution chambers may have a ratio of between about 1:1 to 1:5, between about 1:5 to 1:10, between about 1:10 to 1:15, between about 1:15 to 1:25, between about 1:25 to 1:50 or between about 1:50 to 1:100. Diluting the biological sample has the effect of diluting inhibitors of PCR and decreasing the viscosity of the biological sample. As such, the ratio may be adjusted depending on the particular tissue matrix or biological sample type being assayed. The use of designs which incorporate non-laminar flow and create fluid turbulence effects a mixing function to the ingress. The turbulence can be effected by means of channels, asperities, vortex shedding, changes in fluid speed, venturi effects, and other fluid mechanical effects that will be apparent to the practitioner.

Sample Acquisition

In particular embodiments, sample 170 may comprise a biological sample, raw sample, or matrix, including for example, saliva, mucus, tears, hair, nails, hair follicle, sputum, phlegm, a buccal, nasal or nasopharyngeal swab, lacrimal fluid, rheum, blood, whole blood, plasma, serum, urine, urethral fluid, smegma, semen, vaginal secretions, breast milk, colostrum, ear wax, sebum, wound sample, pus, skin scraping, tumor, cyst, feces, cerebrospinal fluid, pericardial fluid, lymph fluid, synovial fluid, bile, gastric fluid, chyme, chyle, amniotic fluid, lochia, placenta, vitreous body, aqueous humor, material from plants, animal, bacterial, viral, fungal, archaebacteria, insects, Chromista, Protozoa, and other nucleic acid-bearing life, as well as, environmental sources such as water, air, or soil, and other sources that will be apparent to the practitioner.

The sample may be used directly as obtained from the biological source or following a pretreatment to modify the character of the sample. For example, such pretreatment may include preparing plasma from blood or diluting viscous fluids. Methods of pretreatment may also involve, but are not limited to, filtration, precipitation, dilution, distillation, mixing, centrifugation, freezing, lyophilization, concentration, amplification, nucleic acid fragmentation, inactivation of interfering components, the addition of reagents or lysing. In some embodiments, the sample comprises whole cells (e.g., whole cells from the subject, whole cells from a pathogen [e.g., bacterial pathogen]). In some embodiments, the sample may or may not have been subjected to one or more of sonication, ultrasonication, traditional lysis reagents, chaotropes, and/or other traditional lysis reagents. In some embodiments, the sample may be contacted with a detergent and/or proteinase, such as proteinase K, for lysis. The sample may be subjected to heat, such as 70° C., 80° C., 90° C. or greater temperatures.

In certain embodiments a user may expectorate into sample port 155 or a collection chamber or spittoon 257 coupled thereto. In particular embodiments, a user may use a swab that contains a liquid dilution or carrier fluid that dilutes the biological sample (e.g. by a ratio greater than 2:1, 3:1, 5:1, or more particularly by a 10:1 ratio in some embodiments). In certain embodiments, the swab is rayon, polyester, cotton, nylon or other natural or synthetic fibers. In some embodiments, the swab may be flocculated or enhanced to increase absorption or rapid elution of biological specimens. In certain embodiments, the dilution fluid may be present in the swab and/or present in housing 150. In specific embodiments, the dilution (carrier) fluid comprises: NP-40, 0.05-0.5%; Tween-20, 0.05-0.5%; EDTA, 0.5-5 mM; and Tris-HCl (or alternatively, bis-tris propane, sodium phosphate, tris-acetate, or other suitable buffer components which will be known to the practitioner. See, for example, Mohan, A guide for the preparation and use of buffers in biological systems, Calbiochem, 2003, incorporated herein by reference), pH 7.5 (pH may be adjusted to suit the assay and tissue matrix, but generally has a preferred pH range of 7.0 to 10.5), 5-50 mM. Other detergents may be used, such as Sarkosyl, Triton X-100, Triton X-114, Tween 80, Brij-35, Brij-58, and sodium dodecyl sulfate. In other embodiments, heat-based lysis may be used in lieu of, or in addition to, chemical lysis. In a specific embodiment, a biological specimen may be heated (e.g. to a temperature in the range 80° C. to 95° C.) either in optional conjunction with dilution as discussed elsewhere, or optional conjunction with detergent(s) as discussed herein. For simple bacterial samples lacking material inhibitors to PCR, heat lysis alone can be sufficient to lyse cells.

In some embodiments, whole blood may be collected in tubes such as collection tubes containing anticoagulants (e.g., lithium heparin), chelating agents (e.g., EDTA), nuclease and/or protease inhibitors. The sample may be separated into plasma and serum fractions by centrifugation or may be analyzed as whole blood that has not been fractionated or separated into its component parts. Serum separation tubes (SSTs) containing a silicone gel may be used that when centrifuged the silicone gel forms a layer on top of the buffy coat, allowing the blood plasma to be removed more effectively for testing and related purposes. The sample may be incubated with ammonium chloride, sodium bicarbonate and EDTA. Urine may be collected in tube with EDTA. The sample may be contacted with a chaotropic agent (e.g., guanidine thiocyanate), EDTA, detergent (e.g., Triton X-100 or SDS), proteinase, and/or buffer (e.g., Tris-HCl) (Zainabadi et al., PLoS One. 2019; 14(2): e0210813; Kulinski et al., Biomed Microdevices. 2009 June; 11(3): 671-678). Semen samples may be collected and incubated with a lysis buffer (e.g., Tris-HcCl, sodium chloride and magnesium chloride). The sample may further be contacted with TRIzol and proteinase, chloroform, and sodium citrate for extraction of nucleic acids (Darbandi et al., Middle East Fertitility Society Journal, 23(3): 216-219, 2018). In other embodiments, the semen sample may be contacted with a guanidine thiocyanate lysis buffer with tris(2-carboxyethyl)phosphine (TCEP) (Wu et al., Biotechniques. 2014; 58(6): 293-300). Skin samples may be stored in Tris-HCl, EDTA, and Tween. Lysis may be performed using ammonia, followed by neutralization, and salting out of proteins with acetic acid (Sildorova et al., *Experimental Dermatology,* 2011). Viral and bacterial samples may be lysed chemically using reagents, such as Tris-HCl, lysozyme, EDTA and other detergents (e.g., Triton X-100) (Kajivara et al., *J Biomol Tech,* 26(4):118-124, 2015).

Sample Ingress

Sample ingress can be performed in a variety of different manners. In one particular embodiment shown in apparatus 200, a sample can be introduced via a threaded coupling used to advance a rod assembly In this embodiment, ingress rod assembly 275 can be moved relative to the ingress housing 274, and in one or more motions, including a single, unidirectional linear motion, effect several beneficial outcomes. In certain embodiments, ingress rod assembly 275 can be moved relative to ingress housing 274 via a coupling (including a threaded coupling) between components, including for example, a threaded coupling between ingress housing 274 and ingress cap 276. For example, ingress cap 276 can be rotated with respect to ingress housing 274 such that threaded portion 271 moves ingress housing 274 (and ingress rod assembly 275) relative to ingress cap 276.

Referring now to FIGS. 16-26, section views of components used for sample loading and ingress in apparatus 200 are shown in different positions. FIGS. 16-21 illustrate ingress housing 274 and ingress rod assembly 275 in different positions during an assembly or manufacturing process, (e.g. processes typically performed prior to delivery of apparatus 200 to an end user). FIGS. 22-26 illustrate ingress housing 274 and ingress rod assembly 275 in different positions during loading of a sample for analysis by apparatus 200 (e.g. processes typically performed by a user prior to sample analysis). For purposes of clarity, not all elements are labeled with reference numbers in the figures.

Figure 16:
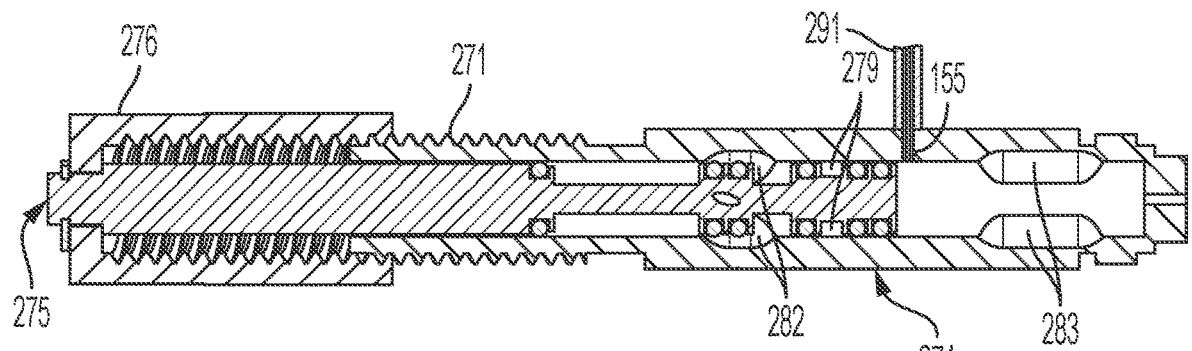
FIGS. 16-26 illustrate section views of components used for sample loading and ingress in the embodiment of FIG. 12 in different positions.
Figure 17:
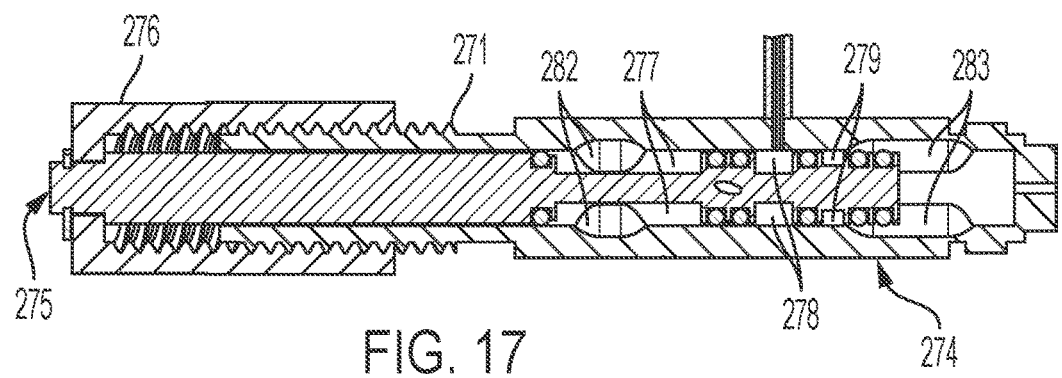

As shown in FIG. 16, ingress rod assembly 275 is initially positioned within ingress housing 274 such that sample port 155 is in fluid communication with lower ingress bypass 283. In the position shown in FIG. 16, lower ingress bypass 283 provides fluid communication with piston Chamber 157 (e.g. lower ingress bypass 283 is not sealed by sealing members 280). Accordingly, a vacuum source 291 can be coupled to sample port 155 and a vacuum applied so that piston chamber 157 is placed under vacuum. In FIG. 17, ingress rod assembly 275 is advanced within ingress housing 274 (e.g., via rotation of cap 276) such that sample port 155 is in fluid communication with lower dilution chamber 278. Again, a vacuum source 291 can be coupled to sample port 155 such that lower dilution chamber 278 is placed under vacuum. In this embodiment, dilution channel 281 provides fluid communication between an upper dilution chamber 277 and lower dilution chamber 278. Accordingly, both upper dilution chamber 277 and lower dilution chamber 278 are placed under vacuum at this stage.

Figure 18:
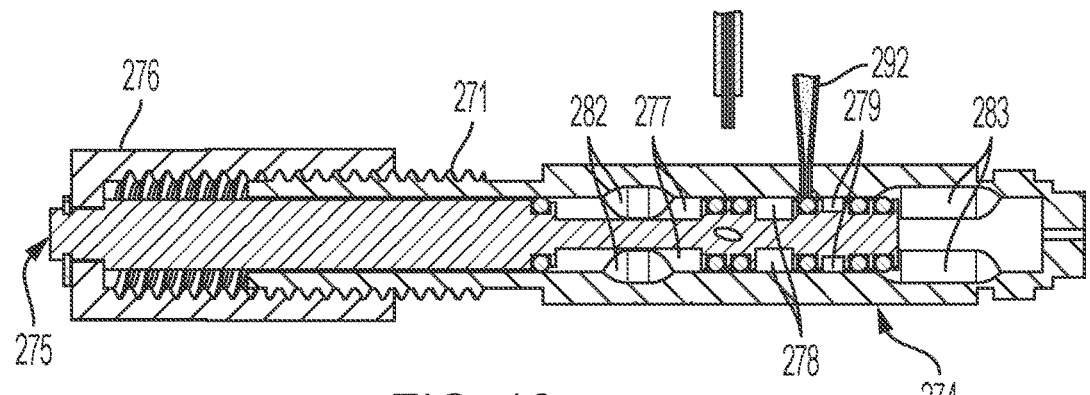
Figure 19:
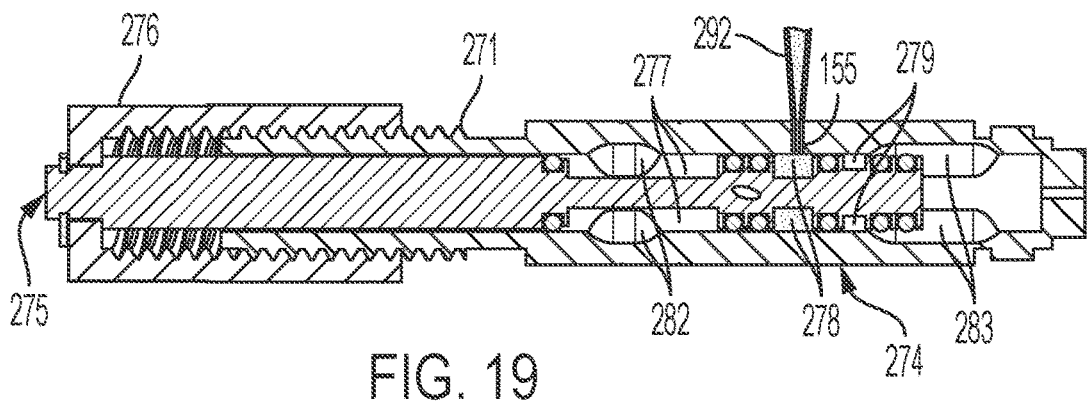

Referring now to FIG. 18, ingress rod assembly 275 is positioned such that sample input port 155 is aligned with a sealing member 280 between sample chamber 279 and lower ingress dilution chamber 278. At this stage, the vacuum source 291 can be removed from sample port 155 and a dilution fluid source 292 can be coupled to sample port 155. In FIG. 19 ingress rod assembly 275 is further advanced such that sample port 155 is in fluid communication with lower ingress dilution chamber 278 (and upper ingress dilution chamber 277 via dilution channel 281). Lower ingress dilution chamber 278 and upper ingress dilution chamber 277 can then be filled with the dilution fluid and the source of dilution fluid removed from sample port 155.

Figure 20:
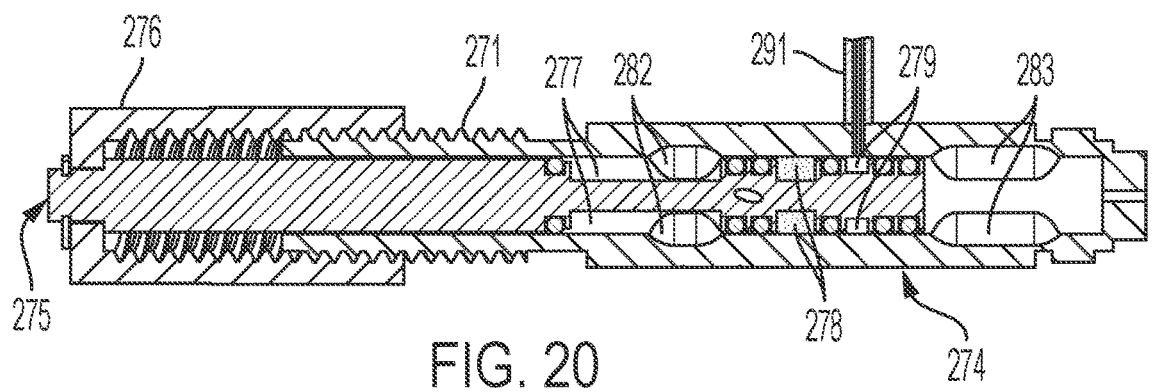
Figure 21:
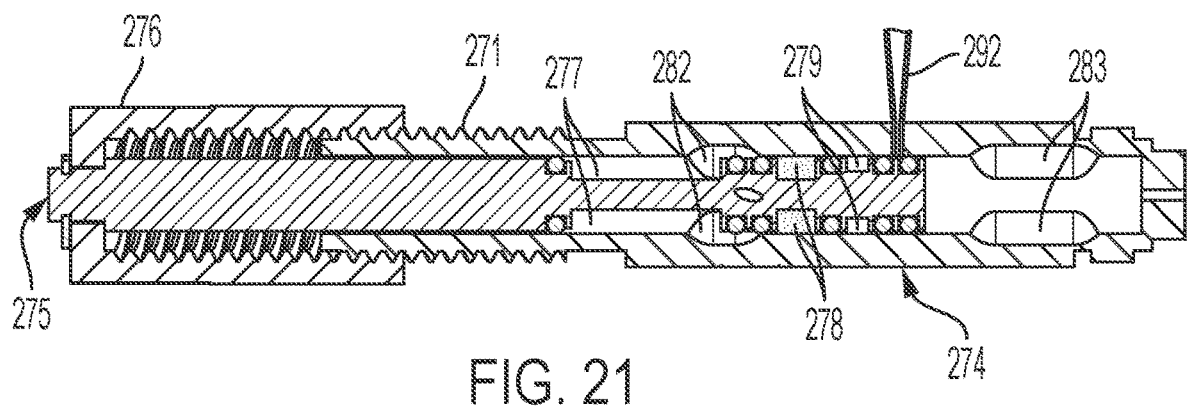

As shown in FIG. 20, ingress rod assembly 275 is retracted from the prior position so that sample port 155 is in fluid communication sample chamber 279. Vacuum source 291 can then be coupled to sample port 155 such that sample chamber 279 is placed under vacuum. Referring now to FIG. 21, ingress rod assembly 275 can be further retracted such that sample port 155 is placed between sealing members 280 at the end of ingress rod assembly 275. In this position, apparatus 200 has a vacuum maintained on sample chamber 279 while lower ingress dilution chamber 278 and upper ingress dilution chamber 277 are filled with dilution fluid. Apparatus 200 is now in a configuration that can be delivered to an end user ready for use. The end user can now place sample fluid in collection chamber 257 (shown in FIG. 14).

Figure 22:
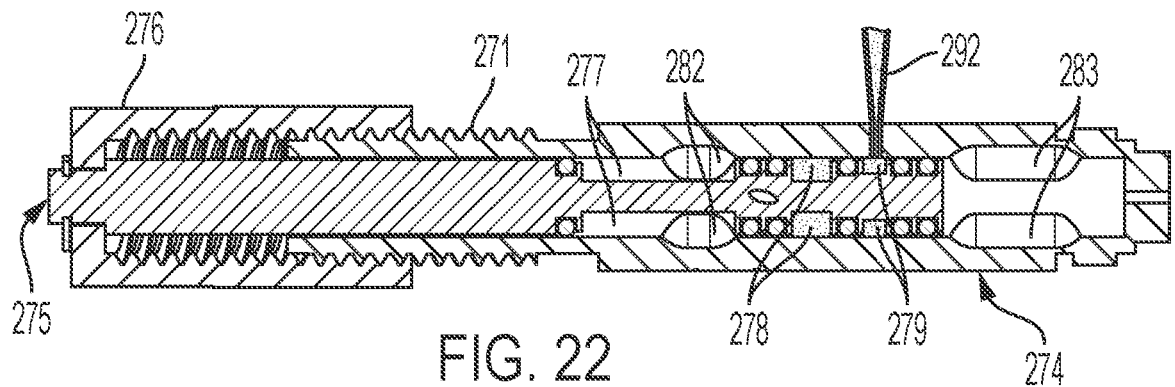
Figure 23:
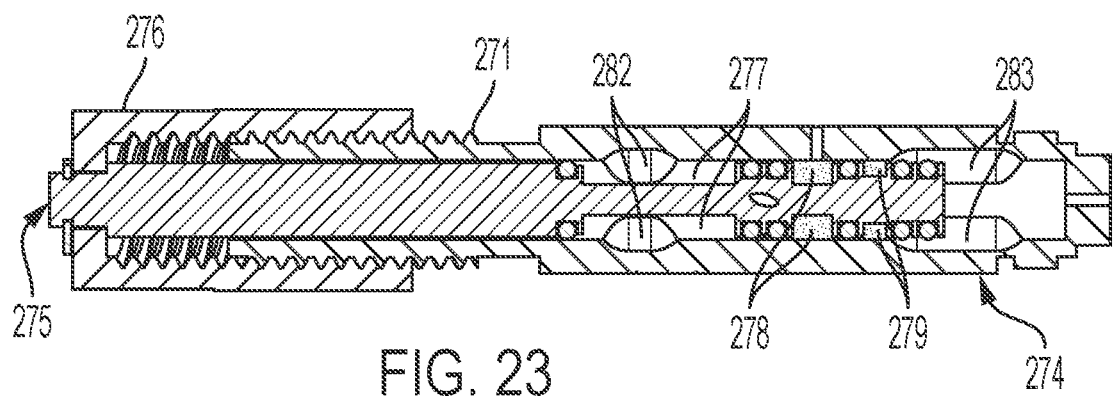

After sample fluid is placed in collection chamber 257, the user can manipulate apparatus 200 (e.g. by rotating ingress cap 276) to place ingress rod assembly 275 in the position shown in FIG. 22. In this position, ingress rod assembly 275 is positioned such that sample port 155 is in fluid communication with sample chamber 279. (which was previously placed under vacuum). Accordingly, a portion of sample fluid from collection chamber 257 can be drawn through sample port 155 into sample chamber 279.

Figure 24:
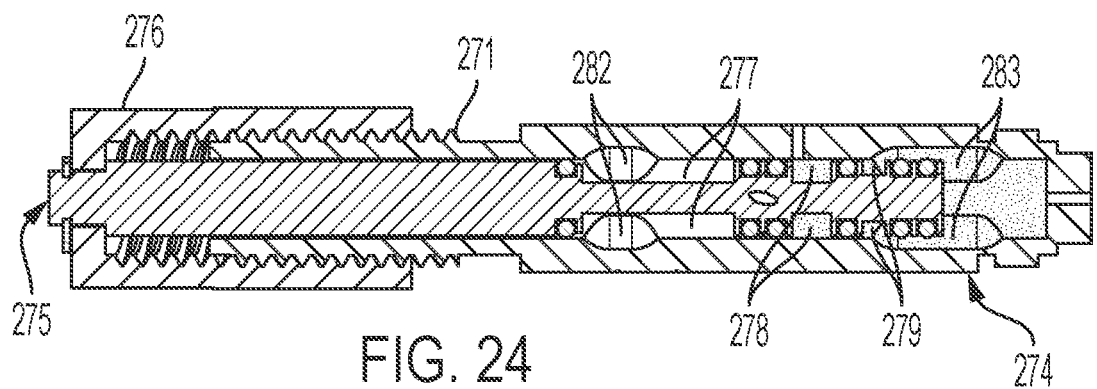
Figure 25:
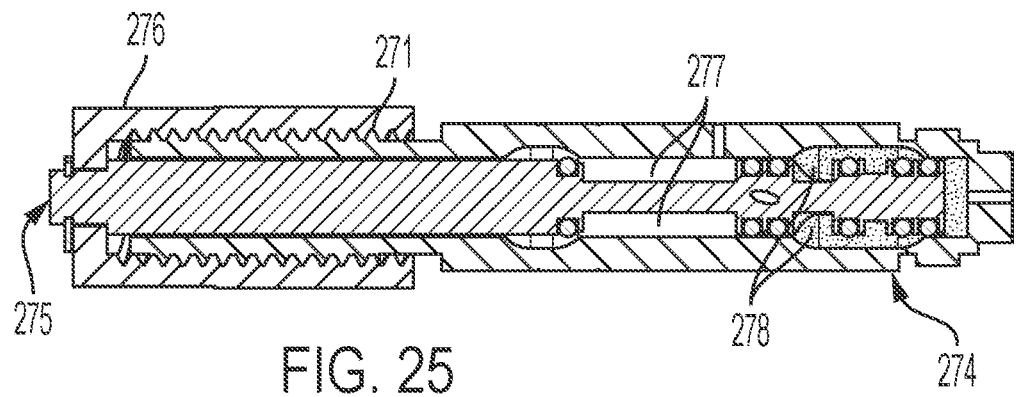

As shown in FIG. 24, ingress rod assembly 275 is further advanced so that sealing members 280 no longer seal lower ingress bypass 283 from sample chamber 279. In this position, lower ingress bypass 283 provides fluid communication between sample chamber 279 and piston chamber 157, which was previously placed under vacuum. Accordingly, the defined volume of sample material contained in sample chamber 279 is drawn into piston chamber 157. As ingress rod assembly 275 is further advanced to the position shown in FIG. 25, lower dilution chamber 278 (and upper dilution chamber 277 via dilution channel 281) are placed in fluid communication with piston chamber 157 via lower ingress bypass 283. Accordingly, the defined volume of dilution fluid contained within lower dilution chamber 278 and upper dilution chamber 277 is drawn into piston chamber 157, which was previously placed under vacuum. The prior contents of upper and lower dilution chambers 277 and 278 and sample chamber 279 are therefore combined to form a biological sample fluid mixture in piston chamber 157. The upper ingress bypass 282 is now positioned over the last sealing member 280 of ingress rod assembly 275, thereby allowing atmospheric air to be in fluid communication with the upper dilution chamber 278 (and by virtue of the dilution channel 281, the lower dilution chamber 278). This permits any residual vacuum in piston chamber 157 to draw in the remaining fluid present, filling piston chamber 157 with the correct volume (defined by the dimensions of piston chamber 157) and at the correct atmospheric pressure (by virtue of the communication of the upper ingress bypass 282 to atmospheric pressure).

Figure 26:
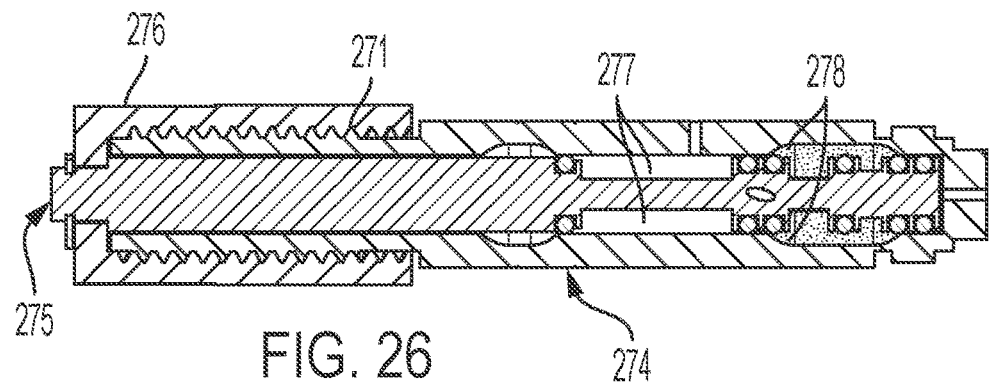

Ingress rod assembly 275 can then be further advanced to the position shown in FIG. 26 (including in whole or in part by the residual vacuum in piston chamber 157), so that sealing members 280 (or, optionally an O-ring that may be present at the interface between the face of the ingress rod assembly 275 and the inner wall of the ingress housing 274, not shown for clarity) seal lower ingress bypass 283. Piston chamber 157 is now sealed and no longer in fluid communication with lower dilution chamber 278, upper dilution chamber 277 or ample chamber 279. The biological sample fluid mixture in piston chamber 157 can now replicated and analyzed, as described in further detail below.

The sample ingress configuration provided by apparatus 200 provides numerous operational advantages. For example, ingress rod assembly 275 comprises sample chamber 279 and dilution chambers 277 and 278, each of which are a known volume based on the configuration of sealing members 280, ingress housing 274 and piston chamber 157. The upper and lower ingress dilution chambers 277 and 278 contain dilution fluid in a desired ratio to the desired biological sample size based on the volume of sample chamber 279. In one particular embodiment, the sample size is set at 50 µL volume of sample chamber 279, but other biological sample sizes such as 1 µL, 5 µL, 10 µL, 15 µL, 20 µL, 25 µL, 30 µL, 35 µL, 40 µL, 45 µL, are possible. In addition, higher volume samples may be used where sample target concentration is low or increased sensitivity is desired (for example 100 µL, 250 µL, 500 µL, 1 mL or more). This can be optionally coupled with methods of concentration as are commonly used in the art. In practice, the lower bound of the biological sample size is set by the concentration of the particular analyte of interest (e.g. the detection limit) such that the minimum number of targets present in the sample corresponds to at least the lower limit of sensitivity of the assay employed (e.g. the number of copies detectable by the amplification, lysis, or detection technology selected for the particular embodiment). This lower bound volume should also take into account any portions of the embodiment where the diluent-sample mixture will reside which are outside of the amplification or detection portions of the reaction. For example in this embodiment, the amplification portion would be bounded on the first end by the face of the rod assembly, so that the volume of the communication to the amplification portion would be included in the amplification portion of the reaction, but cavities between the ingress housing and the ingress rod assembly or plunger elements would be outside of the amplification portion.

Of note, the use of vacuum or partial vacuum within the housing serves to minimize non-reacting diluent-sample mixture fluid by drawing such mixture into the amplification portion once that fluid is in communication with the vacuum (for example, after breaching a seal or movement of the ingress rod assembly) as does the sequence of excess diluent chasing the diluent-sample mixture towards the amplification portion. In some embodiments, the movement of ingress rod assembly 275 within ingress housing 274 serves to collect the raw biological sample, define the volume of that sample used for the amplification chemistry, mix the sample with dilution fluid, and seal the pressure vessel. In some embodiments the pressure vessel can maintain a pressure of 1, 2, 3, 4, 5 or more atmospheres above baseline pressure. In some embodiments, the structural components are made from polymer. In some embodiments that polymer is injection molded.

In this particular embodiment, portions of ingress housing 274 and piston chamber 157 are evacuated, forming a vacuum or partial vacuum (referred to interchangeably herein). To facilitate longer-term storage of apparatus 200, one or more seals may be incorporated to maintain the vacuum. The seal can be made of a polymer (including hot bar sealing), film, wax, fluid, or other means and may be breached via mechanical (e.g. lancets), heat, electrical, kinetic, vibratory or other means. Separate seals (including various types of seal combinations) may be used for multiple portions of apparatus 200 as desired, for example at the junction between the ingress housing 274 and piston chamber 157, between ingress sample chamber 279 and the adjacent chambers (in this particular embodiment, dilution chambers 277 and 278 and piston chamber 157.

In this embodiment, a vacuum also is present in ingress sample chamber 279. As ingress rod assembly 275 is advanced within the ingress housing 274, sample port 155 aligns with the evacuated ingress sample chamber 279, drawing the biological sample 170 into the ingress sample chamber in a specified volume which corresponds to the product of the volume of that chamber and the percent vacuum present.

Figure 14:
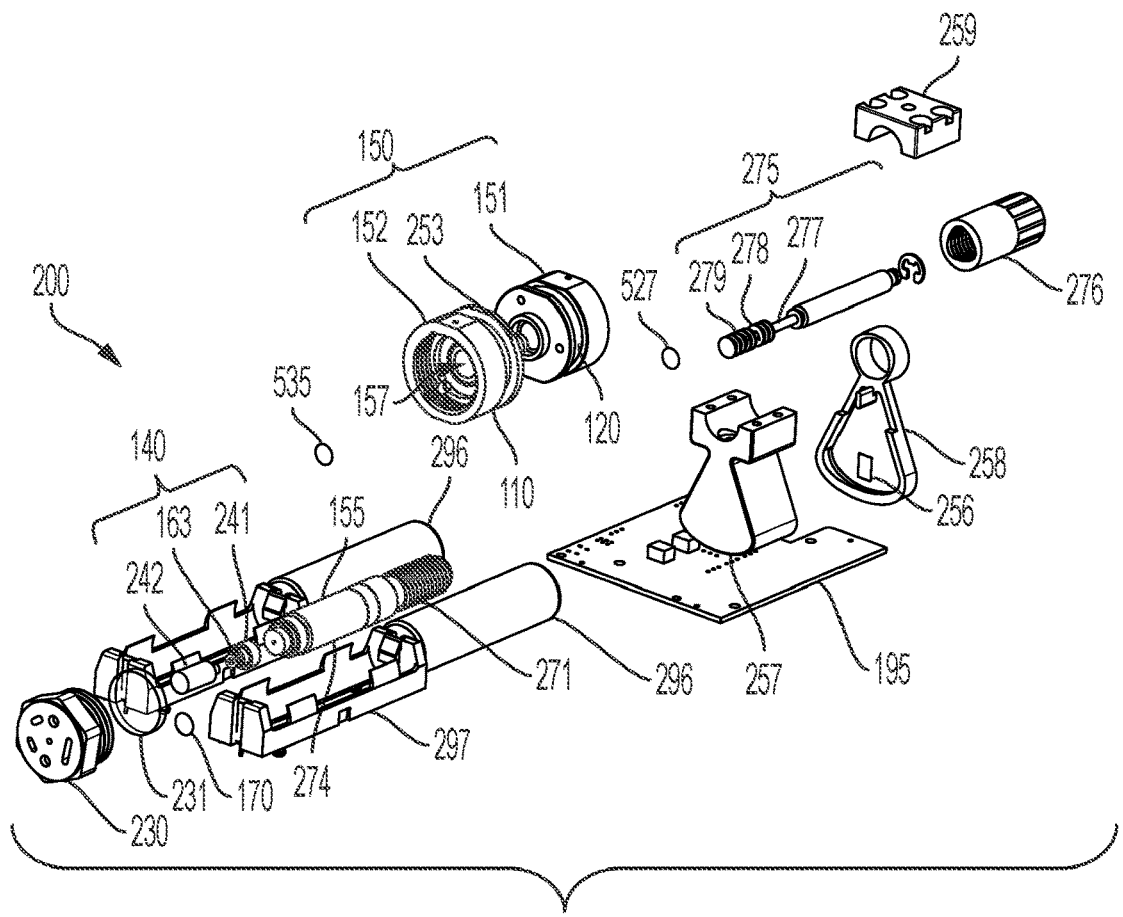
FIG. 14 is a partially exploded perspective view of the embodiment of FIG. 12.

The sample port may communicate with a collection chamber (e.g. spittoon) 257 for expectoration (as is shown in this embodiment) or may use swabs (including flocculated swabs), absorbent or wicking strips, dip sticks, stylus, capillaries, drops, tissue samples, vial, tube, cup, needle, agar, or other sample collection means. The device may optionally include a collection chamber cap 258 and collection chamber back 259 as shown in FIG. 14.

As ingress rod assembly 275 continues to advance within ingress housing 274, the ingress sample chamber 279 establishes communication with the lower ingress bypass 283. The lower ingress bypass 283 is at that point in communication with the amplification portion, which also contains a vacuum or partial vacuum. The effect is to draw a portion of the biological sample 170 which was present in the ingress sample chamber 279 towards the piston chamber 157, where amplification and detection functions can be performed. Continued advancement of the ingress rod 275 within the ingress housing 274 brings the lower ingress dilution chamber 278 in communication with the lower ingress bypass 283 as well as the ingress sample chamber 279. The vacuum in the amplification portion draws remaining biological sample 170 from the ingress sample chamber 279 as well as an amount of the diluent from ingress dilution chambers that equals the product of the volume of the amplification portion and the percentage vacuum of the amplification portion, less any volume occupied by the contents of the amplification portion, which may include without limitation, the piston 140, buffers 172, reagents 173, reaction fluids or reaction mixtures, seals, and other structural elements including asperities or discontinuities which tend to induce turbulence and mixing of the contents.

As previously mentioned, in some embodiments, dilution channel 281 forms a communication between the upper ingress dilution chamber 277 and the lower ingress dilution chamber 278. The communication between ambient atmospheric pressure and the upper ingress dilution chamber 277 is established by the upper ingress bypass 282 which (as the ingress rod assembly 275 advances relative to the ingress housing 274) allows outside atmosphere to chase the fluid column of the diluent into the upper ingress dilution chamber 277. In this way, a single linear movement of the ingress rod assembly 275 relative to the ingress housing 274 accepts a variable amount of raw biological sample (but greater than the minimum biological sample size desired and set by the ingress sample chamber 279) and by means of its action incorporates a predetermined volume of biological sample, mixing that in a predetermined ratio with diluent, and transfers that mixture into the predetermined volume of the amplification portion. The use of vacuum or partial vacuum serves to minimize the gas-phase fluid present in the amplification chamber, including air.

While one particular embodiment is shown, the advancement of the ingress rod assembly 275 relative to the ingress housing 274 can be accomplished in a variety of modes. The current embodiment incorporates a threaded coupling, but various mechanisms and methods can be used to introduce a sample into the chamber used for amplification and detection. For example certain embodiments may include sliders, camshafts, gears of varying ratios, screws of varying ratios, springs, including captured springs as well as compression, extension, leaf, conical, disc, torsion and constant force springs, vacuum assisted or vacuum-powered advancement, manual power, and others that will be readily apparent to the practitioner can be used as well. In some embodiments, the reaction chamber where amplification and detection occurs is capable of containing 0.5 atm, 1 atm, 1.5 atm, 2 atm, 2.5 atm, 3 atm, 4 atm, 5 atm, or more above gauge pressure. In embodiments which use vacuum, or produce a vacuum by virtue of venting gas during heating, the reaction chamber is capable of function at 10%, 25%, 50%, 75%, 85%, 90%, 95%, 99% or greater vacuum. In certain other embodiments, the pressure vessel is comprised of polymers. In other embodiments, the pressure vessel is comprised of metals. In certain other embodiments, the pressure vessel is comprised of metals and polymers.

In certain embodiments, apparatus 200 can detect the presence of a sample in collection chamber 257 via a sensor 256 (e.g. through electrical or optical detection) and provide for automated ingress of a portion of the sample into sample chamber 279 and ultimately to piston chamber 157.

Amplification/Replication

After the contents of sample chamber 279 and dilution chambers 277 and 278 have been transferred to piston chamber 157, apparatus 200 can be operated to amplify (e.g. replicate) and detect analytes of interest in the prepared sample mixture. In certain embodiments, the amplification/replication of the contents of piston chamber 157 can be performed via a polymerase chain reaction (PCR) reagents or reverse transcriptase polymerase chain reaction (RT-PCR) which utilize thermal cycling.

As used herein, the term PCR may be used when describing the amplification action of the invention, but the practitioner will understand that such amplification techniques include those that are not strictly polymerase chain reaction, including isothermal amplification techniques, as well as those that may utilize one or more of various types of PCR, such as polymerase chain reaction (PCR) reagents, such as reagents for reverse transcriptase polymerase chain reaction (RT-PCR), multiplex PCR, nested PCR, asymmetric PCR, hot-start PCR, methylation-specific PCR, allele-specific PCR, assembly PCR, convective PCR, dial-out PCR, digital PCR, helicase-dependent amplification, in silico PCR, intersequence-specific PCR, inverse PCR, ligation-mediated PCR, miniprimer PCR, multiplex ligation-dependent probe amplification, nanoparticle-assisted PCR, overlap-extension PCR, PAN-AC, RNA H-dependent PCR, single specific primer PCR, solid phase PCR, suicide PCR, thermal asymmetric interlaced PCR, isothermal PCR, touchdown PCR, universal fast walking PCR, extreme PCR, photonic PCR, cold PCR, and heat pulse extension PCR.

Nested PCR may be used to reduce the contaminations in products due to the amplification of unexpected primer binding sites. Two sets of primers are used in two successive PCR runs, the second set intended to amplify a secondary target within the first run product. Inverse PCR may be used to allow PCR when only one internal sequence is known, such as to identify flanking sequences to various genomic inserts. This can involve a series of digestion and self-ligation before cutting by an endonuclease, resulting in known sequences at either end of the unknown sequence. (Rahman et al., *AKWC J,* 4(1): 30-36, 2013). RT-PCR may be used to amplify, isolate or identify a known sequence form a cell or tissues RNA library. Asymmetric PCR may be used to preferentially amplify one strand of the original DNA more the other. PCR may be carried out with a great excess of the primers for the chosen strand. A modification on this process, known as Linear-After-The-Exponential-PCR (LATE-PCR), may use limiting primers with a higher melting temperature (Tm) than the excess primer to maintain reaction efficiency as the limiting primer concentration decreases mid-reaction. Quantitative PCR may be used to rapidly measure the quantity of PCR product (e.g., real-time), thus is an indirect method for quantitatively measuring starting amounts of DNA, cDNA or RNA. Touchdown PCR may be used to reduce nonspecific primer annealing by lowering of annealing temperature between cycles. Allele-specific PCR may be used as a diagnostic or cloning technique based on single nucleotide Polymorphisms (SNPs) (single-base differences in DNA). Hot-start PCR may be used to reduce non-specific amplification during the initial set up stages of the PCR. It may be performed by heating the reaction components to the denaturation temperature (e.g., 95° C.) before adding the polymerase or by the inclusion of a bound inhibitor to a thermostable polymerase. Inverse PCR may be used to identify the flanking sequences around genomic inserts. It can involve a series of DNA digestions and self-ligation, resulting in known sequences at either end of the unknown sequence. Ligation-mediated PCR may use small DNA linkers ligated to the DNA of interest and multiple primers annealing to the DNA linkers; it may be used for DNA sequencing, genome walking, and DNA footprinting. Miniprimer PCR may use a thermostable polymerase (S-Tbr) that can extend from short primers as short as 9 or 10 nucleotides. This method permits PCR targeting to smaller primer binding regions, and may be used to amplify conserved DNA sequences, such as the 16S (or eukaryotic 18S) rRNA gene. Methylation-specific PCR (MSP) may be used to detect methylation of CpG islands in genomic DNA. Other types of PCR that may be used include extreme PCR, photonic PCR, cold PCR, nanoparticle PCR, and heat pulse extension PCR.

Embodiments disclosed herein may use one or more temperature zones appropriate for the mode of amplification. For example, a single zone can be employed for isothermal modes, two zones for PCR, or more zones for multiple temperature zones, including, for instance for three temperature PCR, or for specialized purposes, such as initiation or initial dissociation of a binder for lyophilized components, or the action of a reverse transcriptase to permit RT-PCR.

More than three temperature zones, including 4 temperature zones, 5 temperature zones, 6 temperature zones, including 7 temperature zones, 8 temperature zones, 8 temperature zones, or more may be used in other embodiments.

Examples of isothermal amplification methods that are possible in exemplary embodiments include nucleic acid sequence-based amplification (NASBA/3SR), recombinase polymerase amplification (RPA), rolling circle amplification (RCA), loop-mediated isothermal amplification (LAMP), ligase chain reaction (LCR), strand-displacement amplification (SDA), strand invasion-based amplification (SIBA), helicase-dependent amplification (HDA), Toehold-Mediated Isothermal Amplification, nicking enzyme amplification reactions (NEAR), multiple displacement amplification (MDA), transcription mediated amplification, signal mediated amplification of RNA technology, isothermal multiple displacement amplification, single primer isothermal amplification, circular helicase-dependent amplification, cross-priming amplification, and others. These techniques are summarized respectively in the following sources, which are incorporated herein by reference:

Compton, J (1991) Nucleic acid sequence-based amplification. Nature 350: 91-92.

Piepenburg O, Williams C H, Stemple D L, Armes N A (2006) DNA Detection Using Recombination Proteins. PLoS Biology 4: e204.

Fire A, Xu S-Q (1995) Rolling replication of short DNA circles. Proc. Natl Acad. Sci. USA 92:4641-4645.

Notomi T, Okayama H, Masubuchi H, Yonekawa T, Watanabe K, Amino N, Hase T (2000) Loop-mediated isothermal amplification of DNA. Nucleic Acids Res. 28:e63

Barany F (1991) Genetic disease detection and DNA amplification using cloned thermostable ligase. Proc. Natl. Acad. Sci. 88:189-193.

Walker G T, Fraiser M S, Schram J L, Little M C, Nadeau J G, Malinowski D P (1992) Strand displacement amplification—an isothermal, in vitro DNA amplification technique. Nucleic Acids Res 20:1691-1696.

Hoser M J, Mansukoski H K, Morrical S W, Eboigbodin K E (2014) Strand Invasion Based Amplification (SIBA®): A Novel Isothermal DNA Amplification Technology Demonstrating High Specificity and Sensitivity for a Single Molecule of Target Analyte. PLOS ONE 9:e112656

Vincent M, Xu Y, Kong H (2004) Helicase-dependent isothermal DNA amplification. EMBO Rep 5:795-800.

Zanoli and Spoto, Isothermal amplification methods for the detection of nucleic acids in microfluidic devices, 3(1): 18-43, 2013.

Additional amplification methods for detecting targets of interest, for example proteins including antibodies, are possible through the use of techniques such as proximity ligation assay (PLA), (described in one form by Weibrecht I, Leuchowius K-J, Clausson C-M, Conze T, Jarvius M, Howell W M, Kamali-Moghaddam M, Söderberg O (2010) Proximity ligation assays: a recent addition to the proteomics toolbox, Expert Review of Proteomics, 7:401-409), incorporated herein by reference.

Heat Sources

The thermal cycling may be accomplished with a variety of different heat sources. While electric current passing through a first heating coil has been described in the embodiments shown, other embodiments may utilize different techniques. For example, in other embodiments, the heat source may use electrical resistance, electromagnetic induction, adiabatic, microwave, radioisotope, sonic, friction, chemical, geothermal, user/body heat, or solar methods of heating. The heat source, if electrically based, may use batteries, electrical outlets, both, or other sources of power, such as a wireless charging source or USB power source, connected to any enabled device, such as a computer, smart phone, tablet, solar cell or photovoltaic cell. In some embodiments, the heating coils may be replaced by conductive polymers by mixing powdered, finely divided, or liquified metals such as aluminum, copper, ferrous metals, or various alloys, including nickel, titanium and others (or other conductors such as graphite or conductive inks) with a polymer in liquid or granule format to produce a conductive first end or second end or both that has a high resistance and can be used as a resistive heater in place of or in addition to heating coils. In other embodiments, the heating coils may contain one or more parallel coils. In some embodiments, these parallel coils may be used for redundancy. In other embodiments, these parallel coils may be used to divide the number of windings needed to achieve a particular resistance.

Thermal Control

The heat source may heat the reaction fluid directly, through a thermal bridge, or may heat a secondary material such as a wax, oil, or aqueous fluid which can transfer heat to the reaction fluid. This transfer may be indirect, or may be admixed with the reaction fluid, expanding the volume. Metal oxides, epoxies, and other compounds can chemically or physically inhibit PCR, or reduce efficiency, and coatings with less reactive materials such as chrome, alternative polymers, or conformal coating can mitigate this inhibition while maintaining other preferential attributes such as thermal conductivity profiles, or physical hardness.

In a similar fashion, the above methods may be used in thermal regulation, including cooling, or modulated heat dissipation. This may employ active or passive methods, such as Peltier, adiabatic, chemical, fans or air circulators, and specific geometries, or environmental exposure control, heat sink exposure, liquid or phase change cooling, nanotubes, or heat pipes.

In some embodiments, the device uses thermocouples or resistance temperature detectors (RTDs) to sense temperature of the device components. In certain embodiments, the device uses thermistors in place of thermocouples or resistance temperature detectors (RTDs) to sense temperature of the device components. Thermistors may be preferred in some embodiments due to their low cost, fast response time and large change in resistance per degree Celsius change. Their use in some embodiments is feasible because of the low absolute accuracy requirements of the device and ability to use relative, not absolute, raw conductive values to calculate temperatures as described elsewhere herein. The devices can be calibrated at the lot level in several modes, avoiding the need to calibrate each device individually. In some embodiments, a linear approximation of the temperature curve can be obtained by calculating the slope of two or more temperature data points. In some embodiments, the relationship may be calculated by 3, 4, 5 or more temperature data points, and the curve may be of higher order than linear function such as a moving average, polynomial, exponential, logarithmic, or other mathematical transformations. In some embodiments, the regression to the curve of the data points can be used to confirm curve fitting by means of a least squares or other appropriate method. In some embodiments, the devices can be raised to predetermined temperatures, for example 25° C., 65° C. and 95° C., as a lot, and the calibration data of the thermistor resistance on each device can be stored in the non-volatile memory of the device. In some embodiments, the thermistor self-calibration software can reside on the device only during the calibration phase. In other embodiments, it may remain beyond the calibration phase. In some embodiments, the degree of variability of calibration within a lot can be 1%, 2%, 3%, 5%, 10% or more. In some embodiments, the $R^2$ linear regression values of the curve fitting can be less than 0.75, 0.8, 0.9, 0.95, or 0.99. Such high variability allows the devices to be manufactured at a lower price point.

Cycle Control

In designing these devices, it is beneficial to minimize the time required for amplification. This may be accomplished through several approaches, including decreasing the cycle number, cycle duration, decreasing inter-cycle dwell time, or optimizing control system logic, including temperature and fluid cycling controls.

Cycle number may be reduced by utilizing a more sensitive reaction, implementing lysis chemistry which yields more complete lysis, better target recovery, less nucleic acid degradation, or better, including preferential, nucleic acid preservation. Tight temperature control aids in decreasing cycle number, allowing decreased temperature ramp times, narrower margins to the working temperature of materials employed, and in turn more complete PCR activity as the actual reaction chamber conditions approach their ideals. In some embodiments, the temperature ramp rate may be less than or equal to 1° C./s, greater than 1° C./s, 2° C./s, 3° C./s, 5° C./s, 10° C./s, 15° C./s, or 20° C./s. In other embodiments, particularly embodiments with reactions less than 50 µL, 25 µL, 15 µL, 10 µL, 5 µL, 3 µL, 1 µL, or less the temperature ramp rate may be greater than 25° C./s, 35° C./s, 50° C./s, 60° C./s, 70° C./s, 80° C./s, 90° C./s, or more. As described elsewhere herein, cycle number may also be decreased by optimizing the algorithm to terminate the amplification early should certain outcomes (such as sufficient resolution between control and experimental values) be obtained. In certain embodiments, temperature ramp time may also be modulated based on the ambient temperature, which may be detected with device sensors. For example, in a case where the ambient temperature is 0° C., the ramp time to increase temperature will be greater than in a case where the ambient temperature is 40° C. Conversely, the time needed to decrease the temperature will be decreased when the ambient temperature is 0° C. and increased when the ambient temperature is 40° C. Methods of compensating for conductive and convective and radiative heat transfer will be readily apparent to the practitioner.

In some embodiments described herein, the device allows the duration of any particular PCR cycle to be variable in length, rather than fixed as is the case in traditional PCR. Because in some embodiments the reaction vessel contains fluorescent or colorimetric probes, and because the design of the device in some embodiments allows detection of those probes to occur in real time during the process of amplification, the status of the amplification reaction can be assessed not only in an inter-cycle fashion as is possible with traditional PCR, but intracycle, where the low latency and design of the detection system allows repeated fluorescence measurements to occur in short intervals on one or more channels, and calculations of the momentary fluorescence, its slope, and the rate of change in its slope can be used to determine the proportion of the PCR half-cycle (involving extension) which is completed or yet to complete (see Rutledge, R. G., (2004) *Nucleic Acids Research*, Vol. 32, No. 22, and Liu, W. and Saint, D. A. (2002) *Validation of a Quantitative Method For Realtime PCR kinetics*. Biochem. Biophys. Res. Commun., 294,347-353, incorporated herein by reference). In some embodiments, the interval of measurement can be less than 5, 10, 15, 20, 25, 30, 40, 50, 75, 100, 150, 200, 300, 500 milliseconds, or greater.

In other embodiments, sigmoidal curve fitting may be used. In some embodiments, the four-parametric sigmoid function $F_c=F_b+F_{max}/(1+e^{-(C-C_{1/2}/k)})$, where $F_c$ is the fluorescence for cycle C, $F_b$ is the baseline fluorescence, $F_{max}$ is the maximum fluorescence measured, and k is the slope, may be used to establish a real time PCR curve without the need for a standard curve. In some embodiments, the PCR can be semi-quantitative or quantitative. In some embodiments, the inter-cycle $\Delta k$ may be used to determine a cut-off point of the transition between the exponential phase and plateau phase (e.g., a transition phase). In some embodiments, the controller 195 can cycle the piston 140 from the first end 151 to the second end 152 once a predetermined point has been reached in relationship to the transition phase. In some embodiments, the controller can use calculations in relation to the inter-cycle changes. In other embodiments, the controller can use calculations in relation to intracycle changes as described elsewhere herein.

Excess dwell time may be reduced by localizing sensors as closely as is feasible to the reaction fluid (for example, no more than 5 mm from the reaction fluid, or more preferably, no more than 4 mm from the reaction fluid, or more preferably, no more than 3 mm from the reaction fluid, or more preferably, no more than 2 mm from the reaction fluid, or more preferably, no more than 1 mm from the reaction fluid), while maintaining as a high thermal gradient to the heat source as possible. This mitigates spurious heat readings and enables faster equilibration of heat cycles. To determine the optimal balance between adequate dwell time for amplification chemistry and minimized cycle duration, dwell time may be iteratively decreased with a repeated, standardized PCR control while observing the PCR output. As an optional step, once the first material decrease in PCR yield is observed (or prior to it, if desired), an algorithm (the design paradigm can be recursive or iterative in nature) may be employed, dividing the temperature delta between the adequate PCR output result time and the decreased time until a delta of preferably less than 5 seconds, but even more preferably less than 3 seconds, 2 seconds, 1 second, or less is observed. In this manner the efficiency of optimizing the temperature approaches a $n(\log_n)$ efficiency, which is preferred over the linear or haphazard methods of optimization.

Cycle duration can be minimized by increasing heat transfer rates between the heat source(s) and the reaction fluid in several ways. Increasing the ratio of the heating surface area to reaction fluid volume is preferential, with a ratio of (3/radius) of the reaction fluid chamber serving as a floor and ratios of 4, 5, 6, 7, 8, 9, 10, 15, 20 or more of the surface area to the mean distance to the center of the reaction fluid chamber from the edge of the chamber in some embodiments, and can be accomplished by decreasing the reaction volume, increasing the surface area of the heating surface, or flattening one or two dimensions of the three dimensional form (or a combination of such alterations). Decreasing reaction volume is advantageous because it decreases the reagent costs required per assay, and correlates with smaller device geometries, which in turn decrease cost, and the distance of heat travel. The volume may be decreased by concentration of the sample fluid (for example by use of chaotropic salts such as in the Boom method—see R. Boom et al., J. Clin. Microbiology, March 1990, incorporated herein by reference) or through many standard nucleic acid concentration techniques which will be apparent to the practitioner. Decrease of sample fluid volume without concentration, although simpler from an implementation standpoint, may affect sensitivity in some samples, and may be applied where the detection limit of the analyte supports the clinically or experimentally relevant volume reduction of the sample. Additionally, decreasing the proportion of sample fluid ultimately present in the reaction fluid may reduce the inhibitory effect of PCR inhibitors inherent to sample types, such as hemoglobin in blood, or phenolic compounds in plants as described in the section describing the ratios of diluent to sample.

A larger surface area of the heating surface can be achieved in a piston-based device by increasing the diameter of the heat contact disc(s), decreasing the linear distance from the heating surface to the most distant aspect of the fluid, or altering the geometry of the heat transfer surfaces, for example by extending the heating element to encircle the reaction fluid along the axis of the piston, extending heating elements into the reaction fluid (either directly or by thermal transfer) with end or lateral fins, and when employing a design where the piston and chamber are in direct contact with the reaction fluid, it is preferred to accommodate those projections with an inverse structure between the piston end and the chamber end, such that any projections or asperities interdigitate with each other to minimize dead-space as discussed elsewhere herein. The surface area may also be increased by modifying the surface area in various ways designed to cause such increase, for example, by including micropores, microgrooves, or nanostructures.

As used herein, "dead-space" or "dead space" in the context of a reaction means the portion of reaction fluid in the reaction chamber which is not at ideal temperature for amplification during device operation. Dead space may be caused by manufacturing tolerances (including the smoothness of surfaces and the gaps between them), fluid travel paths which result in separation from heating sources, fluid which is adherent to reaction chamber surfaces, or geometries which prohibit the adequate transfer of heat to fluid during the cycle. In certain embodiments, the effect of dead space on reaction efficiencies can be significant. Accordingly, when designing the geometry of a reciprocating piston-based amplification chamber, minimization of dead space as a percentage of total reaction fluid volume can be pursued as follows.

Total potential dead space can first be minimized by decreasing the peripheral or circumferential tolerance between the piston and chamber wall (or corresponding endcap side wall in an embodiment which does not utilize a distinct chamber). In certain embodiments, the lower bound of this tolerance is reached and optimization is complete when piston movement from one end of the stroke to the other increases to a range above about 3 to 5 seconds, though as discussed later, preferably less than 2 seconds, or 1 second. A specific embodiment includes a capillary to facilitate fluid movement between one end of the piston and the other without passing through the circumferential space (whether tolerance space, or designed grooves or flattening in the piston/chamber junction). The amount of dead space introduced by the capillary (with cumulative diameters in some embodiments less than 3 mm, 2 mm, or below 1.5 mm, 1 mm, 0.7 mm or 0.5 mm) is less than that required by circumferential dead space to achieve the same stroke speed. Additionally, with respect to stroke speed, a single capillary can be desired over multiple capillaries of equivalent volume, or when the viscosity of the reaction fluid is above 0.9 cP at the lowest allowable environmental temperature, or above 0.5 cP, 0.4 cP, or 0.3 cP at operating temperature. Detection As previously discussed, apparatus 200 can be operated to amplify the contents of piston chamber 157. During the amplification process, apparatus 200 can also be operated to detect analytes of interest in the prepared sample mixture without transferring or conveying the prepared sample mixture from piston chamber 157. Accordingly, apparatus 200 can be operated to both amplify contents of a sample and detect analytes within the sample in the same location (e.g. piston chamber 157) without the need to convey the sample to a different location (i.e. amplitection).

Figure 27:
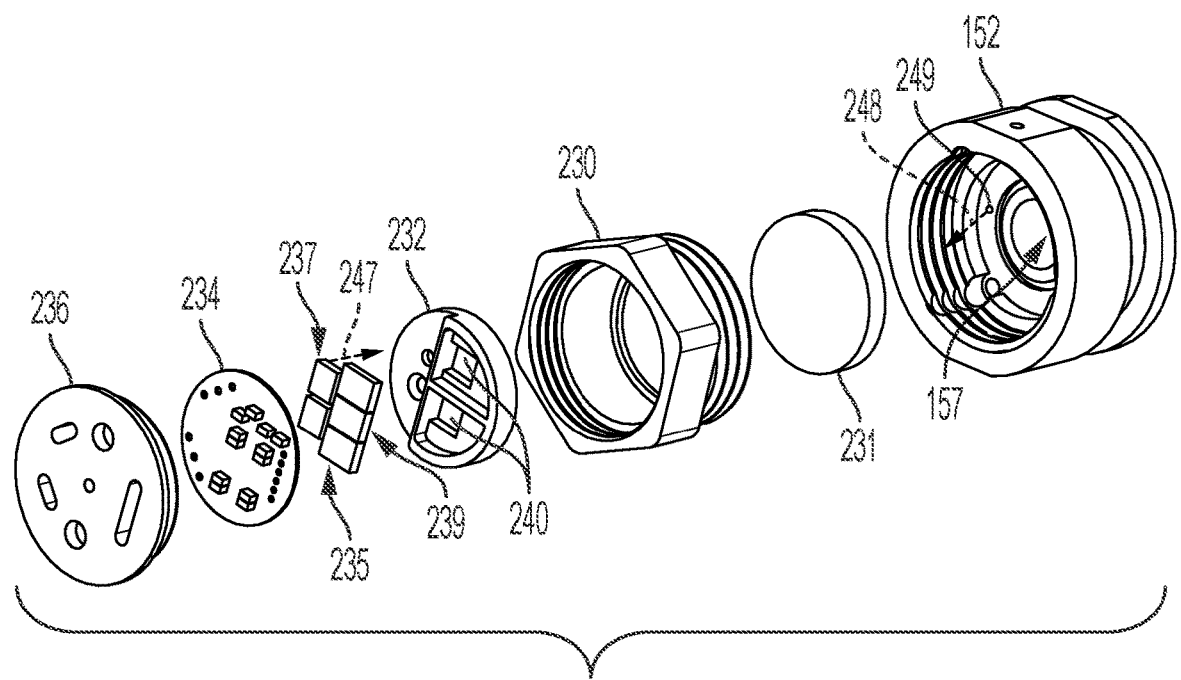
FIG. 27 is an exploded view of components used in sample detection in the embodiment of FIG. 12.

Referring now to FIG. 27, an exploded view of a detection cap assembly 250 is shown along with the second end 152 where it is coupled. In the embodiment shown, detection cap assembly 250 comprises an end plate 231 to separate the contents of piston chamber 157 from electronic illumination and detection components of apparatus 200. In certain embodiments, end plate 231 may be permissive to one or more ranges of wavelength, for instance transparent to visible light.

End plate 231 may be mounted within a bezel 230 which can be threadably coupled to second end 152 of housing 150. Detection cap assembly 250 may further comprise a bezel cap 236 which can be threadably coupled to bezel 230 such that light guard 232 and a detection controller 234 are located between end plate 231 and bezel cap 236.

In some embodiments, apparatus 200 may utilize a detection method that incorporates fluorescence probes to identify specific analytes. In particular examples, such probes may exhibit one or more absorption maximums and have one or more emission maximums. In the embodiment shown, detection controller 234 incorporates one or more light sources 237, one or more detectors 235, zero or more (optional) emitter source photodetectors 239, and one or more filters 240. In specific embodiments, light sources 237 may comprise electroluminescent lights such as light-emitting diodes (LEDs), organic light-emitting diodes (OLEDs), polymer light-emitting diodes (PLEDs), and/or high-power light-emitting diodes (HP-LEDs), or incandescent, fluorescent, high intensity discharge (HID), halogen, chemiluminescent, metal halide, combustion-based, nuclear-based, sunlight, radioluminescent, thermoluminescent, or phosphorescent light sources, among others, and detectors 235 may comprise photodiodes, photometers or other suitable light detectors. In some embodiments, the filters are bandpass filters, and in some embodiments, these bandpass filters may be short or long pass filters. These short and long pass filters may be arranged such that emission and excitation maxima of interest are able to be discerned during simultaneous activation of the illumination sources. In other embodiments, filters, light sources, and detectors will be selected to accommodate a plurality of channels, for example, 2, 3, 5, 6, 7, 8, 9, 10, 11, 12, 13, 14, 15, 16, 17, 18, 19, 20 or more channels, as will be familiar to a practitioner skilled in the art.

During operation, detection controller 234 can illuminate the contents of piston chamber 157 via the one or more light sources 237 emitting light 247. A response 248 resulting from the illumination of the contents of piston chamber 157 can then be detected by the one or more detectors 235. In particular embodiments response 248 may be detected from an analyte 249 that is bound to a surface of piston chamber 157. Light 247 follows a light path that extends from light source 237 to piston chamber 157 without the use of components configured to redirect the light path (e.g. without the use of lenses or mirrors). In addition, response 248 follows a response path that extends from analyte 249 to piston chamber 157 without the use of components configured to redirect the light path (e.g. without the use of lenses or mirrors). For purposes of clarity, the respective paths of light 247 and response 248 to and from piston chamber 157 are not labeled with reference numbers.

If the detection method employs fluorescence, a material can be selected which does not exhibit autofluorescence at the emission or absorption wavelengths used in the detection module (e.g. preferably 400-700 nm, for example, about 485 nm), which may be ascertained during the design phase by performing an amplification reaction with and without the presence of the polymer and comparing the fluorescence visible on a gel, where the background fluorescence of the material contributes preferably less than 10%, but more preferably less than 5%, 3%, 2%, 1% or less of the signal of the positive control.

Additionally, for fluorescence detection or methods which rely on light or electromagnetic radiation with one or more light sources/illuminators and one or more detectors, one embodiment is to use materials which have lower reflectivity in the pertinent wavelengths to increase the signal to noise ratio by decreasing the reflection (radiance) of illumination light. In other embodiments, the use of higher reflectivity materials permits a higher amount of signal to be captured by the photodetector. As discussed herein, either may be a suitable optimization technique depending on the absolute and relative signal-to-noise ratio (SNR) levels.

Figure 28:
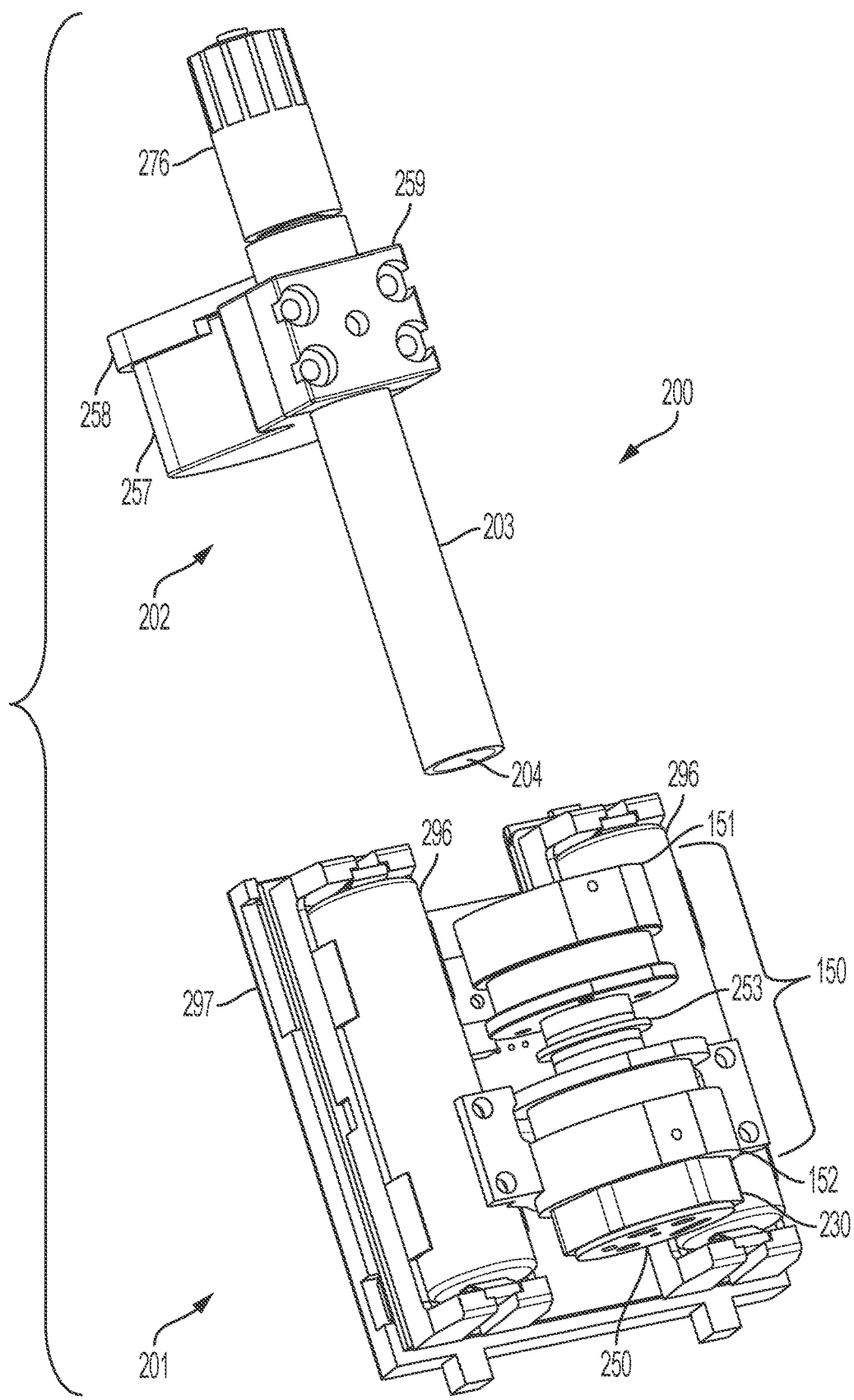
FIG. 28 is an exploded view of the embodiment of FIG. 12 in a base-cartridge configuration.
Figure 29:
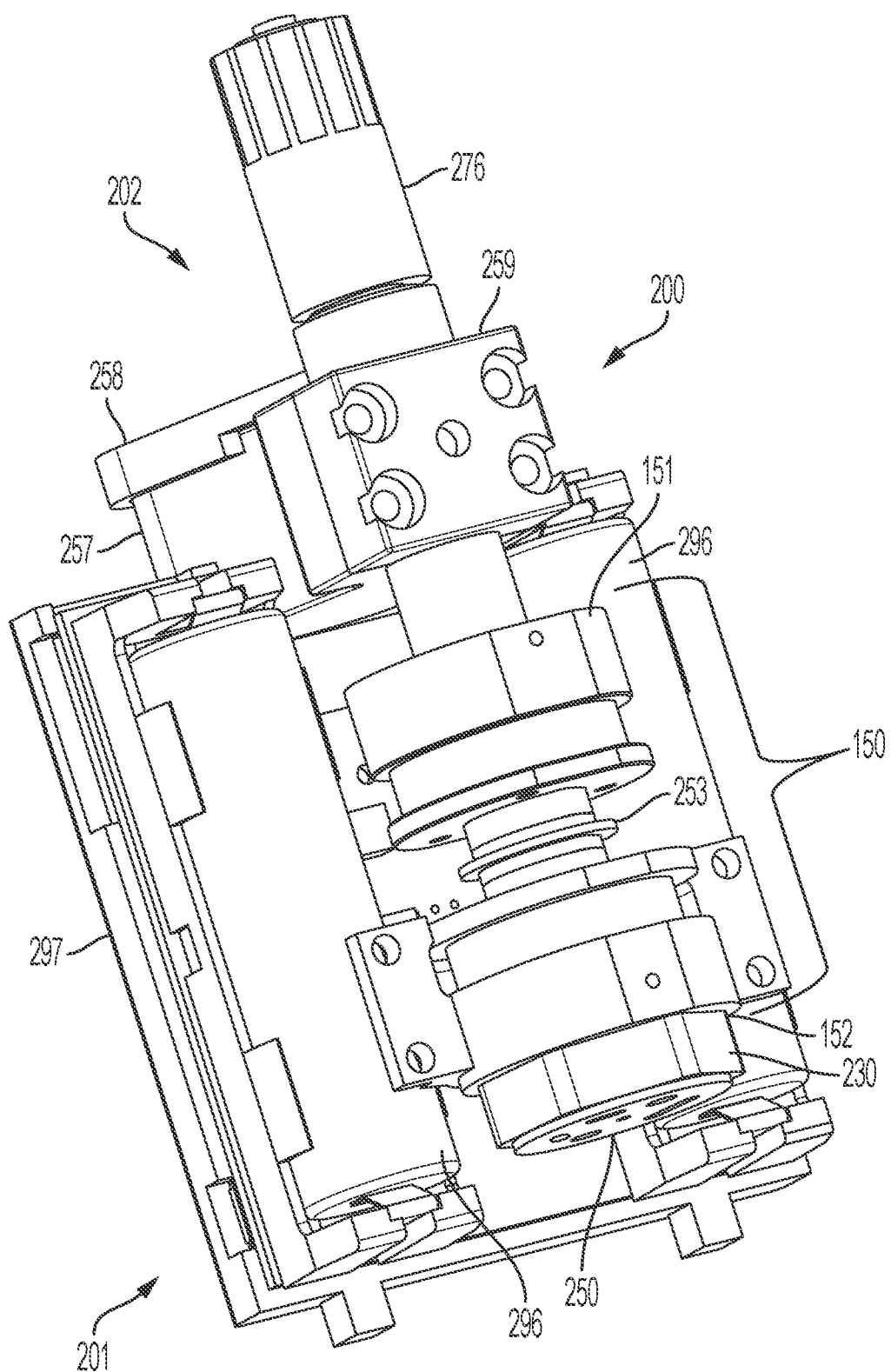
FIG. 29 is an assembled view of the embodiment of FIG. 29.

Referring now to FIGS. 28-29, in certain embodiments, apparatus 200 may be configured as a base and cartridge assembly. In the illustrated embodiment, apparatus 200 comprises a base 201 and cartridge 202. In FIG. 28, cartridge 202 has not yet been inserted into base 201, while FIG. 29 shows cartridge 201 inserted into base 201. In certain embodiments, cartridge 202 can be specifically configured for the detection of particular target analytes (e.g. cartridge 202 may comprise specific reagents suited for the amplification and detection of a particular analyte). Accordingly, a single base 201 and multiple cartridges 202 may be provided in a kit to provide for detection of various different analytes.

In this embodiment, sample ingress, amplification and detection reagents are contained within a chamber 203, which can comprise an ingress rod assembly and housing similar to the embodiment shown in previously-described embodiments. Chamber 203 comprises an end plate 204, which may be permissive to one or more ranges of wavelength, including for instance, transparent to visible light. Cartridge 202 can be inserted into base 201 such that chamber 203 is located within housing 150 and end plate 204 is proximal to detection cap assembly 250. Accordingly, detection can be performed in a manner equivalent to other embodiments disclosed herein.

In the embodiment shown in FIG. 29, base 201 may be reusable, while cartridge 202 may be disposable. Accordingly, base 201 can be used for multiple analyses, while cartridge 202 may be disposed of after a single use, including multiplexed or paraplexed use. During use, the sample and amplification fluids are contained within chamber 203 of cartridge 201, which can eliminate the need to decontaminate or otherwise prepare base 201 for multiple uses. The overall costs for operation of apparatus 200 may therefore be reduced by allowing multiple uses of the components in cartridge 201.

Inter-Cycle Detection Method

Current generation PCR devices which perform automated detection use a variety of techniques, often relying on a prior understanding of the amplification efficiency and the comparison of two curves (an experimental and standard curve).

An alternative to this mode is to use curve-fitting techniques where amplification efficiency does not need to be known beforehand, such as 4-factor parametric curve fitting. Typically, these techniques rely on radiometrically calibrated optical systems to allow for accurate interpretation of PCR amplification results.

To detect PCR products with a device that does not rely on absolute (radiometrically) calibrated values as a basis for detection and is able to detect fluorescence without advance knowledge of the amplification efficiency of the particular sample and reaction, one method that can be applied is to compare the relative baseline of the initial PCR cycles during the early ground phase with a sliding window of fluorescence (or other) signal values to detect the linear phase of a sigmoidal curve and the late, asymptotic phase of the curve.

Self-heating of light sources and other electronic components normally make such a comparison impractical because of the thermal noise present, which imparts a variable slope during the phase when a baseline is being established, but if the thermal noise is adequately controlled (in some embodiments by means of common heatsinking or heat-straps, e.g., by a copper or aluminum bond between the second end 152 and the components of the detection controller 234), the variability of such a slope can be eliminated or mitigated to the extent that it does not interfere with detection.

One embodiment of this inter-cycle detection using relative baselines that does not rely on radiometric optical system calibration and is robust to thermal noise is as follows. First, a baseline is established while the PCR reaction is in the initial cycles, prior to the exponential inflection between the ground phase and the linear phase of the sigmoidal curve associated with detectable PCR amplification. In some embodiments, the baseline may have a slope that is non-zero, and a correction factor may be applied (for example, using linear regression) to transform the data to approximate a flat (zero slope) baseline. The number of baseline values can be as few as 2, but may include 3, 4, 5, 6, 7, 8, 9, 10, 11, 12, 13, 14, 15, 16, 17, 18, 19, 20 or more values. The sample average and variance are calculated for the baseline. Of note, in some embodiments the number of baseline values included in the baseline changes the degrees of freedom and hence the confidence values for the statistical test selected, so for these embodiments, either a math library with functions necessary to calculate the statistic should be included, or if look-up tables are used in lieu of such a math library, appropriate look-up values (including approximated values) for each allowed number of baseline values should be included. In some embodiments, the number of baseline value tables (or columns) is one. In other embodiments the number of such lookup tables (or columns) corresponds to the number of sizes of allowed baseline value sets.

Second, a sliding average window is established. This sliding average window may include as few as 2 values, or 3, 4, 5, 6, 7, 8, 9, 10, 11, 12, 13, 14, 15, 16, 17, 18, 19, 20 or more values. Third, once the average of the sliding window exceeds the average of the baseline, at the same point of each PCR cycle (in one embodiment at the conclusion of the cold cycle), a statistical test (see NIST/SEMATECH e-Handbook of Statistical Methods, October, 2013 update edition, available at http://itl.nist.gov/div898/handbook/, incorporated herein by reference) is performed to establish a confidence interval that the difference between the baseline and the sliding window is not due to chance.

In one embodiment, the statistical test is a two-sample t-test, where the $t^2$ value is calculated as:

$$t^2 = \frac{(\overline{W} - \overline{B})^2}{\left(\dfrac{\text{Var}_W}{n_W} + \dfrac{\text{Var}_B}{n_B}\right)}$$

Where:
$t^2 = t^2$ statistical value
$\overline{W}$=Average of the selected sliding window
$\overline{B}$=Average of the selected baseline
$\text{Var}_W$=Variance of the selected sliding window
$\text{Var}_B$=Variance of the selected baseline
$n_W$=number of selected values of the sliding window
$n_B$=number of selected values of the baseline In one embodiment, the two-sample, one-tail t-test uses a lookup table to determine confidence for the t-distribution, for example using 8 degrees of freedom,

| Index | $t^2$ | t | Confidence |
|---|---|---|---|
| 1 | 0 | 0 | 0.50000 |
| 2 | 1 | 1 | 0.8267 |
| 3 | 2 | 1.4142 | 0.9025 |
| 4 | 3 | 1.73205 | 0.9392 |
| 5 | 4 | 2 | 0.9597 |
| 6 | 8 | 2.8284 | 0.9889 |
| 7 | 20 | 4.4721 | 0.999 |
| 8 | 42 | 6.4807 | 0.9999 |
| 9 | 80 | 8.9443 | 0.99999 |
| 10 | 147 | 12.1244 | 0.999999 |

In some embodiments, the detection result is based on a lookup of the $t^2$ value, which simplifies calculations and depending on the size of the memory of the apparatus and the size of the math libraries needed to accommodate more complex functions, allows for the use of electronic components which incorporate smaller memory capacities (in some cases less than 4 MB, 2 MB, 1 MB, 512 kB, 256 kB, 128 kB, 64 kB, 48 kB, 36 kB, 24 kB, 18 kB, 16 kB, 12 kB, 10 kB, 8 kB, 6 kB, 4 kB, 2 kB or less), decreasing the cost of construction. In other embodiments, the confidence value is calculated iteratively using math calculations.

In other embodiments, the statistical test is a lack-of-fit test, for example a sum-of-squares analysis. In other embodiments, the statistical test is Bayesian test, for example one based on data from prior device runs and comparing the fit of the current run. In other embodiments, the statistical test is a non-parametric statistical test, such as a sign test, which does not rely on prior assumptions about the data distribution and for example, uses the variance of the mean to reject the null hypothesis once the deviation is greater than expected during data collection.

In general, designing the system to operate without the need for higher mathematics such as trigonometry, exponents, integration, etc. is advantageous, as such libraries often require 1, 1.5, 2 or more kilobytes (kB) of memory. In a specific embodiment, the exclusive use of fixed-point math to the exclusion of floating-point math decreases the complexity of calculations such that such math libraries are not used, decreasing code size by about 2 kB. Although this a trivial sum in a benchtop or otherwise complex PCR machine, when optimizing for small code size (which is important to achieve a low-cost basis for components), particularly in a small, portable, or disposable device, reduction of this quantity of memory requirement from a 4 MB, 2 MB, 1 MB, 512 kB, 256 kB, 128 kB, 64 kB, 32 kB, 16 kB, 8 kB, 4 kB, or smaller memory pool is a meaningful reduction. The elimination of these functions may be accomplished in some embodiments by the use of lookup tables for functions (e.g. sqrt, statistics, transformations, etc.) or by constraint to values which are whole number powers of two so that bitwise manipulations may be easily applied. In some embodiments, the use of lookup tables is facilitated by a priori knowledge of the size of the sample set so that (e.g. the degrees of freedom may be known and) calculations may be simplified.

Additionally, to conserve space in some embodiments, approximations may be made for particular operations. For example, to calculate the square root of a number that is not a perfect square, A, one method that may be used is to determine this, using a lookup table (including a hashed lookup table), is as follows:

Step 1: Determine the largest perfect square that is less than A (hereinafter, B);
Step 2: Determine the largest perfect square that is greater than A (hereinafter, C);
Step 3: Calculate the quotient (hereinafter, Q) resulting from (A−B)/(C−B);
Step 4: Add Q to the square root of B to attain the approximate square root of A.

For the purposes of illustration in applying the above process, if it were desirable to approximate the square root of 32, which has a square root of 5.657 (as rounded to three decimal places), then the process would be as follows:

Step 1: The largest perfect square that is less than 32 is 25;
Step 2: The largest perfect square that is greater than 32 is 36;
Step 3: (32−25)/(36−25)=approximately 0.636;
Step 4: the square root of 25+approximately 0.636=approximately 5.636.

Furthermore, in some embodiments, to increase confidence for the validity of the test, additional detection channels, for example control channels, using aforementioned embodiments for detection results can be included as well. In one embodiment, the construction of a Boolean truth table between channels couples detection results in a binary format based on confidence, where a confidence threshold determines success or failure for each channel. For example, suppose a 3-channel system with two controls (C1 and C2) and one sample (S) with a confidence threshold of 0.999 or greater indicating success and otherwise failure for the detection channel. In one embodiment, group the control channels using Boolean algebra for a combined control result C, such that C=C1 AND C2. Compare C against S to create the resultant truth table with four (4) outcomes:

|  | C = SUCCESS | C = FAILURE |
|---|---|---|
| S = SUCCESS | POSITIVE result | ERROR result |
| S = FAILURE | NEGATIVE result | INCONCLUSIVE result |

Additionally, another embodiment utilizes a scoring method based on confidence for each detection result. The overall system result can be characterized based on the combination of scores, creating different ranges for each conclusion. As an example, using the index value of the lookup table for t-distribution for 8 degrees of freedom as a scoring point, a 2-channel test with a control channel (C) and a sample channel (S) would associate the index with respect to the confidence; the combination of scoring points between C and S (for example, an arithmetic difference or sum of indices from a statistical lookup table) would determine the system result with different ranges for different outcomes:

|  | Result |
| --- | --- |
| ≤0 | ERROR |
| 1-4 | NEGATIVE |
| 5-15 | INCONCLUSIVE |
| 16-20 | POSITIVE |

Intracycle Optimization Method

In some embodiments, overall time to statistical detection can be shortened if the rate of amplification within a cycle is non-linear and a first portion of the cycle exhibits a greater than linear gain compared to the remaining portion of the cycle. If a doubling cycle takes n seconds, some reactions could exhibit greater amplification early in the cycle due to thermal characteristics or other intrinsic properties of the reaction such as the concentration or activity of nucleotides, inhibitors, enzymes, etc. The number of cycles to double can be approximated by the time to reach a certain percent, and some reactions could benefit with a reduced cycling time. In some embodiments, the preferred percent corresponds to the point of maximal slope from the start of the PCR cycle. In other embodiments, when for example the rate of change of the nucleic acid concentration differs from the rate of change of detectable fluorophore, the preferred percent is adjusted to compensate for the difference.

For example, if the doubling time is 80 seconds and the reaction reaches 30% of its total fluorescence increase in the first 20 seconds (greater-than-linear, as 20/80 would be expected to produce a 25% increase given linear characteristics), the number of cycles to double if shortened to 20-second cycles would be ln(2)/rate, or approximately 69.3/30=2.3 cycles. At 20 seconds/cycle, this equals approximately 46 seconds for an approximate double, which is 42% faster than 80 seconds. Using this method of fluorescence curve compression, the shortened cycle fluorescence curve could be fitted to appear as a full-cycle curve with application of post-processing gain coefficients. This method may be combined with other embodiments, for example where prior estimates of the doubling time are known, or when they are unknown and early cycles are used to estimate amplification dynamics to pick the preferred percent of the cycle.

In one embodiment, additional optimization can be achieved by analysis of the fluorescence signal intracycle (within the confines of one or more single cycles) without advanced knowledge of the curve dynamics, radiometric calibration of the optical system, or unit-by-unit calibration of the thermal system. Though current generation PCR devices routinely rely on obtaining fluorescence readings for detection at the end of each PCR cycle (inter-cycle), the use of embodiments described herein which permit amplitection (combining the amplification and detection phases into a single process) allows for readings during the course of a single cycle.

This provides a significant improvement in PCR efficiency when analyzing samples of unknown concentration and amplification efficiency. In some embodiments, the improvement can be up to 5%, 10%, 15%, 20%, 25%, 30%, 50% or more. In a particular embodiment, the improvement is 4%. In other embodiments, the improvement is about 26%. It also allows the detection system to automatically compensate for variations in operating environment or device status and further reduces or eliminates the need for calibration. In some embodiments, the apparatus described herein does not require previous assay-specific thermal calibration (e.g. using melt curve analysis on known standard DNA fragments to calibrate the relationship between temperature and fluorescence). Moreover, in some embodiments, detection may be performed using a system which was not optically calibrated using radiometric calibration.

In some embodiments, the electrical signal (for example, analog-digital converter ticks, or ADC ticks) from a photodiode may decrease in response to increasing light on the photodetector, while in other embodiments the electrical signal may increase in response to increased photosignal. For the purposes of clarity, discussed herein is an embodiment where increased light on the photodiode causes a decrease in ticks seen from the ADC (i.e. an inverse relationship), but the methods and structures described herein can be applied to either.

In some embodiments, the photodetector may be characterized to establish a noise floor to determine the number of elements used in statistical calculations. Furthermore, to simplify calculations and ensure high confidence in the sample set relative to the standard deviation, approximations in calculating the minimum number of samples can be given as:

$$n_{min} = \left(\frac{Z * \sigma}{ErrTol}\right)^2$$

Where:

$n_{min}$=minimum number of elements

Z=z-score value corresponding to the desired confidence interval

σ=standard deviation

ErrTol=Error tolerance

In some embodiments, choosing value of 2 for Z ensures a confidence greater than 95%, and choosing ErrTol as a factor of the standard deviation, σ, simplifies the calculations for the minimum number of samples, which is an advantage in cases where processor speed, memory size, or availability of math library functions is limited, for example limited due to cost-constraints.

In some embodiments, a moving average can incorporate an index of n elements, where n is a positive integer greater than or equal to one. In some embodiments, the moving average can be balanced, for example by giving equal weight to each index number (e.g. in a four-index moving average the weight can be [1, 1, 1, 1]/4). In certain embodiments, it is preferred that the sum of the weights equals $2^x$ where x is a whole number (including 0) as this facilitates bitwise calculations. In other embodiments, the moving average can be weighted with a bias, for example with a weight biased towards recency (e.g. in a three-index moving average, the weight can be [5, 2, 1]/8), again with certain embodiments preferring that the sum total equals $2^x$ where x is a whole number (including 0).

In some embodiments, the fluorescent signal is emitted by a dye (e.g. a DNA-binding dye) which displays sensitivity to temperature, such that fluorescence increases intracycle as the temperature of the fluid decreases. In other embodiments, the fluorescent signal is emitted by a probe (e.g. a 5' hydrolysis probe, such as a TaqMan probe, such terms being used interchangeably herein) which displays sensitivity to temperature during the early intracycle, where decreasing temperature decreases bond energy or results in the formation of secondary structures of the probe, leading to a closer approximation between the fluorophore and the quencher, and a resultant initial decrease in fluorescence prior to the initiation of the elongation portion of the cycle, during which the fluorescence begins to increase. In either embodiment, once the temperature of the PCR reagents has decreased enough for elongation to occur, the fluorescence begins to increase (leading to a decrease in the ADC tick values in this embodiment).

In some embodiments, the data may be filtered to exclude outliers using any valid statistical approach. For example, outliers may be designated as 1.5*the Interquartile Range (IQR). In other embodiments, the minimum or maximum values of a set may be removed before the weighted average is calculated. In other embodiments, deviations by greater than a particular percentage of the average weight may be excluded. In some embodiments, the statistical test used (e.g. a sign test) is intrinsically robust to outliers because the magnitude of the difference is not considered and the nature of examining the running average of the most recent data points makes it sensitive to detecting changes (a recency bias).

In some embodiments, the change in slope of the fluorescence values may be used to determine when PCR reactions have reached inflection points of interest, including points where an automatic call may be performed or points where the PCR cycle may be terminated to improve efficiency, speed, or reliability of the reaction. In some embodiments, the following method may be performed to determine if the elongation portion of the PCR cycle has reached a point (e.g. the inflection into the asymptotic portion of the PCR sigmoid curve) where ending the extension period and shifting the piston to move a majority of the reaction fluid to the first end (i.e. the higher temperature side of the thermocycler) to restart another PCR cycle would produce a net faster amplification if applied to one or more cycles of PCR:

First, an n-sized array of fluorescence values, f, is established (where n=1+minimum number of samples) with respect to the standard deviation, confidence, and error tolerance as described herein; for example, choosing a z-value of 2 (corresponding to a confidence greater than 95%) and an error tolerance of standard deviation/sqrt (2), results in a minimum sample size of 8. The array f is a sliding window, keeping the n-most recent values. As n increases in value, the sliding window becomes less susceptible to noise, but the ability to make an early (intracycle) call with respect to the end of the elongation portion of the cycle (as described below) is slowed. In some embodiments, n is 2 or 3. In other embodiments, n is 4, 5, 6, 7, 8, 9, 10, 11, 12, 13, 14, 15, 16, 18, 19, 20, or more. In some embodiments, the fluorescence values off have been filtered to exclude outliers as described herein. In other embodiments, the fluorescence values of f (or the values once outliers have been removed) have been weighted to apply a smoothing function. In some embodiments, the smoothing is a convolution of the fluorescence values on the weighting values. As discussed below, additional fluorescence values are read during the PCR cycle. For clarity, when discussing the addition, selection or manipulation of those values, it is understood that this may also include such functions applied to filtered or smoothed data as well.

Second, within the sliding window, determine when the newest value is the minimum within the array; this, by definition, ensures a downward trending slope across the array.

Third, once the newest member off is the minimum within the sliding window, identify the maximum value within f and its index. Because fluorescence values have fluctuations, choosing the local maximum allows for the greatest inflection point and consequently, the greatest absolute slope calculation. This is the point considered to be the establishment of the exponential phase of PCR. In some embodiments, the sign of the slopes may be encoded using binary bits.

Fourth, an array of slope values, m, is established of size k=n−1 which contains the slopes starting from the local maximum value identified in f. If the local maximum value is not the oldest entry, continue reading fluorescence values and calculating slope values until size k is reached for array m. Array m is a sliding window, keeping the most recent k slopes. When k slopes are calculated, this establishes the minimum baseline set.

Fifth, calculate (and update each time a new fluorescence value is added to the arrays) $m_k=f_{n+1}-f_n$, retaining the newest k slopes in array m. In some embodiments where the time between readings is varied, $m_k=(f_{n+1}-f_n)/(t_{n+1}-t_n)$, where t is the time interval.

Sixth, compare the most recent slope calculation, $m_k$, within the sliding window of array m, and if it is least negative (or most positive) slope within the sliding window, this is the point considered to be the establishment of the asymptotic phase of PCR. In some embodiments which reach this phase, the piston is cycled to direct a majority of the PCR reaction fluid to the other (higher temperature) end of the chamber and the PCR cycle concludes.

Seventh, return to the fifth step to calculate the slope of the next fluorescence value.

In other embodiments, (for instance, when a double-stranded DNA binding dye is used, as the polymerase elongation can lag behind the fluorescence change), an additional period is allotted prior to cycling the piston. In some embodiments, this is a static period and can be 1, 2, 3, 4, 5, 6, 7, 8, 9, 10, 15, 20 seconds or more. In other embodiments, the period is adjusted based on the particular assay conditions. For example, additional time may be allotted if the temperature of the lower temperature end of the chamber is too hot or too cold for optimal PCR extension (in some embodiments 1° C., 2° C., 3° C., 4° C., 5° C., 7° C., 10° C., 12° C., 15° C., 25° C., 35° C., 45° C., or more away from ideal), or may be shortened if the length of the target sequence amplified is less (in some embodiments, in a percentage equal to the change in sequence length above or below 200 bp) or the speed of the polymerase used is increased (in some embodiments, in proportion to the percentage increase or decrease in polymerase speed relative to native Taq polymerase).

Optical Analysis

Current PCR fluorescence detection systems are relatively expensive for several principal reasons: they require collimating lenses and dichroic mirrors, they employ design features for high optical efficiency, they require radiometric calibration, high complexity and a large number of component subsystems along the light path. To produce a low-cost PCR fluorescence detection system, it is preferred to reduce or eliminate each of these elements. As used herein, the term "lens" is used to refer a light accumulator, which can be configured in a number of different manners. For example, a lens may be configured with fiber optic components and/or in a convex, concave, Fresnel, or other suitable configurations for light accumulation.

Lenses and mirrors are not necessary components of constructing a fluorescent detector for PCR if there is sufficient proximity between the emitters and detectors and sufficient light flux generated from the fluorescent probes which reaches the detector. The radiation exchange within an enclosure of diffuse surfaces defines the amount of incident flux on the detector.

Figure 30:
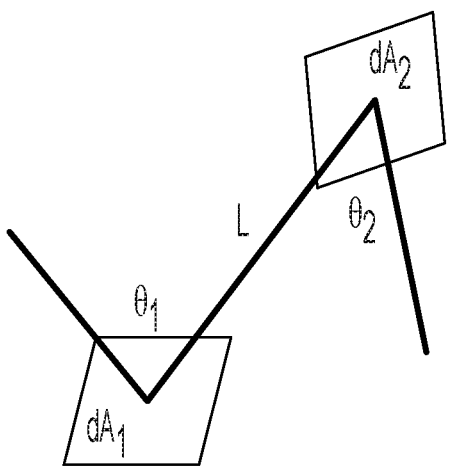
FIG. 30 is a schematic view depicting the exchange of light between any two surfaces within the detection chamber.

As shown in FIG. 30, the exchange of light between any two surfaces within the detection chamber is governed by the following generalized equation:

$$dF_{d1 \to d2} = \frac{\cos(\theta_1)\,\cos(\theta_2)}{\pi L^2} e^{-\alpha L}$$

Where:
L=distance between the two surfaces
α=absorption coefficient of material between the two surfaces*
θ=the angle of incidence of the ray on the surface
The value of α is a summation of absorption of the material by particulates and other contaminates, as well as the absorption contributed by the fluorophore.

Evaluation of this equation is simplified for certain geometric shapes such as a sphere. However, the solution to the equation becomes considerably more complex when applied to complex geometries that may be present within a PCR detection chamber. Instead of numerical evaluation, the incident flux at any given volumetric point within the chamber may be calculated through modelling, using non-sequential ray tracing programs (available commercially, such as TracePro, ASAP, FRED, LightTools, SPEOS, ZEMAX, and others), where parameters such as specific chamber geometry and excitation light distribution intensities can be accurately modelled. In such a model, it is also important to include proper absorption areas, reflectivity of the chamber walls, and diffuse or specular reflection properties, as well as scattering properties of all surfaces.

Figure 31:
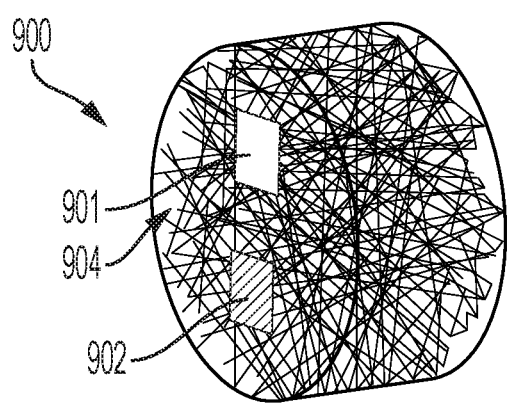
FIG. 31 is a schematic view of non-sequential ray trace modelling of a detection chamber according to an exemplary embodiment of the present disclosure.

FIG. 31 shows non-sequential ray trace modelling of an exemplary detection chamber 900, where the chamber is shown as a gray cylinder, the light emitting device is a white rectangle 901, and the detection photodiode is a hatched rectangle 902. The gray solid lines are individual rays scattering and reflecting within the chamber. In this ray trace example, the interior surfaces of the cylinder are highly reflective. Diffuse Lambertian scattering from the surfaces distributes the excitation light throughout the chamber providing uniform stimulation of the sample.

Reflectivity of the chamber walls serves to recycle the emission light, and as a consequence creates an additional multiplicative factor whereby more emitted light is integrated on the detector than the generalized equation would calculate. Hence the materials and reflectivity of the walls of the chamber can play a significant role in the optical signal power collected by the detector. The multiplicative factor follows the expression:

$$M = \frac{\rho_w}{1 - \rho_w\left[1 - \sum_{i=0}^{n} f_i\right] - \sum_{i=0}^{n} \rho_i f_i}$$

Where:
$\rho_w$=reflectance of the interior surfaces
$\rho_i$=reflectance of the absorbing surfaces
$f_i$=fraction of the absorptive surface area relative to the total area To maximize this multiplicative factor, the reflectivity of chamber surfaces should be as high as the materials used permits (for example, by using surfaces with smooth, reflective finishes with an albedo of at least 0.1, or more preferably 0.2, 0.3, 0.4, 0.5, 0.6, 0.7, 0.8 or higher in the wavelength ranges of interest [typically about 400-600 nm for fluorescence detection embodiments]), and the non-detector absorptive areas minimized, with non-detector absorptive areas constituting less than 50%, 40%, 30%, 20%, 10%, 5%, 4%, 3%, 2%, 1% or less of the enclosure preferred. Further, it is preferred to increase the ratio of the photodetector surface area to the surface area of the non-detector portion of the chamber, in some embodiments with a ratio of 5%, 10%, 15%, 20%, 35%, 50%, 75%, 90%, 95%, or higher. As the volume of a three-dimensional geometric shape decreases, the ratio of surface area to volume will tend to increase (the ratio may also increase if the shape undergoes flattening of at least one aspect at a faster rate than the volume increases). In addition, the ratio of surface area to volume for any detection chamber will increase in proportion to the three orthogonal dimensions, with a sphere in three dimensions being a minimum surface area to volume ratio at any particular volume.

In some embodiments, it is preferred to increase the surface area of the photodetector compared to the volume of the detection chamber, bounded by the sensitivity threshold of the particular photodetector used such that the flux of light reaching the photodiode is sufficient to reach the minimum threshold of light necessary to induce a current from the photodiode that is distinguishable from the dark current and electrical noise and greater than the lower limit of photocurrent linearity. In some embodiments, the photodiode uses Zener, avalanche, or Varicap diodes. In some embodiments, the photodiode uses reversed bias, forward bias, or zero bias current flow. In some embodiments, the minimum threshold of light required to induce detectable current (i.e. the noise-equivalent power) is greater than 0.1 pW/√Hz, 0.5 pW/√Hz, 1 pW/√Hz, 5 pW/√Hz, 10 pW/√Hz, 15 pW/√Hz, 20 pW/√Hz, 25 pW/√Hz, 30 pW/√Hz, or more.

As discussed elsewhere herein, depending on the optimization parameter of interest, signal-to-noise ratio may be improved by either increasing signal, decreasing noise, or both. Dark-colored (e.g. black) surfaces produce a lower noise floor, and so long as smooth-surface materials are used (limiting light baffles in the design as well as decreasing roughness to 3.2 µm, 1.6 µm, 0.8 µm, 0.4 µm, 0.2 µm, 0.1 µm, 0.05 µm, 0.025 µm or less), effective detection may be achieved with dark-colored surfaces. White, undyed, or otherwise reflective materials with increasing albedo produce more signal, and with proper signal to noise differentiation as discussed elsewhere herein, are also effective enclosure materials, with lighter-colored, more reflective materials typically exhibiting a net 2-2.5-fold improved signal-to-noise ratio over dark-colored surfaces for most configurations.

In a PCR fluorescence detector, for practical purposes the light emitted from a fluorophore is emitted in a random direction, so the likelihood of the emission hitting the detector is proportional to the square of the distance from the fluorophore to the detector. As such, the chamber volume should also be kept as small as reasonable to minimize internal surface area, minimize absorption, decrease mean distance to the detector, and hence increase flux which can ultimately reach the detector. For chambers with small volumes (in some embodiments, less than 500 µL, 250 µL, 150 µL, 100 µL, 50 µL, 40 µL, 30 µL, 25 µL, 20 µL, 15 µL, 10 µL, 7.5 µL, 5 µL, 3 µL, 1 µL, or smaller) and high reflectivity (in some embodiments, with albedo ranges of at least 0.1, or more preferably 0.2, 0.3, 0.4, 0.5, 0.6, 0.7, 0.8 or higher in the wavelength ranges of interest [typically about 400-600 nm for fluorescence detection embodiments])), the multiplier effect described above can be significant, providing 2-10-fold, or even greater, increase in optical signal on the detector.

Although in practice, complex systems are often modelled using the method of non-sequential ray tracing described above, integration of the light from the fluorophores by the PCR fluorescence detector can also be numerically evaluated. The intensity of light at the detector plane follows the generalized form below, and a detector chamber may be designed without the use of lenses or mirrors, provided that the irradiance at the detector produces sufficient current in the photodiode such that the portion of photon-induced current from the irradiance on the detector is sufficiently high (e.g. at least 1.5:1, but more preferably 2:1, 3:1, 5:1, 10:1, 50:1, 100:1, 250:1, 500:1, 1000:1 or greater) compared to the dark current (i.e. the baseline current produced from the photodetector in the absence of light, for instance from thermal sources). Specifically, the spectral irradiance at the detector can be calculated as follows:

$$E_d(\lambda) = \int_0^\theta \int_0^r \frac{I_e(\lambda)\rho\Phi\alpha(\lambda)}{\pi r^2} dr d\theta$$

Where:
$E_d$=spectral irradiance at the detector
$I_e$=optical excitation intensity at the fluorophore
$\rho$=fluorophore density
$\Phi$=quantum yield
$\alpha$=absorbance of excitation light
r=distance from the detector to the fluorophore
$\Theta$=half angle field of view of the detector As the optical efficiency of the system (encompassing both the transmission of excitation light to the sample as well as the collection efficiency of the light emitted from the fluorophores) can be calculated (as described below), and having determined the spectral irradiance value either through numeric calculation, via ray tracing or collected experimentally, the parameters of the detector chamber, fluorophore type and concentration may be easily altered without undue experimentation to increase the spectral irradiance of the system to a level which achieves at least a minimally functional signal-to-noise ratio between the photocurrent and dark current (as described above).

The electrical conversion of the emitted signal light in the detector can be calculated by the overlap integral of the spectral responsivity and the detector material with the emission spectrum of the fluorophore as integrated across the wavelength range of the emission spectrum of the fluorophore. Included also are the losses or inefficiencies due to bandpass, long or short pass, or absorptive filters, or other optical and non-optical components in front of the detector. The signal current out of the detector can be calculated using the area of the detector and integrating over the wavelength dependent functions according to:

$$I_s = A_d \int_{\lambda_{min}}^{\lambda_{max}} E_d(\lambda)[R(\lambda)\hat{E}_s(\lambda)(1-L(\lambda))]d\lambda$$

Where:
$I_s$=electrical current out of the detector due to the signal
$A_d$=detector area
R=responsivity of the detector material
$\hat{E}_s$=normalized emission spectrum of the fluorophore
L=optical loss fraction
$E_d$=spectral irradiance at the detector Optical systems, such as those that function in typical PCR fluorescent detection systems, often require high optical efficiency due to the extended light path lengths needed to accommodate components and the use of calibrated modes of detection. The inclusion of collimating lenses, dichroic mirrors and precise alignments of components in these systems typically achieves an optical efficiency related to the transmission of excitation light of greater than 75-80% (with efficiencies of greater than 90-95% possible) and collection efficiencies (calculated as described below) between 0.3% and 3%. The optical efficiency in a system which uses lenses can be calculated by the formula:

$$\eta = \frac{\sin^{-1}(n \sin \theta)^2}{4\pi}$$

Where:
$\eta$=optical efficiency
n=index of refraction
$\theta$=maximum half-angle entering the lens In contrast, certain embodiments of the present disclosure do not include lenses, thereby shortening the light path to less than 2 cm, but more preferably less than 1.5 cm, 1 cm, 9 mm, 8 mm, 7 mm, 6 mm, 5 mm, 4 mm, 3 mm, 2 mm, 1 mm, 0.5 mm, 0.25 mm, 0.15 mm, 0.10 mm, 0.05 mm, 0.01 mm or less and have the effect of increasing the irradiance as the distance becomes shorter, as described above.

In some embodiments, a light pipe, fiber bundle, or other light propagating or accumulating material can be used to increase the physical distance between the sample chamber and the detector and/or emitter. In these embodiments physical separations can be increased beyond several centimeters. In some embodiments, implementation of light pipes, fiber bundles, prisms, or other transparent materials to move the light may be of interest to assist in mechanical and/or electrical packaging.

In particular embodiments, the maximum distance between light source and the amplification/detection chamber (e.g. the distance between the light source and a location in the chamber that is the farthest away from the light source) is less than 2 cm, but more preferably less than 1.5 cm, 1 cm, 9 mm, 8 mm, 7 mm, 6 mm, 5 mm, 4 mm, 3 mm, 2 mm, 1 mm, 0.5 mm, 0.25 mm, 0.15 mm, 0.10 mm, 0.05 mm, 0.01 mm.

Such embodiments are able to reliably detect fluorescence during PCR with a system that is approximately 100-fold less optically efficient than typical PCR fluorescent detection systems. In one embodiment, the light source is a LED which uses 230 mA at 3.4V and has an efficiency of 50%, leading to an excitation light power of about 391 mW. The current from the detector, depending on the design of the detection chamber (as described above), may range from about 3 to about 30 mA, and given that the responsivity of a silicon photodiode in the 400-600 nm range is about 0.3 A/W, incident power of approximately 10-100 µW is reaching the photodiode detector in this embodiment. The optical efficiency, then, can be calculated as a ratio of input to output power using the formula:

$$\eta = \frac{\rho_{out}}{\rho_{in}}$$

Where:
μ=optical efficiency
$\rho_{out}$=power output of the photodiode
$\rho_{in}$=power output of the light source The optical efficiency of the system in this embodiment is about 0.0025% to about 0.025%, two log-orders less than typical PCR fluorescent detection systems, but as discussed below, this lower optical efficiency is permissible in some embodiments because of the method of measuring signal, noise, and the approach to calibration used. Sources of optical inefficiency in such systems include electrical energy which does not convert into light energy, light which does not illuminate the reaction sample, loss of energy to the emitting filter (either via absorption or reflection), loss to absorption of the reaction fluid and reaction vessel walls and other exposed elements in the enclosure, light which reaches the reaction fluid, but does not reach the photodetector's field of view, light which is absorbed by the filters covering the detectors, and loss to other optical and non-optical components.

It is preferred to produce a low-cost detector, and one design consideration which aids this is to minimize the number of components and the number of separate PCB boards. In typical PCR fluorescent detection designs, the illuminating side which contains the emitter(s) is opposite, orthogonal, or otherwise separated from the detection side which contains the photodetector. This format mitigates "cross-talk", or optical coupling, where light from the emitting light source is transmitted to the photodetector through a light-path which does not involve the fluorescent target absorbing and remitting light. However, separating components also increases cost by requiring two separate locations for the optical components and associated PCBs or light-pipes, depending on the design configuration.

An improvement on this design is to locate the emitter and detector components in close proximity, possibly on the same PCB or within an integrated package and mitigate cross-talk by shielding the components with opaque barriers such as over-molding, partitions, or opaque polymers or glues. Cross-talk can also occur via light transfer that occurs through the PCB itself, so in one embodiment, light source (e.g. LEDs) and photodetector (e.g. photodiode) components incorporate a metal or otherwise opaque backing so that the region of the electronic components nearest to the PCB is unable to transmit light through the fibers of the fiberglass PCB, or other translucent substrates. In some embodiments, the detection system has only one PCB. In some embodiments, all of the detection circuits are present in a single PCB. In other embodiments, the PCB which contains light sources is the same PCB that contains photodetectors, and these elements, when used for the direct illumination and detection of a PCR sample, are found in a single PCB. In other embodiments, the PCB which contains detection circuits is located in an environment that is thermally coupled to the detection environment.

In some embodiments, light pipes, fiber bundles, prisms, combinations thereof or other transparent materials are used to inject excitation light from a source, and/or to collect emission light and move it to a detector located not adjacent to the detection chamber, and may act functionally to replace the role of a lens. These configurations, while increasing cost and complexity, may be advantageous for packaging of larger detection components or emission sources to facilitate smaller detection chambers, or increase the effective collection area of the detector. For instance, a tapered light pipe could be used whereby the larger side of the component was placed near or in contact with the detection chamber. The narrow side of the tapered device would be in proximity or contact with a detector, thus acting as a light accumulator or lens. In this manner, the pipe would collect a larger area than the detector without the pipe, increasing the signal light collection area while maintaining a lower electrical noise on the detector.

Typical optic systems for PCR fluorescent detection use radiometry to calibrate the components of the optics system so that correction factors can be applied to the various components and the amount of emitting light can be calculated in an absolute sense. Without this calibration, it is not possible to accurately determine the fluorescence signal because unconsidered and uncalculated variations in the emitted light source produce significant quantitative deviations, which in the absence of calibration, could cause variations in the signal strength, which may lead to erroneous interpretation of measured signal.

Sources of variability in a typical optic system can occur between individual components, from unit to unit, as well as in the same unit over time. They include light emitter aperture size, angle, distance, and position of filter placements, angle, distance, and position of photodetectors, character (thickness, absorption, uniformity) of filter components and other components in the light path, quantum efficiency of the light source, light intensity, spectral distribution, degree and character of cross-talk between the emitter(s) and detector(s), attenuation of the light path due to dirt, debris, humidity, finish characteristics, or other manufacturing tolerances.

The combination of these factors drives increased cost as their mitigation tends to invoke manufacturing techniques and materials which minimize variability and require tighter tolerances, as well as requiring a unit-by-unit radiometric calibration sequence which constitutes an ever-larger percentage of cost as manufacturing volume increases and non-unit-by-unit costs fall.

In addition, even with an initial factory radiometric calibration completed, the optic system may need to be periodically recalibrated at the site of intended use, near to the time of use, because a variety of factors may cause the system to lose calibration over time or as the local environment changes. Those factors include degradation of filters, dyes, and materials over time, dirt and debris, humidity and the clouding of lenses or other optical path components, local environment temperature, wavelength changes of the emitter source due to aging, and optical alignment degradation.

The need to potentially recalibrate an optics system increases cost, requires skilled labor to be trained and available, may require specialized tools as well as the need to keep calibration materials on hand which themselves may expire or spoil.

Embodiments of the present disclosure obviate the need for calibration by employing a relative measurement without a fixed baseline. As a result, embodiments described herein are able to use inexpensive components (as they can be of relatively high variability and avoid the need for strict tolerances). Specifically, the light source can be an LED with a variability of 1%, 2%, 3%, 5%, 7%, 10%, 15%, 20% or more in alignment, output light character, color and intensity. In addition, optical alignment tolerances such as alignment of emitter and detectors become 0.5°, 1°, 2°, 3°, 4°, 5°, 6°, 7°, 8°, 9°, 10°, 12°, 15°, 20°, or more degrees, instead of less than 1,000 microradians, which is typical of precision optical systems found in the detection designs of current PCR machines. Similarly, acceptable translation tolerances of emitters and detectors is permissible on the order of 100's of microns, with 100 µm, 150 µm, 200 µm, 500 µm, 750 µm, or more permissible as opposed to single or double-digit microns, which is typical of the construction of detection systems used in current PCR machines.

As used herein, the term "LED" means any light source operating by means of a semiconductor diode that produces light when a voltage is applied, whether that light is employed directly, through a medium, via light pipes, optical fibers, or re-emitted through a secondary element.

In some embodiments, by obviating the need for unit-specific radiometric calibration, the detection system is able to use a relative measurement without a fixed baseline by performing the methods of analysis described elsewhere herein. These analyses can be done on one or more channels concurrently through the use of cut-off filters. Those filters can be short-pass (permitting wavelengths lower than a certain cut-off to be transmitted), long-pass (permitting wavelengths higher than a certain cut-off to be transmitted), or band-pass (permitting wavelengths only within a certain frequency range to be transmitted).

In some embodiments, the filters can be absorption filters, wherein dyes are incorporated into plastic, glass, polymers, or other materials, in some embodiments including by over-molding the optical components. In other embodiments, the filters can be thin-film filters. These may be vapor-deposited, use e-beam, evaporation, sputtering, dipped, sprayed, or other coating methods. The films may be single or multicomponent. In some embodiments, the filter may be deposited as a coating directly onto the detector. In other embodiments, the coating may be placed on a glass or polymer filter, either in a configuration where one or more emitters or detectors have individual filters, or in configurations where one or more filters is shared between or among one or more detectors or emitters, or in configurations where the absorption dyes or thin coats or other filter types are incorporated into a single monolithic filter with regions which correspond to their placement on the PCB. This monolithic filter may serve also as the end plate 231. In some embodiments, the filters may be located as part of one or more integrated units which also may contain the emitters and detectors.

In some embodiments, the different wavelengths of the emitter filters may be used in combination to perform detection in a manner such that the aggregate or sum of the incident light wavelengths provides distinct emission profiles used to distinguish the amplification of multiplexed analytes. In some embodiments, one or more photodiodes may be used to monitor the brightness of one or more of the emitter sources to allow compensation for variations in light intensity, including variations in brightness, and including variations caused by fluctuation of temperature that are not otherwise controlled or compensated for. An example of such emitter source photodetectors 239 is shown in FIG. 27. In addition, the inclusion of a photodiode, which monitors the brightness of emitter source may also be used to increase accuracy by providing a normalized background which in turn would allow a higher signal-to-noise ratio and improved sensitivity of detection.

It is generally preferred to use a short-pass filter on the light emitter because these filters typically exhibit a sharper "cut-off" than absorption filters. Such short-pass filters can have cut-off ranges as small as 1 nm, or less than 5 nm, 10 nm, 20 nm, 50 nm 75 nm or 100 nm. The optical rejection of out of band light (expressed in logs of difference of light passing above or below the cut-off) may be 5 log-orders for a typical thin-film short-pass filter.

One of the challenges in designing a low-cost optical system, particularly one without radiometric calibration, is that the thermal fluctuations of the device or environment can have a large adverse effect on the ability to differentiate signal from noise. The use of a photodiode as a photodetector is complicated by the mode of operation of photodiodes, which relies on the inner photoelectric effect. Incident photons create electron-hole pairs and generate an anisotropic current, which can be detected as an electrical signal. In practice, a baseline current is generated in the absence of light (the "dark current") and the current observed from the photodiode is the sum of the dark current and the photocurrent. The dark current can vary substantially, particularly in response to changes in temperature (from, for example self-heating of the light source, power supply, or detector circuitry components). As such, controlling the temperature or calibration along with compensating and correcting for the thermal environment are essential for accurate light measurement using a photodiode.

As discussed previously, the optical loop of PCR fluorescence detectors is typically radiometrically calibrated, leading to increased cost and the potential need for recalibration. Embodiments described herein obviate the need for these through a combination of approaches. First, the need to compensate for thermal fluctuations is diminished or eliminated if the environment is materially isothermal. To accomplish this, the device employs a common heatsink between the environment of the detector and the thermostabilized reaction chamber (for example between second end 152 and detection controller 234). This common heat sink, acting as a heat strap, maintains the PCB and optical components to a range within 3° C., 2° C., 1° C., 0.5° C., 0.3° C., or 0.1° C. and may include elements made of aluminum, copper, steel, noble metals, or other metals, (or other non-metallic thermal conductors such as diamond, cubic boron arsenide, carbon nanotube, graphene), heat pipes, liquid conduction, or any other materials with high conductance, preferably over 50 W·m$^{-1}$·K$^{-1}$, more preferably over 100 W·m$^{-1}$·K$^{-1}$, 150 W·m$^{-1}$·K$^{-1}$, 200 W·m$^{-1}$·K$^{-1}$, 250 W·m$^{-1}$K$^{-1}$, 300 W·m$^{-1}$K$^{-1}$, or higher.

The self-heating of the light source can be addressed in two ways. First, the light source can remain on during the detection phase of the reaction, allowing it to reach thermal equilibrium with the local environment. Alternatively, the diode can be pulsed quickly, to allow the cooling of the self-heating from the light source to return to baseline and prevent the accumulation of heat from increasing the temperature during the operation of the device. The specific maximum fractional period of light source activation which may be used in this embodiment can be calculated as:

$$\tau_{max} = \frac{\rho (1 - \phi)}{U\ A\ \Delta T}$$

Where:
$\tau_{max}$=maximum light source activation
$\rho$=power
$\phi$=quantum efficiency
U=heat transfer coefficient of the assembly
A=surface area of the heat source
$\Delta T$=temperature delta In some embodiments, the light source is pulsed for less than 1 ms, but preferably less than 750 μs, 500 μs, 400 μs, 300 μs, 200 μs, 100 μs, 50 μs, 40 μs, 25 μs, 15 μs, 10 μs, 5 μs, 3 μs, or 1 μs.

An additional improvement is to use a current-source power supply for fluorescence detection. Because output at the light source (LED in one embodiment) is most sensitive to current, rather than voltage, using a current-source power supply produces a smaller magnitude of variability in the flux of the emitter. Similarly, other electronic components which modify their behavior in response to temperature or current may exhibit unacceptably high variability in an environment where the temperature drifts or changes in the course of operation. In one embodiment, the use of low temperature coefficient resistors and other similar electronic components mitigates this issue, with variability of less than 5%, but more preferably 4%, 3%, 2%, 1%, 0.5%, or less across their operating temperature range. In another embodiment, the current source can be located within a region that is thermally coupled to the isothermal environment through the use of common heat sinking or heat strapping (for example, between the second end 152 and components of controller 195). In this way, thermal variation of the current source is minimized, allowing the use of resistors and other electronic components which are lower cost due to their increased variability, possessing manufacturing tolerances greater than 0.5%, 1%, 2%, 3%, 5%, 7%, 10%, 15%, 20% or more.

Piston Configuration

Embodiments disclosed herein may incorporate variations in the piston configuration. In certain embodiments, the piston has a cross-section which is round, which allows the chamber to rotate to the radial orientation with minimal friction. The piston or chamber may also incorporate small ribs or protrusions to minimize contact area, or center the piston. In some instances, this rotation aids not only with linear motion, but reaction fluid mixing as well. In some embodiments, helical grooves may aid in this mixing motion, or capillaries between the two piston ends may include a cant to induce radial motion. Mixing may also be improved by incorporating nozzles to direct fluid to the ends of the chamber as it moves, causing turbulence which aids in mixing, or the channel itself may include non-linear portions to induce vortex shedding or other turbulent patterns. Due to the relatively small volume used in most embodiments, the heat applied induces Brownian motion (and in some instances transient phase changes) which also contribute to mixing efficiency. Combinations of these techniques have a more than additive (i.e., synergistic) effect in some instances, and can occur in the ingress, amplification, or detection modules of the device.

In some embodiments, the piston may be a single piston. In other embodiments, the piston can be composed of granules which respond to magnetic fields, such as iron, nickel, cobalt, rare earth metals, alloys of such, or other ferromagnetic materials. In this way, under the influence of the magnetic field, the granules may preferentially migrate to one side of the chamber, displacing a portion of the reaction fluid to the opposite end of the chamber, where a thermal gradient exists. The magnetic field may then be reversed, inducing reciprocal motion of the granules and in turn the reaction fluid, effecting a thermocycle which may be repeated. In some embodiments, the granules are preferentially coated to prevent direct contact with the reaction fluid (which in turn may inhibit PCR). The coating may be a polymer, such as Delrin or a metal, such as chrome. In some embodiments, paramagnetic or diamagnetic granules of noble metals or low reactivity compositions may also be used to obviate the need for a coating without adversely affecting the amplification chemistry.

In certain embodiments, the piston may be a plurality of sections. The piston sections may operate in unison, moving to the same pole together, or may be operated such that they move in opposite directions, joining in the approximate center of the chamber during one (higher temperature) phase of the cycle, and returning to the distal poles during a second (lower temperature) phase of the cycle. This embodiment can allow a mode of motion with increased efficiency of heating such that the fluid to be heated may experience a surface area for heat transfer that is twice that of a piston motion mode where the entirety of the fluid is moved from one higher temperature pole to the other, lower temperature pole. An alternative embodiment to achieve a similar effect is to modify the piston (by, for example, increased length, decreased thermal conductivity, or altered heating parameters) such that the temperature at the center of the chamber corresponds to a desired lower temperature setpoint, and the poles correspond to the higher temperature setpoint. In other embodiments, one of the thermal zones may correspond to a third temperature zone, for example to facilitate classical three-temperature PCR (e.g., zone one being 95° C., zone two being 55° C., and zone three being 65° C.). As the piston sections reciprocate, the poles operate as the higher temperature zones, and the center as the lower temperature zones, exchanging a fraction of the fluid either around the piston, or through one or more capillaries between zones.

In some embodiments, the piston has a cross-section which is oval, polygonal, or any other two-dimensional shape which resists rotation or enforces orientation (see Zhang, Q., et al. (2015). Bioinspired engineering of honeycomb structure. Progress in Materials Science, 74, 332-400, incorporated by reference herein). In some embodiments, this configuration may be used, for example in circumstances including when paraplexing is used and piston orientation or rotation is considered in relation to adjacent other pistons. In some embodiments, the strength of magnetic fields or position of the magnetic elements are modified to decrease friction and allow free movement of pistons in a paraplexed arrangement. For instance, with weaker magnetic fields required in the magnetic elements, lower-cost magnets may be used, but the cumulative field strength of the paraplexed magnets is sufficient to allow effective piston movement. In other instances, the magnetic elements may be staggered (either by position within the two-dimensional paraplexed packing arrangement or by position along the axis of the pistons) to allow one or more pistons to operate independently from one or more other pistons. In some particular embodiments, the piston cross-section is hexagonal, rectangular (including square, linear conformations, and regular and irregular matrices of such shapes), circular or ellipsoid, or triangular. Adjacent chambers may be packed in a variety of manners, including offset, or square packing, angled, offset, or braced packing.

When used herein, "paraplexing" or "paraplex" (or related terms), means to contemporaneously perform a plurality of reactions which are separated for at least some portion of the reaction into different physical regions. In some embodiments, the apparatus may test an individual, divided sample. In other embodiments, the apparatus may test a pooled sample. In other embodiments, the apparatus may test a plurality of different samples. In various embodiments, the apparatus may test a combination of individual, pooled, or different samples. In some embodiments, a plurality of chambers may each contain one or more pistons, all of which may be collectively driven by a first magnetic coil. In other embodiments, a plurality of chambers may contain one or more pistons, all of which may be driven collectively by more than one magnetic coil, including two, three, four, or five, or more magnetic coils.

In still other embodiments, a plurality of chambers may each contain one or more pistons and a first magnetic coil, with said coil driving the piston(s) in that particular chamber. In additional embodiments, a plurality of chambers may each contain one or more pistons and a first magnetic coil, as well as a second magnetic coil, or more magnetic coils, with said coils driving the piston(s) in that particular chamber. In some embodiments, reaction conditions may be duplicated in paraplexed chambers to provide redundancy or additional sensitivity or specificity attributes.

Figure 32:
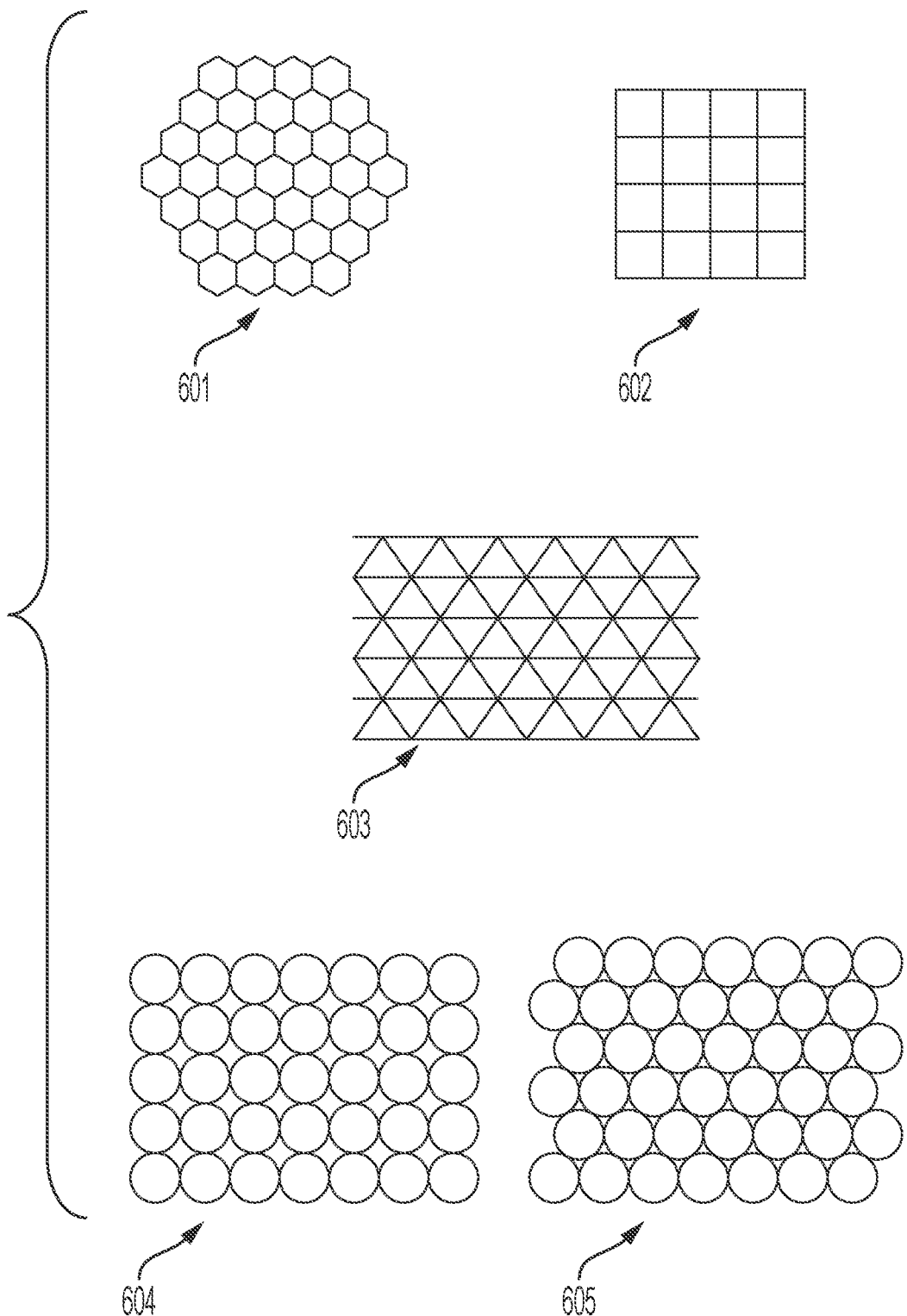
FIG. 32 illustrates schematic end views of various chamber packing configurations according to exemplary embodiments of the present disclosure.
Figure 33:
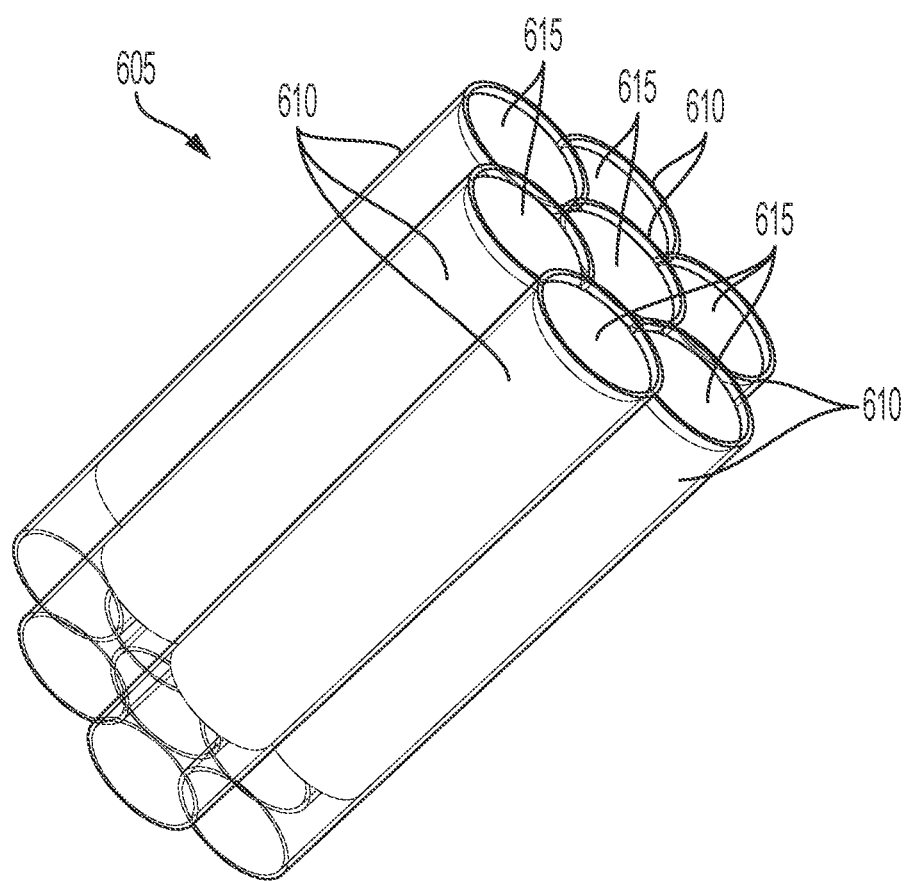
FIG. 33 illustrates a schematic perspective view of a chamber packing configuration according to FIG. 32 with a piston disposed in each chamber.
Figure 34:
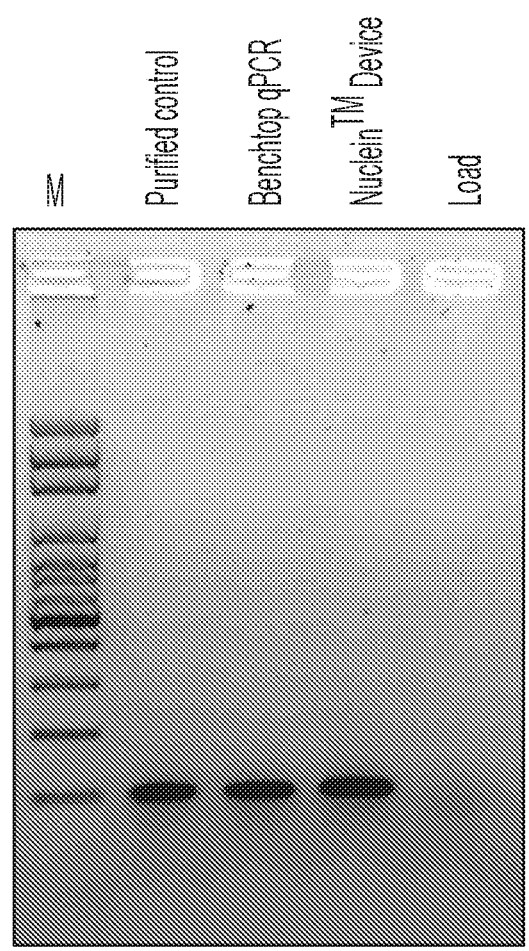
FIG. 34 illustrates a comparative amplification of *Streptococcus pyogenes* DNA segment between an exemplary embodiment of the present disclosure and an alternate device.
Figure 35:
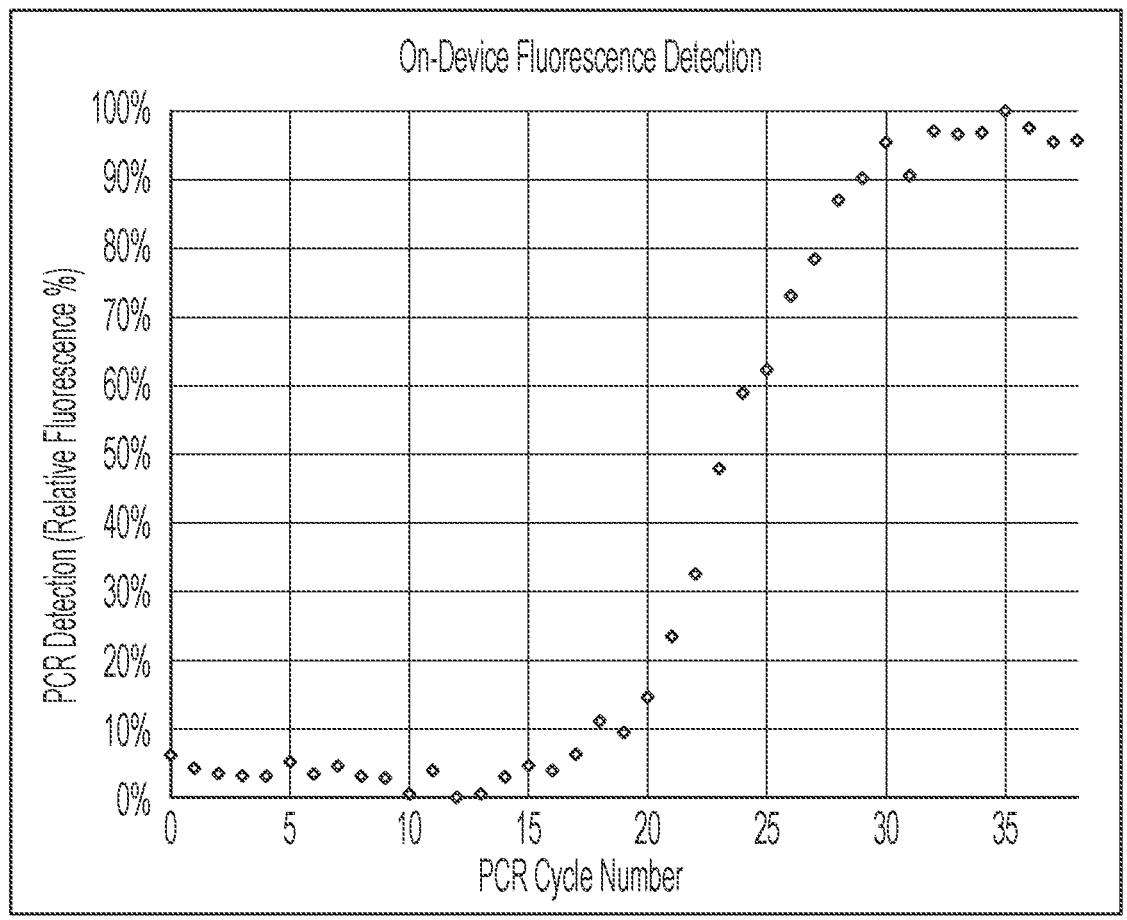
FIG. 35 is a graph illustrating on-device detection of *Streptococcus pyogenes* DNA segment using TaqMan probe and an exemplary embodiment of the present disclosure.
Figure 36:
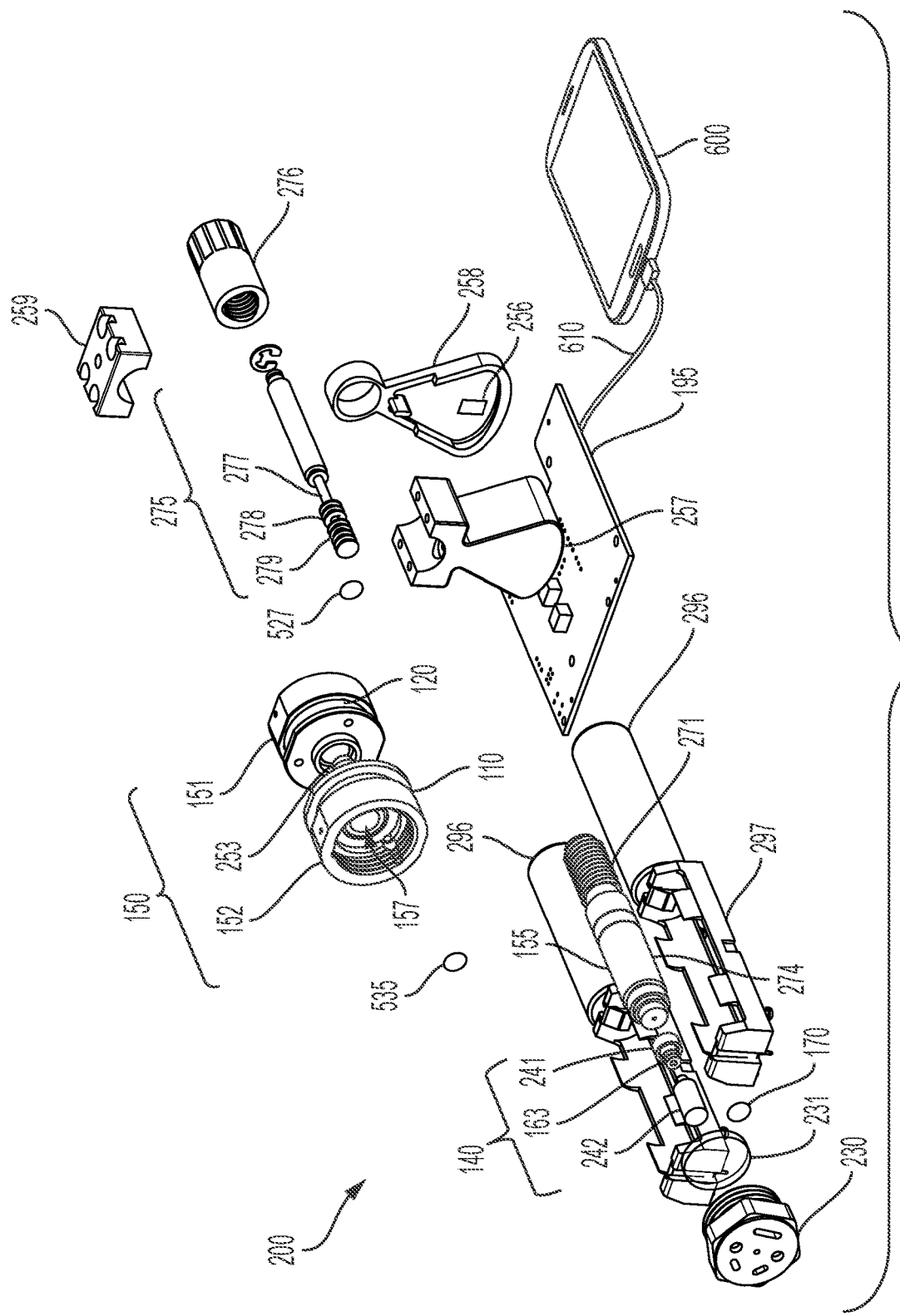
FIG. 36 is an exploded perspective view of an embodiment coupled to a smart phone or tablet.

Referring now to FIG. 32, schematic end views of various chamber packing configurations is shown that may be used for paraplexing, including a honeycomb configuration 601, a rectangular configuration 602, a triangular configuration 603, a square-packed cylindrical configuration 604, and a hexagonal-packed cylindrical configuration 605. In exemplary embodiments, a piston may be disposed in each chamber shown in the various configuration. FIG. 33 illustrates a schematic perspective view of hexagonal-packed cylindrical configuration 605 comprising a plurality of chambers 610 and pistons 615. As shown in FIG. 33, a piston 615 is disposed in each chamber 610. Paraplexing is in contrast to multiplexing, which occurs when multiple reactions may be run in the same physical region or reaction. In some embodiments, a reaction may be both multiplexed and paraplexed, allowing multiple reactions to occur simultaneously in multiple compartments (additional improvements in some embodiments include the use of Nested PCR to improve specificity of reaction). This can be accomplished with a variety of approaches, including fully separating the reaction chemistries, or by partially segregating them, and allowing, in some embodiments, a non-specific pre-amplification (or first amplification) step wherein the analytes are not specifically amplified by non-specific primers, and a subsequent step or steps wherein specific primers amplify or detect targets of interest more specifically.

In some embodiments, the percentage of air present in the reaction chamber can be 25%, 15%, 10%, 9%, 8%, 7%, 6% 5%, 4%, 3%, 2%, or 1%. As the reaction chamber heats, a portion of the oxygen and nitrogen from the air will become dissolved in the liquid phase of the reaction mixture according to the ideal gas law, but much will remain in gas phase. At air percentages of less than 10%, heating the reaction contents from room temperature to a temperature range of 95-99° C. causes the pressure to increase to approximately 3 atmospheres. Similarly, at an air percentage of less than 5%, heating the reaction contents to 95° C. causes the pressure to increase to approximately 5 atmospheres. Constructing pressure vessels to withstand higher pressures incurs additional cost and materials, so in some embodiments, the vessel pressure is maintained at less than 5 bar, 4 bar, 3 bar, 2 bar, or 1.5 bar, or employs a venting feature to allow excess air to escape.

Additional Exemplary Embodiments

Reaction Chamber Insert Configuration

Figure 6:
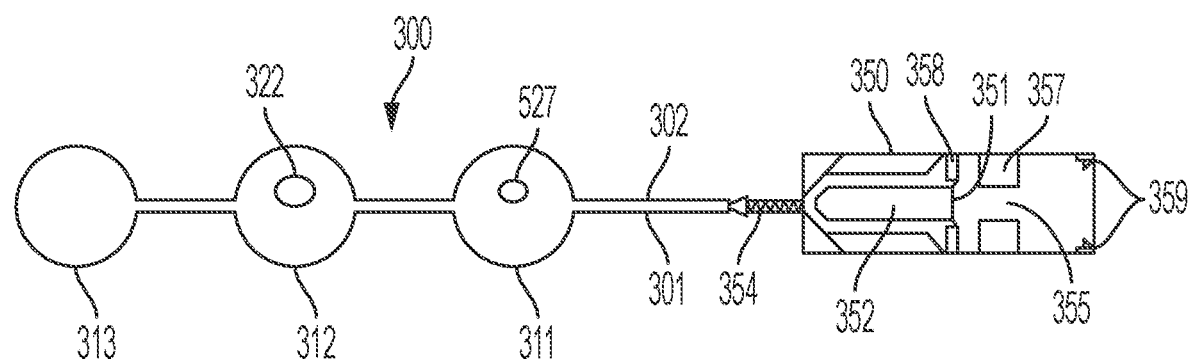
FIG. 6 is a schematic top view of an apparatus with a reaction chamber insert according to an exemplary embodiment of the present disclosure.

Referring back now to FIGS. 6-9, a further embodiment comprises an ingress module 350 and a reaction chamber insert 300 to physically separate the piston and cylinder material from the reaction fluid. In this embodiment, two flexible (e.g. polymer) sheets 301 and 302 (or a single sheet folded on itself) can be used to form multiple chambers. In FIG. 6, sheets 301 and 302 are shown in a top view configuration to form a first chamber 311, a second chamber 312 and a third chamber 313. It is understood that sheets 301 and 302 may be configured relatively flat prior to expansion into the configuration shown in FIG. 6. In particular embodiments, chambers 311, 312 and 313 may be formed by forming a seal using ultrasonic or thermal welding, adhesives, external clamping, (or any other mechanical or chemical method appropriate to withstand the pressures and temperatures of an operating device) to form a potential space which may act as fluid chambers for reciprocal motion of the reaction fluid. In the embodiment shown, chamber 312 comprises PCR reagents 322 and chamber 313 can function as an overflow chamber (e.g. to accept excess air or fluid overflow from chambers 311 and 312).

FIG. 6 illustrates a top view of the reaction chamber insert 300 and ingress module 350 before use. Ingress module further comprises a membrane 351 that seals a fluid 352 (e.g. dilution, lysis, or other sample preparation fluid), as well as a sample port 355.

Figure 7:
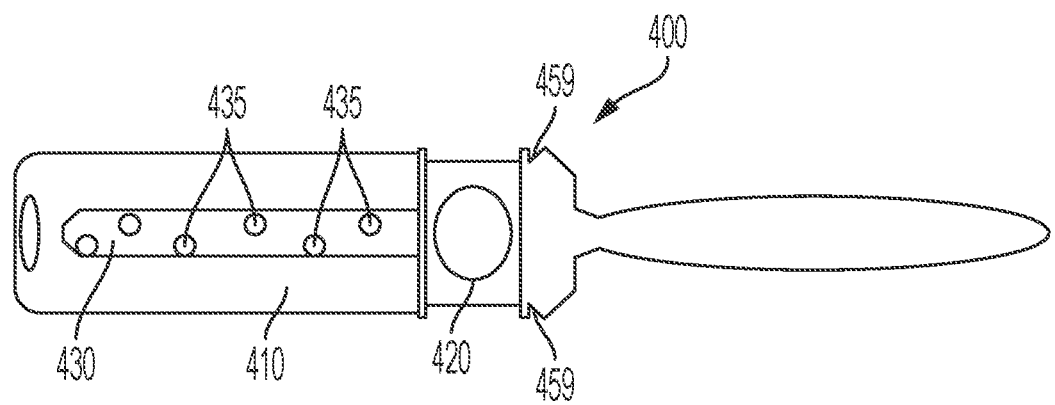
FIG. 7 is a schematic side view of a sample loading device configured for use with the embodiment of FIG. 6.

FIG. 7 illustrates a side view of a sample loading device 400 configured to load a sample in the sample port 355 of the ingress module 350. Sample loading device 400 comprises an absorbent material 410 (e.g. a sponge) configured to absorb a sample. In particular embodiments, sample loading device 400 can be exposed to a sample (e.g. swabbed in an oral cavity or otherwise placed in contact with a sample) such that absorbent material 410 can absorb a sufficient volume of the sample to change the status of indicator 420. In particular embodiments, indicator 420 may change color or otherwise change status when a sufficient volume of sample has been obtained by sample loading device 400. Sample loading device 400 comprises a lancet 430 with apertures 435 that allow the sample from absorbent material 410 to enter lancet 430 and contact indicator 420.

After sample loading device 400 is loaded with a sample, it can be inserted into sample port 355 of ingress module 350. Ingress module 350 also comprises a shoulder 357 that compresses absorbent material 410 and extracts the sample from absorbent material 410 when sample loading device 400 is inserted into ingress module 350. In addition, shoulder 357 stops the progression of sample loading device 400 as it is inserted in sample port 355. Ingress module 350 further optionally comprises locking tab 359 that engages notch 459 in sample loading device 400 to retain sample loading device 400 within ingress module 350.

Lancet 430 is configured to penetrate membrane 351 when sample loading device 400 as inserted into sample port 355. By breaking membrane 351, the sample from sample loading device 400 can be mixed with dilution fluid 352. The combination of sample and fluid 352 is filtered by optional filter 358 and directed to mixer 354 when sample loading device is fully inserted into ingress module 350.

Figure 8:
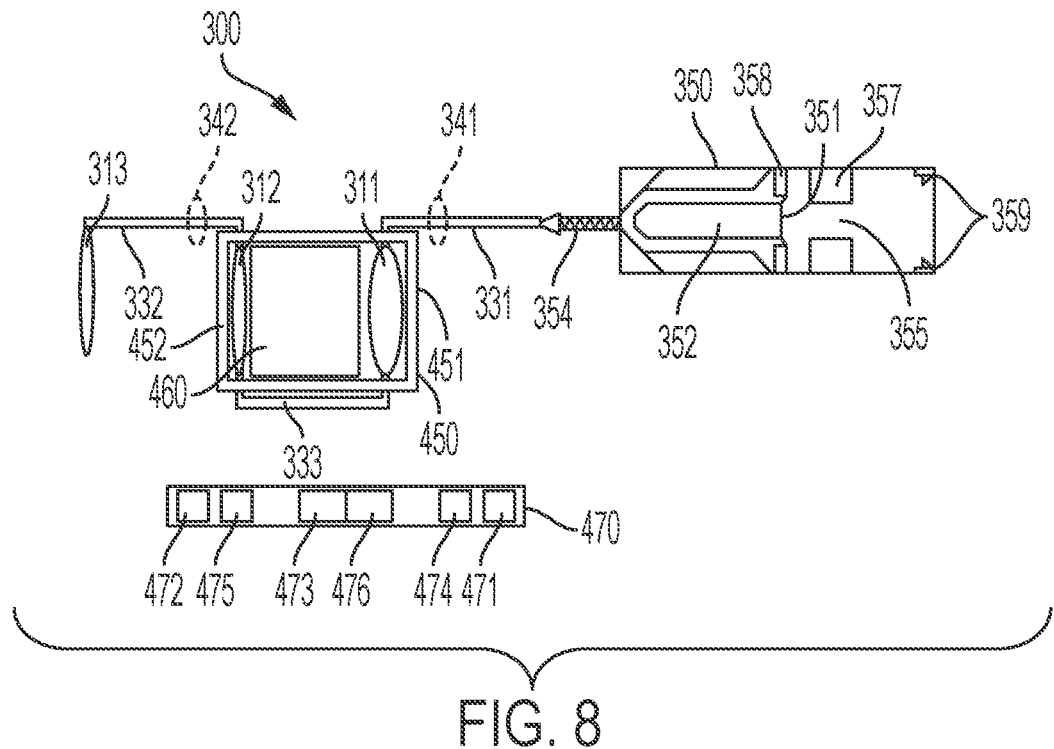
FIG. 8 is a schematic side view of the embodiment of FIG. 6 during use.
Figure 9:
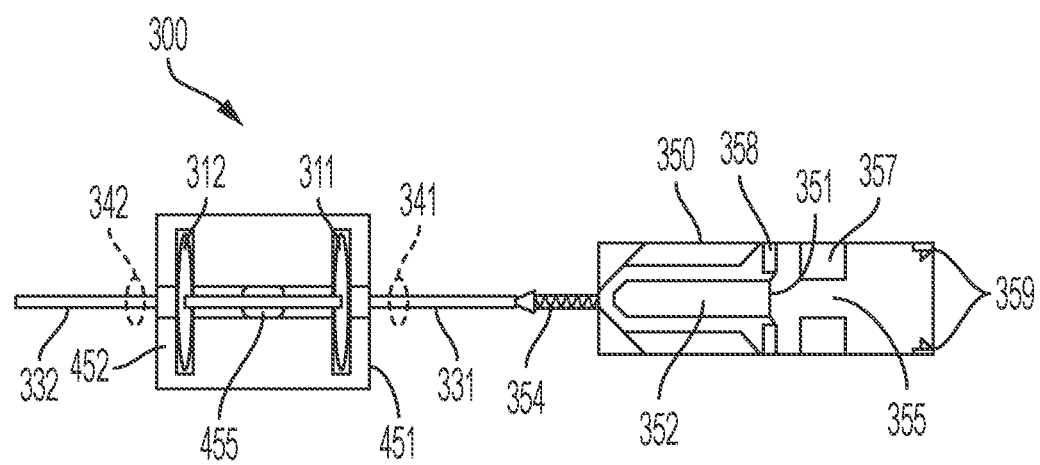
FIG. 9 is a schematic bottom view of the embodiment of FIG. 6 during use.

FIGS. 8 and 9 illustrate side and bottom views of the reaction chamber insert 300 inserted into a housing 450 with a first end 451 and a second end 452. A piston 460 disposed within housing 450 is configured to move between a first position proximal to a first end 451 and a second position proximal to a second end 452 to move reaction fluid within reaction chamber insert 300.

In certain embodiments, reaction chamber insert 300 contains two larger diameter areas corresponding to the two sides of piston 460, and channels connecting them and extending distally and proximally which are preferably of a smaller diameter to minimize dead space. In the embodiment shown, a proximal channel 331 is connected to ingress module 350, and a distal channel 332 (if present) connects to overflow/gas reception chamber 313 to chamber 312. An intermediate channel 333 couples chamber 311 and chamber 312.

In some embodiments, sample loading device 400 is inserted into ingress module 350 to introduce the sample to the reaction chamber insert 300 in the manner described above. After the sample has been loaded into the reaction chamber insert 300, channel 331 is sealed at seal location 341 and channel 332 is sealed at seal location 342.

Housing 450 can be coupled to a base 470 with heat sources 471 and 472, as well as illumination source 476, detector 473 and actuators 474 and 475. In other embodiments, a single heat source and actuator may be incorporated in base 470. Actuators 474 and 475 can be used to direct piston 460 back and forth between the first and second positions, and heat sources 471 and 472 can be used to heat the reaction fluid in reaction chamber insert 300 in order to perform PCR or other amplification techniques on the contents of reaction chamber insert 300.

Housing 450 may comprise a reflective surface 455 so that detector 473 can detect a response from reaction chamber insert 300 (e.g. a fluorescent signal in response to an illumination of reaction chamber insert 300 by illumination source 476). In certain embodiments, housing 450 may be formed from two or more pieces that are coupled together. In a particular embodiment, housing 450 may formed such that first end 451 and second end 452 are part of separate components with interdigitated portions forming the central portion of the housing that include gaps or slots to accommodate intermediate channel 333. In certain embodiments, chamber 313 may be formed as a third larger diameter (or volume) area that is incorporated (either as part of the insert, or in continuity with it) to serve as a receptive reservoir of any gas from channel 332 which precedes the ingress of the sample or lysis fluids, or an excess of these fluids. This can maximize the liquid to gas ratio of the reaction fluid and decrease backpressure during filling. This can further provide faster heat transfer, avoidance of gas over liquid movement preference dynamics, and maximization of the reaction analyte which can improve sensitivity and decrease reaction time. In particular embodiments, third chamber 313 may be formed of a different material, either sealed (accommodating increased pressures with or without sensors present that indicate fill status) or containing a vacuum, or with direct or indirect communication with atmospheric pressure, including porous or absorptive fillers or chambers designed to accommodate gas and liquid.

Sealing of reaction chamber insert 300 both proximally and distally (for example, at seal locations 341 and 342) can be accomplished in a variety of manners including thermal, ultrasonic, valve-based, chemical, phase-change, or via mechanical pressure induced by any number of methods which will be apparent to the practitioner. This sealing occurs during device operation such that a closed reaction chamber is formed within the bounds of reaction chamber insert 300, containing the reaction fluid and allowing the compressive pressure of piston 460 to effect a contrary movement of the reaction fluid between poles of piston 460, through the channel which joins the larger diameter sections of the insert.

The use of reaction chamber insert 300 can allow for more forgiving design tolerances for piston 460 and cylinder or housing 450, among other components. When considering the piston design, it is typically desirable to decrease dead space constrained by movement of the piston within the cylinder or housing in order to efficiently thermally cycle the reaction fluid between the desired temperature ranges. However, as the tolerances become tighter, movement of the piston may be impeded by friction (either direct, or as a consequence of the reaction, small asperities, floating particles, or adhered debris). This impingement is also subject to dynamics within the reaction, such that the viscosity or differential thermal expansion of components may cause impingement.

Accordingly, it can be beneficial to tighten tolerances to minimize dead space, but to maintain a design margin which prevents impingement. In some embodiments, it can be preferable to maintain tolerances such that the space between the piston and the cylinder is no more than 10 mils (thousands of an inch), but more preferable to maintain tolerances of 7 mils, 5 mils, 3 mils, 2 mils, or 1 mil, accounting for the thermal expansion differential between the piston and the cylinder if different materials are used, including magnets, metals, and polymers. The inclusion of an insert uncouples these two opposing parameters, facilitating the movement of the piston by allowing laxer tolerances between the piston and chamber (which also reduces manufacturing cost) while not increasing the dead space as a result, because the reaction fluid is contained within the insert, and dead space does not change with piston-cylinder tolerance changes.

Additionally, the insert may contain lyophilized reaction components, which should preferably be contaminant-free to minimize the risk of including nucleases or environmentally present nucleic acids, which might produce spurious results. The use of the insert confines the above (and other) stringent manufacturing requirements to the ingress module and insert, allowing flexible, inexpensive, rapid, and specialized production of the other device components.

In particular configurations, the dead space will not exceed 35%, or particularly, it will not exceed 25%, or more particularly it will not exceed 20% of the total reaction volume, or more particularly, it will not exceed 15%, or even more particularly, it will not exceed 10%, or most particularly, it will not exceed 5% of the total reaction volume.

Non-Piston Configuration

Figure 10:
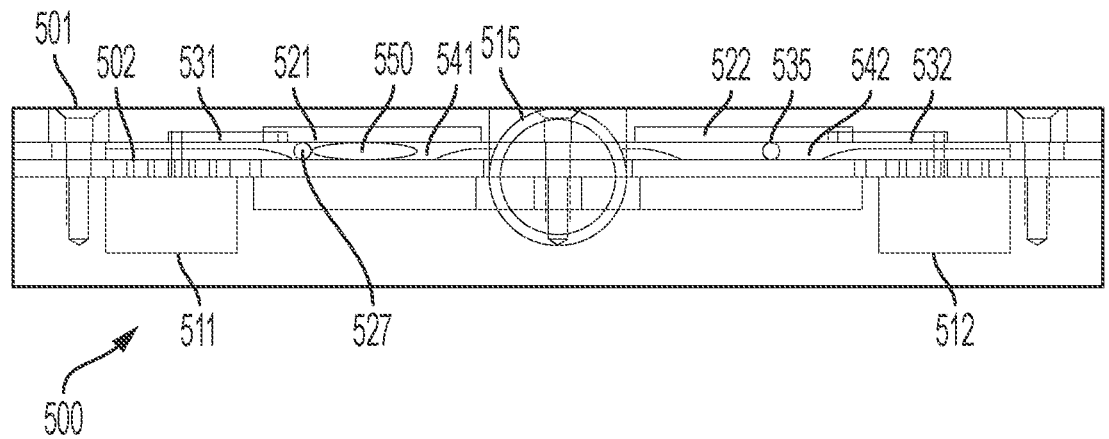
FIG. 10 is a schematic side view of an apparatus without the requirement for a piston according to an exemplary embodiment of the present disclosure.
Figure 11:
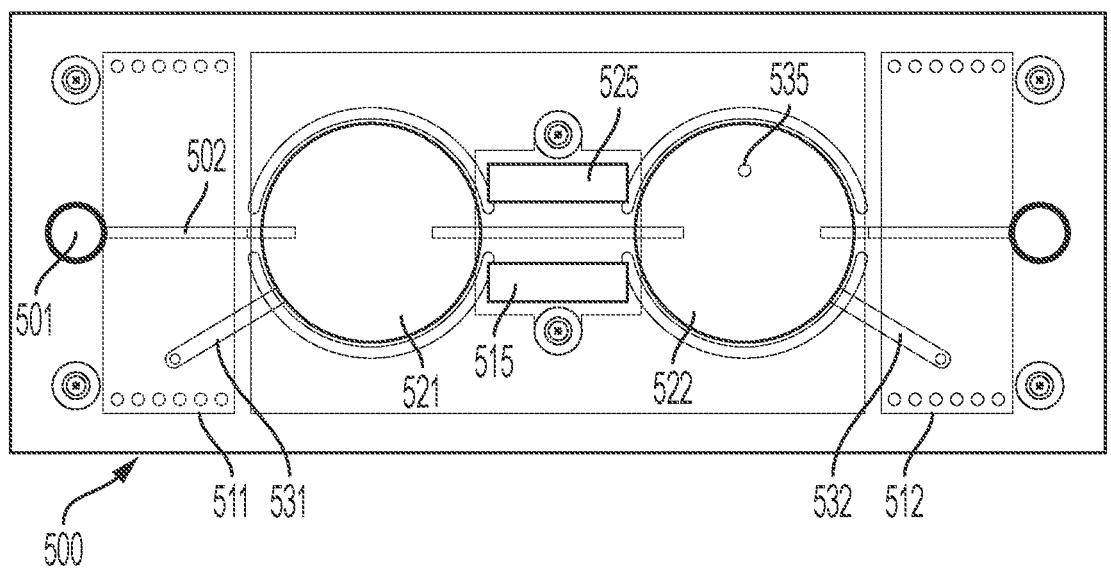
FIG. 11 is a schematic bottom view of the embodiment of FIG. 10.
Figure 12:
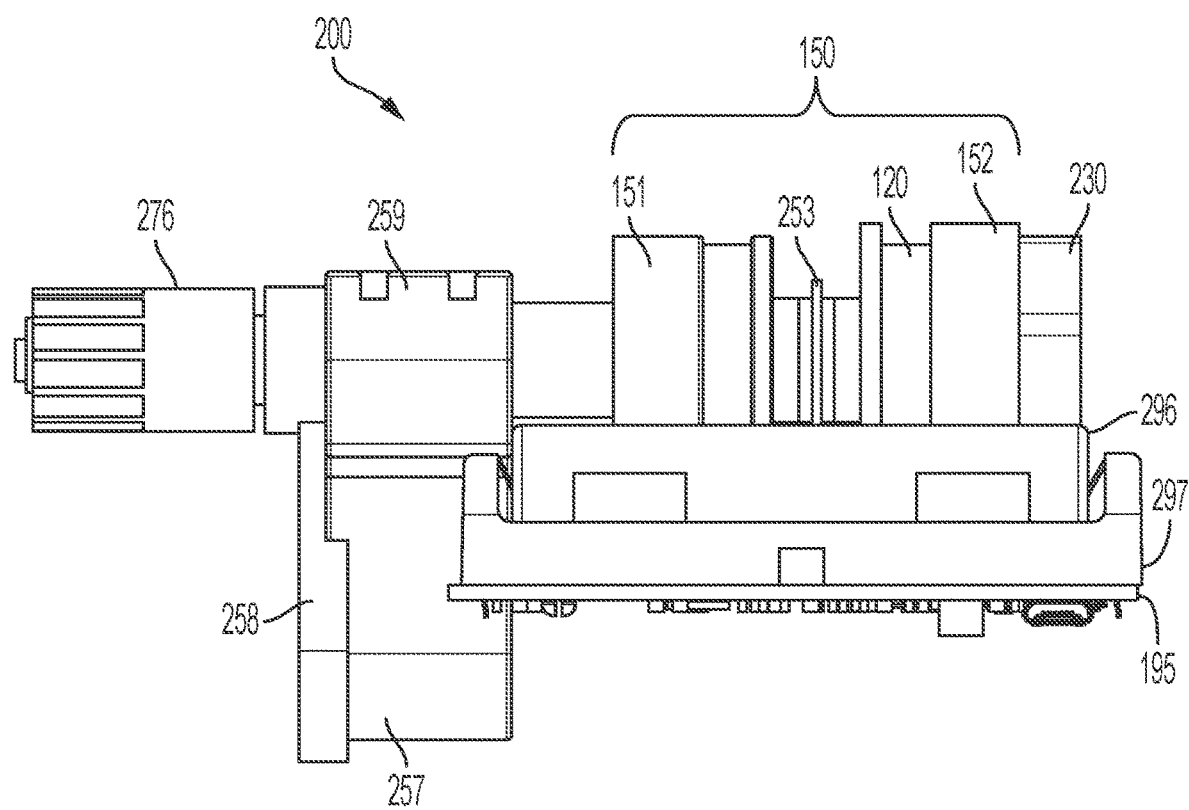
FIG. 12 is a side view of an apparatus according to a second exemplary embodiment of the present disclosure.
Figure 13:
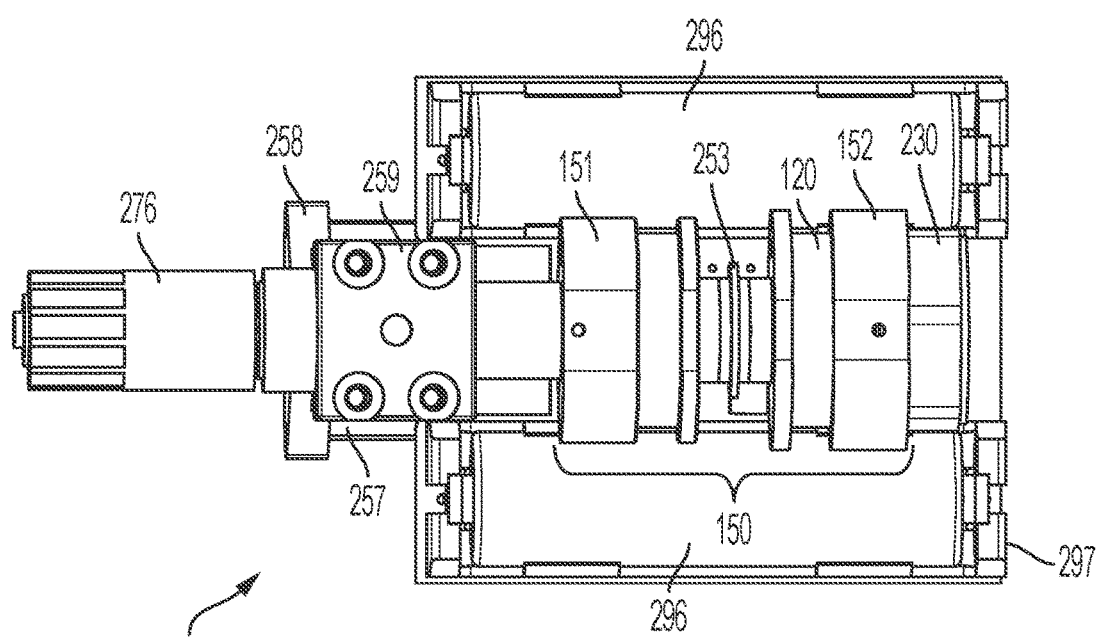
FIG. 13 is a top view of the embodiment of FIG. 12

Referring now to FIGS. 10-11, a further embodiment is to arrange the device such that the requirement for a piston is obviated. This may be accomplished by collocating the two temperature regions in the same plane, whereby a lever, or the hydraulic action of a fluid column, or the thermopneumatic expansion or phase-change (flash boil) gas expansion acts to directly (through a flexible membrane) or indirectly via a mechanical bridge or disc (which may optionally apply a downsizing of the contact area to gain a mechanical pressure advantage) effects the movement of fluid from a higher temperature side to a lower temperature side.

When constructing a device that lacks a reciprocating piston, materials which can be suitable for the formation of flexible regions include polymers such as polydimethylsiloxane (PDMS). These polymers can be formed into the desired shape by using a negative molding process, whereby a dissolvable mold, for example, poly(vinyl) acetate (PVA), can first be formed. The PDMS can then be poured over the PVA form, and allowed to cure (partially or fully, as desired). The PVA can then be removed by dissolution in aqueous solution, such as water, optionally assisted by agitation, heat, air pressure, or ultrasound. This particular embodiment allows the formation of a flexible form which is compatible with amplification chemistries such as PCR, and obviates the requirement for seals or gaskets which might later leak.

PDMS, and other polymers may also be partially cured, (or their surfaces may be rendered reactive after fully curing by means of electrostatic discharge or chemical reactivation), and annealed to one another by modulating the temperature and concentration of polymer in solution. For instance, PDMS can be cured quickly (in some cases, less than about 10 minutes) at higher temperatures (e.g. greater than about 150° C.), or cooled more slowly if greater working time is desired.

In the specific embodiment shown in FIGS. 10-11, a device 500 comprises an input port 501 for introducing a sample. Device 500 also comprises a first thermo-pneumatic chamber 511 and a second thermo-pneumatic chamber 512, as well as an illumination module 525 and a detection module 515. In the illustrated embodiment, first thermo-pneumatic chamber 511 is coupled to a first expansion member 521 via a first channel 531. Similarly, second thermo-pneumatic chamber 512 is coupled to a second expansion member 522 via a second channel 532. First and second expansion members 521 and 522 may be formed from a flexible material that can be deformed (e.g. from a relatively flat configuration to a curved configuration) when the contents of the expansion members increase in volume.

First thermo-pneumatic chamber 511 and second thermo-pneumatic chamber 512 can each contain an expandable fluid (e.g. a gas or liquid) that expands when heated. As the contents of first thermo-pneumatic chamber 511 are heated, the contents flow through first channel 531 and into first expansion member 521, causing first expansion member 522 to expand. Similarly, the contents of second thermo-pneumatic chamber 512 can be heated to expand second expansion member 522 via channel 532.

During operation, a sample 550 can flow from input port 501 through an input channel 502 to a region 541 below first expansion member 521 which may comprise a pellet 527 comprising lysis reagents suitable for PCR or other amplification techniques. When first expansion member 521 is expanded (e.g. via heating the contents of first thermo-pneumatic chamber 511), sample 550 can be directed from a region 541 past detection module 515 and illuminating module 525 to a region 542 below second expansion member 522. Region 542 may comprise a pellet 535 comprising buffers and reagents suitable for PCR or other amplification techniques. When the sample reaches region 542, second expansion member 522 can be expanded (e.g. via heating the contents of second thermo-pneumatic chamber 512) and first expansion member 521 can be contracted (e.g. via reducing the temperature of the contents of first thermo-pneumatic chamber 511 and the return of contracting gas through first channel 531). This can direct sample 550 from region 542, past detection module 515 and illumination module 525 and back to region 541. The process can be repeated to cycle sample 550 between regions 541 and 542, which can be maintained at different temperatures suitable for amplification techniques as disclosed herein. Sample 550 may be illuminated by illumination module 525 and the response detected by detection module 515.

Additional Design Considerations

Differences often exist between the measured temperature and the actual temperature due to probe accuracy, probe placement, thermal resolution, temporal resolution, the presence of waste heat, and the challenge of locating probes as close as feasible to the reaction fluid without increasing the risk of leaks from a perforating or incompletely sealed sensor. Accordingly, in certain embodiments the device can be calibrated to allow for software compensation of the readings. Although the method of compensation is dependent on the specific geometry of the embodiment, a linear, static compensation may be achieved by locating the sensors within 3 mm, or more particularly within 1 mm, and even more particularly within or in communication with, the reaction fluid.

As used herein, sensors refer to methods of detection including temperature, pressure, mechanical position (e.g. of the piston), presence of liquid in a channel by optical, conductivity, capacitance change (which is preferred to prevent chemical effects of direct electrode contact, potential for leads and manufacturing complexity), or by movement actuating a switch, or other detector which will be apparent to the practitioner. Certain embodiments can avoid the use of mechanical switches, sensors, or valves, which is not required for a piston-based PCR device and contribute to cost, complexity, and limit manufacturing options and flexibility. Sensors may be directed to internal states within the device, to environmental conditions or states, or may receive information from sources outside the device.

Further enhancements may be achieved by using materials with higher thermal conductivity, preferably above 1 W/mK for polymers, and 10 W/mK for (more preferred) metallic conductors, with conductivities above 100 W/mK even more preferred, and those above 300 W/mK even more preferentially preferred. Harder materials are preferred due to their tendency of increased thermal conductivity in practice, even if theory or reference literature does not report such thermal conductivity. The increased hardness additionally allows advantages during manufacturing and assembly, with higher speed, decreased precision, and more versatile handling options. Any polymer with sufficient working temperature (typically at least 110° C., but in any event greater than the maximum reaction fluid temperature unless thermal bridges or heating pulses are employed, and preferably at least 115° C., 120° C., 130° C., 150° C., or higher) is permissible, however, polymers with higher resistance to abrasion and compression are preferred, with Rockwell R numbers of at least 50 being preferred, but hardness of 60, 70, 80, 90, 100, or higher being even more preferred.

Additionally, thermal transfer may be further enhanced by coating materials which would otherwise interfere with lysis, amplification, or detection chemistries to achieve higher thermal conductivity. In one embodiment, the material is aluminum, and although aluminum and aluminum oxides are not commonly thought to be inhibitory to PCR, under certain chemical conditions, PCR inhibition is seen, and unwanted effects such as the spontaneous hydrolysis of 5' hydrolysis probes such as TaqMan can be seen, such that the use of aluminum requires further protective measures. Specifically, for example, the use of a polymer coating (or any permissive coating) or a liner or insert over the aluminum permits its use where it would otherwise be inhibitory under certain conditions. An additional benefit of using materials with higher thermal conductance is the ability to more quickly ramp the temperature, thus increasing speed, particularly in the initial heating stages. Coatings may be thin-coat, conformal coating, noble metal (such as gold, silver, platinum, rhodium, iridium, palladium, ruthenium, etc.) coatings, lacquers, ceramics, or myriad other coating and plating techniques that will be apparent to the practitioner, constrained by avoiding metals which form inhibitory oxides, or chemical reactants such as epoxies.

The ability to quickly ramp the temperature is further enhanced by materials which have a working temperature which is higher than the highest reaction fluid temperature, for example, at least 10° C. above the reaction fluid temperature, or even more particularly 15° C., 20° C., 30° C., 50° C., 75° C. or 100° C. or higher than the reaction fluid temperature. This can allow an over-temperature target during the initial heating cycle to shorten the duration of the period where the reaction fluid and surrounding materials act as a heat sink. Over-temping in this manner, and the permissiveness of materials to over-temping is additionally advantageous because it decreases the required precision, and maximum deviation of thermal control loops such as PID (i.e., proportional-integral-derivative controller), or any subset or extension of a like control method. This again lowers cost both directly, because of the decreased component complexity and precision required, as well as indirectly, by increased manufacturing flexibility and lower precision requirements (e.g. in sensor or other component placement).

A further enhancement to facilitate over-temping is the inclusion of a phase-change wax or other material around or thermally coupled with the high temperature zones to act as a buffer for excess heat, selecting the attributes of the material or materials such that its melting temperature is lower than the maximum working (operating) temperature of the device material, but preferably with a temperature threshold of at least 5° C., but preferably 10° C., 15° C., 20° C., 30° C., 50° C., such that excess heat which might otherwise damage the device material is absorbed by the phase-change material as the heat of fusion. This further acts as a heat reservoir for the high temperature zone, minimizing passive heat loss and decreasing power requirements.

In contrast to high thermal conductivity between the heating (or cooling) elements and the reaction fluid (or indirectly, though an insert), for non-isothermal amplification embodiments, low thermal conductivity can be preferable in the piston and components which communicate between the two temperature zones. In some embodiments, the thermal conductivity can be less than 1 W/mK, 0.5 W/mK, 0.1 W/mK, 0.075, W/mK, 0.5 W/mK, 0.4 W/mK, 0.3 W/mK, 0.25 W/mK, 0.2 W/mK, or 0.1 W/mK. Low thermal conductivity in the piston and surrounding components (at the thresholds, to the degrees, and in the fashion described above for high thermal conductivity) can be achieved by polymer selection (including binder and curing agents), length, cross-sectional area, and geometry of the piston (and surrounds). Preferably, voids or aerogels are included within the piston and surrounds to limit thermal transfer while not increasing the potential dead space of the embodiment, optionally combined with structural components to provide sufficient rigidity and durability to the piston and surrounds such as cross-members or other structural components that will be familiar to the practitioner.

Decreasing thermal conductivity (or increasing the insulative factor) can also be useful in the area surrounding the endcaps of the device, most useful on the higher temperature side, the first end 151 in some embodiments, particularly when the high temperature side is above 90°, and even more particularly when it is above 92° C., 93° C., 95° C., or higher. The endcaps themselves may be press fit, welded or polymer welded, screw-in, or incorporate O-rings or other common approaches used in pressure vessels. Alternatively, they may incorporate an accordion design such that the piston remains stationary relative to the device, and translational movement during the stroke cycle is performed by the cylinder and endcaps. In another embodiment, the cylinder may be absent, with only the piston and receiver endcaps present. Reciprocal motion is achieved by a rigid, semi-rigid, or elastic cross-member between endcaps, or without such a member, wherein the fluid pressure from one endcap acts as a hydraulic to move the other endcap. Additionally, the endcaps may be a part of the cylinder, such that they form a single unit.

The choice of polymer for a reciprocating piston-based PCR device can be driven by several factors including maximum and minimum operating temperatures, flexibility, water absorption (in some embodiments less than 1%, 5%, 10%, 25% w/w), fluorescence absorption (which in some embodiments involving fluorescent or colorimetric detection is directed to minimizing the absorbance of incident light from a light source such as an LED, with some embodiments having less than 0.1%, 0.5%, 1%, 5%, or 10% absorbance), fluorescence leaching/background fluorescence, including autofluorescence with some embodiments having a signal to noise ratio of greater than 2:1, 5:1, 10:1, 25:1, 100:1, 500:1, and PCR inhibition, with some embodiments having inhibition of less than 1%, 5%, 10%, 25%, 50% compared to PCR without the particular choice of polymer present. In certain embodiments, the maximum working temperature can be above 120° C., or more particularly 130° C., 140° C., 150° C., 160° C., or higher. In specific embodiments, the minimum working temperature can be less than 25° C., or more particularly 15° C., 10° C., 5° C., 1° C., or lower. In certain embodiments, it can be desirable to use a material with high rigidity (low flexibility), with Young's modulus values greater than 0.1 GPa or more particularly greater than 0.2 GPa, 0.3 GPa, 0.5 GPa, or 1 GPa.

The ability of the materials to maintain function across a range of temperatures and pressures is also an important factor in selecting a polymer, and as discussed elsewhere herein, the thermal expansion of the components, and also particularly the differential thermal expansion of nearby components can be considered to ensure that at higher temperatures, they do not exceed tolerance values or that when sealing perforations in the reaction chamber, leaks do not develop at higher or lower temperatures. In certain embodiments, the polymer and materials forming sealed perforations can be selected such that the higher thermal expansion component rests within the lower thermal expansion component, particularly with the geometry arranged such that expansion presses the components closer together (for example by use of angled inserts or design components such as check-valves). In some embodiments, the thermal expansion of adjacent materials can be within 10%, 9%, 8%, 7%, 6%, 5%, 4%, 3%, 2%, 1.5%, 1%, 0.5% of each other, or less.

In a similar fashion, the water absorbance of the materials forming the piston chamber can be considered at the extremes of the allowed operating temperature, with water absorption less than 0.5%, or more particularly less than 0.3%, 0.2%, 0.1%, 0.05%, 0.01%, or lower. Of note, water absorbance is of lesser concern for polymer components which are not part of the piston chamber (for example, those storing carrier or lysis fluid) due to the decreased tolerance requirements. In this case, water absorbance can exceed the ranges identified above, but can be limited by mechanical leaking (as swelling or shrinking deform storage seals), where the concentration of reagents is altered beyond the ranges identified elsewhere herein, or where other factors contribute to cumulatively cause these effects.

In particular embodiments, minimizing inhibition of the PCR reaction can be an important design consideration, and the device in some embodiments can exceed 80% of the control reaction, or more particularly 90%, 95%, 98%, 99%, or 100% of the control reaction. In addition to the polymer selected for use in a particular embodiment, any associated binders, curing agents, solvents, lubricants, or dyes which are incorporated should be considered when selecting the polymer. Often, there are multiple options per polymer type, including those without dyes, and containing various degrees of cross-linking, polymer length, or additives which alter the characteristics of the polymer (e.g. Zhang G., et al. "Increasing Polypropylene High Temperature Stability by Blending Polypropylene-Bonded Hindered Phenol Antioxidant", Macromolecules, 2018, 51 (5), pp 1927-1936), incorporated herein by reference). In some embodiments, the polymer is Delrin. In some particular embodiments, the Delrin is undyed.

In addition to the piston and cylinder, any other polymers or materials which contact the reaction fluid should also be considered, including O-rings, metals, adhesives, and artifacts of the manufacturing process. For example, Viton O-rings have a lower inhibition of PCR than nitrile O-rings, and can be preferred in certain embodiments due to their otherwise acceptable operating profile.

An exemplary comparison of several polymers is included below for convenience, but is not meant to represent an exhaustive list of options:

|  | Max temp (° C.) | Min temp (° C.) | Transparency | Flexibility | Water absorption % |
| --- | --- | --- | --- | --- | --- |
| Ideal | >160 | 0 | +/− | R | <0.01 |
| LDPE | 80 | −50 | TL | F | <0.01 |
| HDPE | 120 | −100 | TL | R | <0.01 |
| Polypropylene | 135 | 0 | TL | R | <0.02 |
| Polypropylene Copolymer | 121 | −40 | TL | R | <0.02 |
| Polystyrene | 70 | 0 | C | R | 0.05 |
| Acrylic | 90 | −60 | C | R | 0.3 |
| PTFE (Teflon) | 300 | −200 | O | R | 0.3 |
| Polymethylpentene (PMP) | 145 | 0 | C | R | <0.01 |
| PVC | 70 | −25 | C | R | 0.06 |
| Polycarbonate | 130 | −135 | C | R | 0.35 |
| Perfluoroalkoxy (PFA) | 270 | −250 | TL | R | <0.03 |
| DELRIN (acetal) | 120 | −40 | O | R | 0.25 |
| PCTFE (Kel-F/Neoflon) | 132 | — | C | R | <0.01 |
| Pulysulfone (PSU) | 140 | — | TL | R | 0.3 |

Legend: Transparency: TL=Translucent, C=Clear, O=Opaque. (For certain measurement techniques involving transillumination, transparent material is preferred for use in the cylinder and endcaps to permit piston position measurements. For other embodiments such as hall (magnetic sensor) measurements that do not use transillumination, it is not a consideration, and instead non-ferromagnetic materials are advantageous (except to the extent that such materials are deliberately used to extend or propagate magnetic field conformation). In other embodiments, darker or opaque materials absorb light to a larger degree and permit less entrance of light from outside the reaction environment, and may be advantageous due to a lower background and improve signal to noise ratio. In particular embodiments, the use of black or dark-colored polymers can decrease the noise by 50%, 75%, 85%, 90%, 95%, 99% or more. In other embodiments, the use of white, undyed, or reflective materials can serve to increase the signal to noise ratio by increasing the signal reflection within the amplification-detection chamber. For example, in some embodiments, the use of a reflective surface such as aluminum can increase the signal by a factor of 2 and in other embodiments, the use of a white or undyed polymer can increase the signal by a factor of 2.5, 3.0, 3.5, 4.0, 4.5, 5.0 or more.) Flexibility: R=Rigid, F=Flexible.

When paraplexing is performed and (in some embodiments) detection occurs in the endcap region, it may be preferable to select a piston cross-sectional profile that resists axial rotation to minimize shear forces and, depending on the conformation, unintended mixing. Without an insert, multiple pistons (or a divided piston) may operate in parallel to process the reactions. In some embodiments, with an insert, such as the reaction chamber insert 300, a single piston face may drive multiple reactions which are segregated by divisions within the insert in either a plane parallel to the piston face, or through multiple such planes arranged in a stack.

The length of the piston can affect the heat transfer from the higher temperature end to the lower temperature end of the device. In some embodiments, the length of the piston may be shortened to approach an equilibrium point such that passive heat transfer from the higher temperature side is sufficient, or nearly sufficient to raise the lower temperature side to the desired set point. It is preferable to have a margin of safety such that at maximum device tolerances in maximum allowable environmental operating parameters, the lower temperature side will preferably contribute at least 1%, but more preferably 3%, 5%, or 10% of the heat otherwise required to maintain the device's lower temperature side at the desired set temperature given environmental conditions. The second end 152 may optionally include a heat sink or heat shield, including communication voids which contain air allowing convective cooling, fins or projections for radiant cooling, cooling (heat) pipes, chemical cooling, or other methods that will be apparent to the practitioner, or combinations of these including active and passive cooling.

As a further enhancement, and as an alternative embodiment to heating sources at the higher and lower temperature zones, the design may dynamically adjust the proportion of heat directed to the higher and lower temperature sides from a single heat source by adjusting the contact surface area between the heat source and the first end or the second end or both to optimize heat transfer proportion (and hence power usage) based on environmental conditions or sample characteristics. The control of such optimization will be apparent to a practitioner and may include mechanical and electromotive methods, as well as self-regulating materials such as bimetallic alloys, and phase-change compounds which are calibrated to alter their surface contact area in inverse proportion to the fraction of heat received.

The composition, density, geometry, thermal conductance of the piston may be optimized to produce different optimized embodiments. In one embodiment, to optimize the geometry of the piston, account for the differential volumes between the cylinder and the piston, and calculate the total volume as the difference between the cylinder volume and the piston (less the volume created by the piston-cylinder tolerance, and capillary volume, if present). The reaction volume is calculated as the cylinder of fluid abutting the cylinder wall opposite the wall engaged by the piston, less any volume occupied by any exposed O-rings or protrusions, asperities, or ribs. The dead space is calculated by subtracting reaction volume from the total volume, and the dead space percentage as the quotient of the dead space over the total volume.

In certain embodiments, the dead space can be less than 35%, 25%, 20%, even more particularly below 15%, 10%, 5% or lower, bounded by the ability of the piston to substantially traverse the linear stroke length of the housing, with a stroke length traverse time of less than 5 seconds, or more particularly less than 4 seconds, 3 seconds, 2 seconds, 1 second, 500 milliseconds, 250 milliseconds, 100 milliseconds, or less, with the lower bound stroke length traverse time constrained by the sum of the heat transfer time as previously discussed and the required minimal chemical reaction time of the amplification method used. For example, in polymerase chain reaction, it is feasible to achieve rapid cycle durations (for example, less than 10 seconds, 9 seconds, 8 seconds, 7 seconds, 6 seconds, 5 seconds, 4 seconds, 3 seconds, 2 seconds, 1 second, 500 milliseconds, 250 milliseconds, 100 milliseconds per half cycle, which, in turn, would equate to total PCR reaction time equal to the product of the cycle time and the number of cycles, for instance, 10 cycles, 15 cycles, 20 cycles, 25 cycles, 30 cycles, 35 cycles, 40 cycles, 45 cycles, and 50 cycles, or more; accordingly, for example, total PCR reaction times may be as fast as less than 1 minute, or about 2, 3, 4, 5, 6, 7, 8, 9, 10, 11, 12, 13, 14, 15, 16, 17, 18, 19, 20, 21, 22, 23, 24, 25, 26, 27, 28, 29, or 30 minutes, or about between 30-35 minutes, 35-40 minutes, about between 40-45 minutes, about between 45-50 minutes, about between 50-55 minutes, about between 55-60 minutes, or more) by increasing the concentration of the reactants at lower volumes (see Farrar, "Extreme PCR: Efficient and Specific DNA Amplification in 15-60 Seconds", Clinical Chemistry 2015; see also U.S. Pat. No. 9,932,634, incorporated herein by reference), as well as other approaches to optimize amplification discussed herein.

In some embodiments, the device may be connected, via wireless connection, blue tooth, USB cable or other suitable mechanism, to a smart phone, tablet computer, computer, or other similar device (hereinafter, a "Companion Device"). While such a Companion Device may, as noted previously, function to provide power to the device, it may also function to allow the device to operate without a display screen and with dramatically reduced memory and processing power, as the Companion Device would be able to supply such memory. In such an embodiment, the device may also function with a companion application (or app) that would run on the Companion Device. In this way, the device could be produced at significantly less cost, while still retaining the key feature of portability.

In some embodiments, the polymerase enzymes used may be modified to provide shorter PCR cycle times, or shorter overall PCR times, or other attributes such as higher fidelity, robustness, lower cost or compatibility with materials, reagents, or sample components. For example, high processivity enzymes, or fast polymerases, or tightly bonding enzymes, or enzymes which include endo or exonuclease functions may be used. For example, many PCR polymerases function near 1 kilobase per minute in speed. In embodiments where the target of interest is, for example 200 bp, this equates to a polymerase time of approximately 12 seconds (200 bp/1000 bp*60s). Incorporating a fast polymerase of, for example 5 kilobase per minute speed, would decrease the polymerase time to 2-3 seconds for a similarly sized target. Polymerases may be from various thermophilic micro-organisms, including *Thermus aquaticus* (Taq), *Pyrococcus furiosus* (Pfu polymerase), *Thermococcus litoralis* (Wind or Tli polymerase or Vent polymerase) and *Thermus thermophilus* (Tth polymerase). (Drouin et al., DNA polymerases for PCR applications, J. Polaina and A. P. MacCabe (eds.), *Industrial Enzymes,* 379-401, 2007). Polymerases may be selected for 5' to 3' polymerase activity, 3' to 5' exonuclease proofreading activity, or 5' to 3' exonuclease nick translation activity. Exemplary polymerases include but are not limited to DNA polymerase I, Klenow Fragment of DNA polymerase I (e.g., labelling recessed 3' end of double stranded DNA), Taq DNA polymerase (e.g., for DNA labeling), T4 DNA polymerase (e.g., for forming blunt ends), terminal transferase (e.g., for tailing and labeling 3-OH ends), Deep Vent® (e.g., for high-fidelity), Pfu DNA polymerase (e.g., for primer-extension), Herculase® enhanced Phusion™ Sequenase™ DNA polymerase I, rTh DNA polymerase XL, Isis proofreading polymerase, rBst DNA polymerase, phi29 DNA polymerase (e.g., rolling circle replication), SurePRIME™ DNA polymerase, BioTHERM™ DNA polymerase, SpeedSTAR™ HS DNA polymerase, MTP™ Taq DNA polymerse, and KOD "Host Start" DNA polymerase.

In some embodiments, Deep Vent® or other higher temperature enzymes (such as those isolated from *T. litoralis* or similar species) may be used which allow for increased half-life times at lower concentrations during polymerization reactions. In addition, combinations of multiple enzymes, or combinations which optimize for these traits, or for example, with isothermal amplification and rtPCR can serve to improve efficiency, particularly with RNA targets, or targets with unusual base-pair content, such as high GC content, or sequences with highly repetitive segments. Other technologies may also be included, such as the use of targeted endonucleases to discriminate SNPs and subtle target sequences. Such targeted endonucleases include, but are not limited to CAS/CRISPR, TALENs, ZFNs, as well as any of the rapidly available molecular biology tools which permit high-fidelity programmable targeting of sequences of interest (Batista and Pacheco, Detecting pathogens with Zinc-Finger, TALE and CRISPR-based programmable nucleic acid binding proteins, Journal of Microbiological Methods, 152: 98-104, 2018).

For example, in some embodiments, the discrimination of SNPs or subtle target sequences is carried out by fusion proteins that comprise DNA-binding proteins and a heterologous regulatory domain or functional fragment thereof. In some aspects, domains include, e.g., transcription factor domains such as activators, repressors, co-activators, co-repressors, silencers, oncogenes, DNA repair enzymes and their associated factors and modifiers, DNA rearrangement enzymes and their associated factors and modifiers, chromatin associated proteins and their modifiers, e.g. kinases, acetylases and deacetylases, and DNA modifying enzymes, e.g. methyltransferases, topoisomerases, helicases, ligases, kinases, phosphatases, polymerases, endonucleases, and their associated factors and modifiers. See, for example, U.S. Patent Application Publication Nos. 2005/0064474; 2006/0188987 and 2007/0218528, incorporated by reference in their entireties herein.

In some embodiments, the Zinc-Finger Proteins (ZFPs) are artificial ZFP domains targeting specific DNA sequences, typically 9-18 nucleotides long, generated by assembly of individual fingers. ZFPs include those in which a single finger domain is approximately 30 amino acids in length and contains an alpha helix containing two invariant histidine residues coordinated through zinc with two cysteines of a single beta turn, and having two, three, four, five, or six fingers. Generally, sequence-specificity of a ZFP may be altered by making amino acid substitutions at the four helix positions (−1, 2, 3 and 6) on a zinc finger recognition helix. Thus, in some embodiments, the ZFP or ZFP-containing molecule is non-naturally occurring, e.g., is engineered to bind to a target site of choice. See, for example, Beerli et al., 2002; Pabo et al., 2001; Isalan et al., 2001; Segal et al., 2001; Choo et al., 2000; U.S. Pat. Nos. 6,453, 242; 6,534,261; 6,599,692; 6,503,717; 6,689,558; 7,030, 215; 6,794,136; 7,067,317; 7,262,054; 7,070,934; 7,361, 635; 7,253,273; and U.S. Patent Publication Nos. 2005/0064474; 2007/0218528; 2005/0267061, all incorporated herein by reference in their entireties.

In some embodiments, the TALEN is a fusion protein comprising a DNA-binding domain derived from a TALE and a nuclease catalytic domain to cleave a nucleic acid target sequence. In some embodiments, TALE repeats are assembled to specifically target a gene. (Gaj et al., 2013). A library of TALENs targeting 18,740 human protein-coding genes has been constructed (Kim et al., 2013). Custom-designed TALE arrays are commercially available through Cellectis Bioresearch (Paris, France), Transposagen Biopharmaceuticals (Lexington, KY, USA), and Life Technologies (Grand Island, NY, USA).

In some embodiments, a CRISPR/Cas system is used including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), and/or other sequences and transcripts from a CRISPR locus. The CRISPR/Cas nuclease or CRISPR/Cas nuclease system can include a non-coding RNA molecule (guide) RNA, which sequence-specifically binds to DNA, and a Cas protein (e.g., Cas9), with nuclease functionality (e.g., two nuclease domains). One or more elements of a CRISPR system can derive from a type I, type II, or type III CRISPR system, e.g., derived from a particular organism comprising an endogenous CRISPR system, such as *Streptococcus pyogenes* (US20110059502 and U.S. Pat. No. 8,795,965, both incorporated herein by reference).

Decreasing reaction volumes may have a more than additive (i.e., synergistic) effect on the efficiency of piston-based amplification by decreasing heat transfer time and chemical reaction time. As these factors contribute to increasingly faster reactions in a piston-based device as the volume decreases, they can be bounded by two primary factors, namely sensitivity and proportion of dead space to total reaction volume. The effect of sensitivity, as discussed elsewhere, can be mitigated by several approaches in the ingress module, including sample preparation methods that concentrate nucleic acids of interest, as will be well familiar to the practitioner. The ratio of dead space affects the efficiency of the amplification reaction, with higher proportions of dead space lowering the reaction order from an idealized second order (wherein the PCR reaction doubles each thermal cycle) towards a first order (linear) reaction speed. However, since the more than additive benefits of smaller reactions are also higher order effects (depending on the mode used to achieve higher heat transfer, the rate is proportional to the surface area, inverse of the distance, and thermal conductivity), it can be preferred in certain embodiments to determine the local minimum for amplification time which corresponds to the preferred volume of the reaction, and in turn the geometric parameters required to achieve this.

As total volume of the reaction space increases, the relative percentage of dead space decreases, yielding an amplification efficiency which more closely approaches ideal doubling (understanding that measured efficiencies of qPCR can exceed 100% if contaminants, concentrated samples, or other artifacts suppress the early $\Delta$Ct values, artificially increasing the yield curve), however this can be bounded by several constraints. First, as the reaction volume increases, the amount of heat and the time required for heat transfer both increase, imposing additional design requirements if amplification time is to remain constant. Second, increased volumes can require increased sample sizes. This is not typically a constraint of clinical samples, but can be with lysis modules which include a concentration step, or with experimental samples. Third, increased volume typically increases reagent cost, and to some extent, manufacturing time and material costs. Additionally, amplification reactions can become unreliable at higher volumes due to macrovolumetric effects during amplification. Accordingly, in some embodiments, the reaction volume can be less than 500 µL, more particularly below 250 µL, 150 µL, 100 µL, 50 µL, 25 µL, 15 µL, 10 µL, 5 µL, 1 µL, or less.

In particular embodiments, sample port 155 may be a floating piston configuration with a collection piston, where the advancement of the collection piston serves to close the ingress port, advance the sample fluid, and express the sample fluid into the next phase to minimize the entrance of air and the manual steps required, for example in some embodiments, 275. The sample fluid may also be mixed with the lysis reagents at this stage to complete extraction and purification, or alternatively pre-loaded in liquid, lyophilized, powdered or other forms.

In some embodiments, prior to amplification nucleic acids may be purified, isolated or extracted from biological samples. To release the contents of cells or viral particles, they may be treated with enzymes or with chemicals to dissolve, degrade or denature the cellular walls or viral particles. In other embodiments, lysis may be effected through osmotic or oncotic pressure or heating. In other embodiments, the sample may be contacted with chaotropic agents such as guanidinium thiocyanate or anionic, cationic, zwitterionic or non-ionic detergents, proteases which rapidly degrade the previously described enzymes or unwanted proteins, such as alkaline proteases, acid proteases, or proteinase K.

In certain embodiments utilizing PCR and RT-PCR process, the lysis of the sample can be performed chemically utilizing: a lyophilized formulation; Protease (Serine proteases like Protease K, cysteine proteases, threonine proteases, aspartic proteases, glutamic proteases, metalloproteases, asparagine peptide lyases), particularly 0.05 to 2 µg per reaction (or more particularly 0.5 to 1 µg per reaction); RNAse Inhibitor (particularly more than 0.1 units per microliter of reaction volume, even more particularly 1 unit per microliter of reaction volume); and optionally, a bacteriase (particularly more than 0.05 units per microliter of reaction volume). In some embodiments, the lysis buffer comprises buffering agents, chaotropic salts, ionic detergents, non-ionic detergents solvents, EDTA, Trizol, monovalent and/or divalent salts. Buffers for use may include, but are not limited to $H_3PO_4/NaH_2PO_4$, Glycine, Citric acid, Acetic acid, Citric acid, MES, Cacodylic acid, $H_2CO_3/NaHCO_3$, Citric acid, Bis-Tris, ADA, Bis-Tris Propane, PIPES, ACES, Imidazole, BES, MOPS, $NaH_2PO_4/Na_2HPO_4$, TES, HEPES, HEPPSO, Triethanolamine, Tricine, Tris, Glycine amide, Bicine, Glycylglycine, TAPS, Boric acid ($H_3BO_3/Na_2B_4O_7$), CHES, Glycine, $NaHCO_3/Na_2CO_3$, CAPS, Piperidine, $Na_2HPO_4/Na_3PO_4$, and combinations thereof. In other embodiments, the lysis may be performed by heat, microwave, or physical dissociation (e.g. silica-based filters or graters). Lyophilized components at any stage within the modules may be contained alongside liquid components, provided they are separated by a thin film which is perforated during operation or later joined by any of the fluid channel division methods described herein. For example, lyophilized PCR reagents may be located within the piston capillary, in the endcaps or cylinder, and perforated upon movement of the piston relative to the cylinder or endcaps. In a similar fashion, lyophilized lysis reagents may be contained (optionally alongside liquid reagents or carrier solutions) within a swab handle, or the corresponding receptive portion of the ingress module such that a lancet or other mechanical penetration of the compartment allows mixing of the two elements, or mixing is effected by other methods mentioned elsewhere herein.

In certain embodiments, reaction fluid 175 can be thermally cycled in a PCR process in which the reagents include a lyophilized formulation, one bead of PCR mastermix formulation (e.g. Jena Bioscience, GmbH; contains all of the components necessary to perform PCR, including Taq DNA polymerase, 0.5-10 mM magnesium chloride, 10-100 mM potassium chloride, 5-50 mM ammonium sulfate, and additives and stabilizers required to achieve lyophilization, which may include one or more items from the following group of compounds: poly(lactic-co-glycolic) acid, polyethylene glycol, polyethylene oxide, poly(caprolactone), poly (lactide), poly(glycolide), poly(orthoesters), and poly(hydroxybutyrate), fructose, erythrose, threose, ribose, arabinose, xylose, lyxose, allose, altrose, glucose, idose, galactose, erythrulose, ribulose, xylulose, psicose, fructose, sorbose, tagatose, fructofuranose, ribofuranose, ribose, deoxyribose, mannitol, and sialic acid, sucrose, lactose, maltose, cellobiose, trehalose and lactulose, starch, glycogen, cellulose, chondroitin, keratin, heparin, dermatan, and hyaluronic acid), 2-10 mM MgCl2, 50-900 nM of forward and reverse assay primers, 50-400 nM of detection probe, and 1 micromolar to 10 millimolar of protease K inhibitor (AAPF, AAPV, AAPA; other inhibitors may include: AEBSF, 6-Aminohexanoic acid, Antipain, Aprotinin, Benzamidine HCl, Bestatin, Chymostatin, E-64, N-Ethylmaleimide, Leupeptin, Pepstatin, Phosphoramidon, Trypsin inhibitor). In particular embodiments, reaction fluid 175 may be thermally cycled in a RT-PCR process. In one specific embodiment, the reagents used for RT-PCR can include a lyophilized formulation, one bead of PCR mastermix formulation, 2-10 mM MgCl2, 50-900 nM of forward and reverse assay primers, 50-400 nM of detection probe, 10-500 μM of protease inhibitor and a reverse transcriptase formulation (0.05-2 units per microliter of reaction volume). Chemical additive or co-solvents may be included in the PCR mastermix, such as excipients and/or stabilizers. For example, 1-10% dimethyl sulfoxide (DMSO), 5-20% glycerol, 1.25-10% formamide, 10-100 μg/mL bovine serum albumin (BSA), 15-30 mM ammonium sulfate, 5-15% polyethylene glycol (PEG), 0.01% gelatin, 0.05-0.1% nonionic detergents (e.g., Tween 20, Triton X-100), or 1-3 M N,N,B-trimethylglycine (betaine) (Bartlett J M S, Stirling D (2003) PCR Protocols. In: Methods in molecular biology (2nd ed). Totowa: Humana Press). In some embodiments, PCR inhibitors such as polyphenols, humic and fulvic acids may be used.

In certain embodiments illumination module 133 and a detection module 135 can be used to illuminate and detect analytes present in reaction fluid 175 before, during, or after, the thermal cycling process. For example, reagents 173 may comprise components that react, bind to, or otherwise modify particular target molecules or sequences in sample 170. In certain embodiments, such analytes may emit fluorescent or chemiluminescent signals that can be detected by detection module 135. It is understood the location of illumination module 133 and a detection module 135 shown in FIG. 1 is for exemplary purposes, and other embodiments may comprise a different location of illumination module 133 and a detection module 135. In the embodiment shown, apparatus 100 comprises a display 196 (e.g. a liquid crystal display) configured to display results from analysis and diagnosing sample 170. Apparatus 100 can also comprise one or more control elements 197 (e.g. buttons, switches, etc.) to allow a user to control apparatus 100 (e.g. initiate or cease operation of apparatus 100). In particular embodiments, apparatus 100 may comprise a single control element 197 (e.g. a start button) that allows a user to initiate operation of apparatus 100, with all subsequent aspects of control performed automatically by controller 195.

In certain embodiments, it can be preferable during operation to allow a wide range of biological sample volumes, with the minimum detectable volume (set by the concentration of the analyte which is relevant to the test performed on the device) serving as a floor, and the upper range constrained by the portability, cost, and other commercial aspects of the intended use. Because of factors mentioned herein, the typical range of biological sample volumes is can be at least 10 μL, or more particularly 50 μL, 100 μL, 250 μL, 500 μL, 1 mL, or more, and volumes greater than 5 mL, 7 mL, or 10 mL can be concentrated, or if concentration is not employed, contain sufficient target analyte to allow direct lysis, amplification, and detection.

In a particular embodiment, a carrier fluid is utilized which dilutes the sample fluid. This carrier fluid diluent may contain lysis reagents, or a subset of the PCR reagents (e.g. primers), and may dilute the sample fluid at a ratio of 1:2, 1:3, 1:4, 1:5, 1:6, 1:7, 1:8, 1:9, or more particularly at a ratio of 1:10. In other embodiments, the ratio can be up to 1:15 or more. In certain embodiments where the sample fluid is saliva, the ratio can be between 1:9 and 1:15. In certain embodiments, the dilution can be preferable for sample fluids which are viscous, contain inhibitors of the amplification chemistry employed, or contain an abundance of target analyte, most particularly if quantitative or semi-quantitative detection methods are used. In some embodiments, mechanical filters are present which exclude or limit debris, or with smaller pore filters, long-chain chemicals, or those with particular charge or size from passing.

During operation of some embodiments, it can also be desirable to extract a fixed volume from the above-mentioned minimum and maximum target volumes, so that the concentration of chemistries in those fixed, or more tightly ranged volumes are similarly ranged for the lysis fluid, reaction fluid, and detection fluid. In some embodiments, it can be preferable to obtain a lysis fluid which varies in volume no more than 30%, but even more particularly less than 25%, 20%, 15%, 10%, 5%, 3%, 1%, or less, and to obtain a reaction fluid with a volume that varies less than 20%, but even more particularly less than 15%, 10%, 7.5%, 5%, 3%, 1%, or less.

As the detection fluid is primarily a subset element of the reaction fluid, which is in turn an element of the lysis fluid, which in turn is an element of the sample fluid (and, optionally, any carrier or diluent fluid incorporated), understanding that each fluid will additionally contain liquid or dry (e.g. lyophilized) reagents which may increase volume at that stage, and that maintaining fixed volumes within a range (as discussed above) is preferable, the management of surplus/waste fluid from each stage in some embodiments is accomplished by inclusion of a either an overflow chamber, or by employing a division in the fluid column such that the volume of the ingress fluid is diminished (or an minimum not increased) at each stage, the aforementioned reagent additions notwithstanding. The overflow chamber, in embodiments where it is included, may optionally contain absorbing material or sensors to indicate entrance or saturation of the chamber.

Division of the fluid column may be accomplished in several different embodiments, in different modules (e.g. ingress, lysis, combined amplification/detection, [also referred to herein as "amplitection"]) including, but not limited to the use of heat or chemical sealing of channels, mechanical compression or expansion including screw or twist compression, press fit, or temperature-assisted modes, for instance by relying on the thermal expansion of components to tighten the fit of components or fluid pressure to more tightly seal check valves, ball, rotational, or other valves, actuators, melting or solidifying substances which may be regulated by mechanical processes, the control 195, sensors, or may be triggered directly by action of the fluid channel.

As discussed with the embodiment of the piston insert, air management can be important for the entirety of the fluid channel, and excess air (and generally gas) may be handled through various embodiments, including use of vacuum/evacuated compartments within the modules, understanding that while a vacuum of 90%, 95%, 97%, 99% or greater can be preferred in some embodiments, that lower percentages may be employed if combined with the other methods described herein. Other such embodiments include using liquid pre-filled modules, incorporating a flow-through aspect to the invention whereby the air advancing ahead of the fluid column may pass through the module, and the egress may be closed and overflow managed (as mentioned above) using several methods, and thereby forming a module containing the fluid appropriate for the module of sufficiently high volume and of sufficiently low gas to liquid ratio.

In other embodiments, methods of absorbing air components include the use of oxygen and other gas absorbing compounds or materials, iron based, non-ferrous oxygen scavengers (e.g. Kerry, Joseph; Butler, Paul (May 23, 2008). Smart Packaging Technologies for Fast Moving Consumer Goods. Wiley & Sons., incorporated herein by reference), and alloys or compounds that may operate at room temperature and pressure, or require higher temperature exposures (e.g. U.S. Pat. No. 8,211,202, incorporated herein by reference). When using chemical, in particular ferrous-based, absorbers, it can be desirable in some embodiments to incorporate the scavenger in a polymer or alloy structure to prevent later inhibition of PCR chemistry.

Certain embodiments are designed to accept or manage air which is present. This can be accomplished by addressing a central challenge in piston-based PCR, which is the management of the liquid—gas boundary. With amplification methods that use higher temperatures to dissociate nucleic acids (e.g. PCR), an aqueous solution is frequently near the boiling point of water, or greater than approximately 90° C. at standard pressures and correspondingly higher temperatures at higher pressures and correspondingly lower temperatures at lower pressures according to gas laws which will be familiar to the practitioner. Although primer design can provide lower dissociation temperatures, when extracting or targeting analytes within genomic DNA, or other chemistries where near-boiling temperatures are preferred for optimal dissociation of DNA and denaturation of proteins, it can be desirable to increase the pressure of the reaction to avoid flash-boiling. The use of a pressure vessel is can be desirable in some embodiments, optionally including a pressure relief aspect for safety.

Tight temperature control can also be desirable in some embodiments, with control loops allowing no more than a 10%, or more particularly, no more than a 7%, 6%, 5%, 4%, 3%, 2%, or 1% variance being even more preferred. This can allow the device to operate at a setpoint closer to its maximum allowable temperature, which can be important not only from a materials standpoint, but because the efficiency of amplification can decrease above particular temperatures, even if the boiling point is increased by means of additional pressure (e.g. see Drouin et al., DNA polymerases for PCR applications, J. Polaina and A. P. MacCabe (eds.), *Industrial Enzymes*, 379-401, 2007; see also https://www.neb.com/tools-and-resources/selection-charts/thermophilic-dna-polymerases, each incorporated herein by reference). For DNA polymerases which contain 5' to 3' exonuclease activity, which is required for TaqMan detection, it can be to maintain the reaction temperature below 99.9° C., more preferable below 99.5° C., 99° C., 98° C., or lower as allowed by the particular target of interest. For detection methods that do not rely on the above mechanisms, higher temperature polymerases (operating at 100° C. to 105° C. or higher) can be desirable.

In certain embodiments, apparatus 100 is configured as an amplification or replication module, or thermocycler capable of thermal cycling, including cyclic heating which uses polymerase chain reaction (PCR), quantitative PCR (qPCR), real-time PCR, reverse transcriptase PCR, or other suitable thermocycling either via space-domain or time-domain formats.

In certain embodiments, reaction fluid 175 may comprise primers, oligonucleotides, buffers, dNTPs (deoxyribonucleotide triphosphates), rNTPs (ribonucleotide triphosphates), probes, salts, monovalent cations, potassium, bivalent cations, magnesium (Mg), manganese (Mn), aptamers, hydrolysis probes (e.g. TaqMan probes), dual-labeled probes, scorpions probes, Taq polymerase, molecular beacons, colorimetric indicators, DNA binding or reporter dyes (e.g. SYBR green), gold nanoparticles, fluorescence, or reverse transcriptase. In some embodiments, the probes are ATTO647, FAM™, HEX™ TET™, JOE™ TAMRA™, Texas Red®, VIC®, NED™, ROX™, PET®, Cy, rhodamine, ATTO, or other similar probes. The principles of selecting and combining probes for multiple channels (i.e. multiplexing) will be familiar to practitioners. The preferred probe for a particular assay should incorporate consideration of quantum yield, or the ratio of energy in to energy out, with a quantum yield of 1.0 being 100%, and quantum yields less than this indicating a fraction of the energy return in the desired wavelength(s). It should be noted that although many dyes are described in terms of their maximum absorption or emission wavelengths, the actual curves often differ depending on a number of factors, and consideration of high and low bandpass wavelengths should include "shoulders" or sub-maximal wavelength frequencies as well as the signal overlap due to different dyes. See the following references related to probe and dye selection and combination, incorporated herein by reference:

https://www.idtdna.com/pages/products/custom-dna-rna/oligo-modifications/fluorophores/freedom-dyes Prediger, Recommended dye combination for multiplex PCR, Integrated Data Technologies, 2018.

Prediger, qPCR Probes—selecting the best reporter dye and quencher, Integrated Data Technologies, 2015.

In some embodiments, primers are from 12 to 35 nucleotides in length (e.g., 12-20, 20-25, 25-30, or 30-35 nucleotides in length), such as from 15 to 20 nucleotides in length. Primers may be designed from known parts of the template, one complementary to each strand of the double strand of the template nucleic acid molecule, lying on opposite sides of the region to be synthesized. Primers can be designed and synthetically prepared as is well known in the art. Primers may be modified to reduce non-specific hybridization (U.S. Pat. No. 6,001,611, incorporated herein by reference). In some embodiments, hot-start primers may be used to reduce non-specific reactions and may comprise a stem-loop or hairpin-like structure (U.S. Pat. No. 6,482,590, US Pat. App. No. 2007/0128621). Chemical modifications of primers may include but are not limited to glyoxal, derivatives thereof, 3,4,5,6-tetrahydrophthalic anhydride, 3-ethoxy-2-ketobutyraldehyde (kethoxal), ninhydrin, hydroxyacetone, diethyl oxalate, diethyl mesoxalate, 1,2-naphthoquinone-4-sulfonic acid, pyruvaldehyde, amides, γ-carboxyacylamides, amidines, and carbamates. In certain embodiments, nucleotide analogues that may be used include derivatives wherein the sugar is modified, as in 2'-O-methyl, 2'-deoxy-2'-fluoro, and 2',3'-dideoxynucleoside derivatives, nucleic acid analogs based on other sugar backbones, such as threose, locked nucleic acid derivatives, bicyclo sugars, or hexose, glycerol and glycol sugars, nucleic acid analogs based on non-ionic backbones.

In certain other embodiments, the reaction fluid may employ alternative detection methods to be detected by module 135, including dsDNA-binding dyes, hydrolysis probes, hybridization probes, nucleotide analogs, pH changes, colorimetric indicators, luminescent indicators, or electrochemical modes of detection. For example, the mode of detection may include SYBR green (Molecular Probes), SYBR-Gold, EvaGreen, Ethidium bromide, YO-PRO-1, SYTO, BEBO, BOXTO, TaqMan (Roche), i-probes, Eclipse probes, FRET, ATTO, PicoGreen, Snake, Molecular Beacons, aptamer beacons, PNA beacons, labeled LNA probes, antibody beacons, Scorpions Probe, LightCycler Probe, Hyprobe, HyBeacon, ResonSense, Yin-Yang, Amplifluor, LUX, Cyclicons, Angler, LNA, PNA, ZNA, Plexor primers, pH sensing using an ion-sensitive field effect transistor (ISFET), high-resolution melt curve analysis (HRM), or others. These techniques are summarized respectively in the following sources, which are incorporated herein by reference:

Schneeberger C, Speiser P, Kury F, Zeillinger R (1995) Quantitative detection of reverse transcriptase-per products by means of a novel and sensitive DNA stain. PCR Methods Appl 4:234-238

Tuma R S, Beaudet M P, Jin X, et al. (1999) Characterization of SYBR Gold nucleic acid gel stain: a dye optimized for use with 300-nm ultraviolet transilluminators. Anal Biochem 268:278-288.

Wang W, Chen K, Xu C (2006) DNA quantification using EvaGreen and a real-time PCR instrument. Anal Biochem 356:303-305.

Higuchi R, Dollinger G, Walsh P S, Griffith R (1992) Simultaneous amplification and detection of specific DNA sequences. Biotechnology 10:413-417.

Ishiguro T, Saitoh J, Yawata H, Yamagishi H, Iwasaki S, Mitoma Y (1995) Homogeneous quantitative assay of hepatitis C virus RNA by polymerase chain reaction in the presence of a fluorescent intercalater. Anal Biochem 229:207-213.

Monis P T, Giglio S, Saint C P (2005). Comparison of SYTO9 and SYBR Green I for real-time polymerase chain reaction and investigation of the effect of dye concentration on amplification and DNA melting curve analysis. Anal Biochem 340:24-34.

Bengtsson M, Karlsson H J, Westman G, Kubista M (2003) A new minor groove binding asymmetric cyanine reporter dye for realtime PCR. Nucleic Acids Res 31:e45.

H. J. Karlsson, P. Lincoln, G. Westman (2003) Synthesis and DNA Binding Studies of a New Asymmetric Cyanine Dye Binding in the Minor Groove of [poly(dA-dT)]2. Bioorganic & Medicinal Chemistry 11:1035-1040.

Holland P M, Abramson R D, Watson R, Gelfand D H (1991) Detection of specific polymerase chain reaction product by utilizing the 5'-*3' exonuclease activity of Thermus aquaticus DNA polymerase. Proc Natl Acad Sci USA 88:7276-7280

Kutyavin I V (2010) New approach to real-time nucleic acids detection: folding polymerase chain reaction amplicons into a secondary structure to improve cleavage of Forster resonance energy transfer probes in 5'-nuclease assays. Nucleic Acids Res 38:e29.

Tyagi S, Kramer F R (1996) Molecular beacons: probes that fluoresce upon hybridization. Nat Biotechnol 14: 303-8.

Whitcombe D, Theaker J, Guy S P, Brown T, Little S (1999) Detection of PCR products using self-probing amplicons and fluorescence. Nat Biotechnol 17: 804-807

Pals G et al., (2001) Detection of a single base substitution in a single cell using the LightCycler. J Biochem Biophys Methods, 47:121-129

Morrison L E, Halder T C, Stols L M (1989) Solution-phase detection of polynucleotides using interacting fluorescent labels and competitive hybridization. Anal Biochem 183:231-244.

French D J, Archard C L, Brown T, McDowell D G (2001). HyBeacon probes: a new tool for DNA sequence detection and allele discrimination. Mol Cell Probes 15:363-374.

Lee M A, Siddle A L, Page R H (2002) ResonSense®: simple linear fluorescent probes for quantitative homogeneous rapid polymerase chain reaction. Anal Chim Acta; 457:61-70.

Li Q, Luan G, Guo Q, Liang J (2002). A new class of homogeneous nucleic acid probes based on specific displacement hybridization. Nucleic Acids Res 30:e5.

Nazarenko I A, Bhatnagar S K, Hohman R J (1997) A closed tube format for amplification and detection of DNA based on energy transfer. Nucleic Acids Res 25:2516-2521.

Nazarenko I, Lowe B, Darfler M, Ikonomi P, Schuster D, Rashtchian A (2002) Multiplex quantitative PCR using self-quenched primers labeled with a single fluorophore. Nucleic Acids Res 30:e37.

Kandimalla E R, Agrawal S (2000) 'Cyclicons' as hybridization-based fluorescent primerprobes: synthesis, properties and application in real-time PCR. Bioorg Med Chem 8:1911-1916.

"Kutyavin I V (2013) Use of extremely short Förster resonance energy transfer probes in real-time polymerase chain reaction." Nucleic Acids Res. 41: e191.

Kaur H, Arora A, Wengel J, Maiti S (2006) Thermodynamic, counterion, and hydration effects for the incorporation of locked nucleic acid nucleotides into DNA duplexes. Biochemistry 45:7347-7355.

Nielsen P E, Egholm M, Berg R H, Buchardt O (1991) Sequence-selective recognition of DNA by strand displacement with a thymine-substituted polyamide. Science 254:1497-1500.

Pons B, Kotera M, Zuber G, Behr J P (2006) Online synthesis of diblock cationic oligonucleotides for enhanced hybridization to their complementary sequence. Chembiochem 7:1173-1176.

Sherrill C B, Marshall D J, Moser M J, Larsen C A, Daudé-Snow L, Prudent J R (2004) Nucleic Acid Analysis Using an Expanded Genetic Alphabet to Quench Fluorescence. J Am Chem Soc 126:4550-4556

U.S. Pat. No. 7,888,015B2

Liew M, Pryor R, Palais R, Meadows C, Erali M, Lyon E, et al. (2004) Genotyping of single-nucleotide polymorphisms by high-resolution melting of small amplicons. Clin Chem 50:1156-1164.

Richard P. Haugland, Handbook of Fluorescent Probes and Research Chemicals (6th ed. 1996).

https://www.ncbi.nlm.nih.gov/probe/docs/projtaqman/ https://www.idtdna.com/pages/education/decoded/article/designing-pcr-primers-and-probes http://tools.thermofisher.com/content/sfs/manuals/cms_041902.pdf Some non-limiting examples of probes for detection include fluorophores, radioisotopes, chromogens, enzymes, antigens including but not limited to epitope tags, semiconductor nanocrystals such as quantum dots, heavy metals, dyes, phosphorescence groups, chemiluminescent groups, electrochemical detection moieties, binding proteins, phosphors, rare earth chelates, transition metal chelates, near-infrared dyes, electrochemiluminescence labels, and mass spectrometer-compatible reporter groups, such as mass tags; charge tags, and isotopes (see, e.g., Haff and Smirnov, Nucl. Acids Res. 25:3749-50, 1997; Xu et al., Anal. Chem. 69:3595-3602; 1997; Sauer et al., Nucl. Acids Res. 31:e63, 2003). Multi-element probe systems, including without limitation, affinity tags such as biotin:avidin, antibody:antigen, and the like, in which one element interacts with one or more other elements of the system in order to effect the potential for a detectable signal may be used. Some non-limiting examples of multi-element probe systems include an oligonucleotide comprising a biotin reporter group and a streptavidin-conjugated fluorophore, or vice versa; an oligonucleotide comprising a DNP reporter group and a fluorophore-labeled anti-DNP antibody; and the like. Fluorophore-quencher pairs, including without limitation fluorescent quenchers and dark quenchers (also known as non-fluorescent quenchers) may be used. Some non-limiting examples of dark or nonfluorescent quenchers include Dabcyl, Black Hole Quenchers, Iowa Black, QSY-7, AbsoluteQuencher, Eclipse non-fluorescent quencher, certain metallic particles such as gold nanoparticles, and the like. Phycobiliproteins including R-Phycoerythrin, B-Phycoerythrin, C-Phycocyanin, and Allophycocyanin (Hu, Production of potential coproducts from microalgae, Biofuels from Algae, 2019) and luciferins including firefly, latia luciferin, bacterial luciferin, coelenterazine, dinoflagellate, vargulin, and 3-hydroxy hispidin may be used. In some embodiments, the probes are conjugated or bound to one or more surfaces and may function as capture probes, including with the addition of wash or elution steps as will be familiar to one of skill in the art. In some embodiments, they may be arranged in orientations and patterns to allow differential detection based on their proximity to photodetector elements.

In some embodiments, suitable labels for detection may include fluorescein (FAM), digoxigenin, dinitrophenol (DNP), dansyl, biotin, bromodeoxyuridine (BrdU), hexahistidine (6×His), phosphor-amino acids (e.g., P-tyr, P-ser, P-thr), luciferin, rhodamine, phycobiliprotein, or any other suitable label. In some embodiments, detection is performed using CRISPR-Cas13a/C2c2-mediated cleavage of a reporter RNA, such as by the specific high-sensitivity enzymatic reporter unlocking platform (Gootenberg et al., Nucleic acid detection with CRISPR-Cas13a/C2c2, Science, 356(6336): 438-442, 2017; Myhrvoid et al., Field-deployable viral diagnostics using CRISPR-Cas13, Science, 360 (6387), 444-448).

In certain embodiments, detection is performed using electric field proximity sensing (EFPS), which relies on the fact that an electric field can be perturbed by the existence of a nearby object, provided it is at least slightly conductive (see, for example, de la Rica, Selective Detection of Live Pathogens via Surface-Confined Electric Field Perturbation on Interdigitated Silicon Transducers, Anal. Chem. 2009, 81, 10, 3830-3835). In some embodiments, melt curve analysis may be used for detection by assessing the dissociation characteristics of double-stranded DNA during heating, such as for the detection of single-nucleotide polymorphisms (Farrar et al., High-resolution melting curve analysis for molecular diagnostics, Molecular Diagnostics, $2^{nd}$ edition, 2010).

In some embodiments, turbidity analysis is performed by measuring the cloudiness or decrease in transparency. Light scattered by particles such as microorganisms may enable the detection of these particles in water (Omar and MatJafri, Turbidimeter Design and Analysis: A Review on Optical Fiber Sensors for the Measurement of Water Turbidity, Sensors (Basel). 2009; 9(10): 8311-8335).

In certain embodiments, lateral flow tests or lateral flow immunochromatographic assays may be used for detection. Lateral flow analysis may comprise cellulose-based detection of the presence of a target analyte in a sample based on a series of capillary beds, such as pieces of porous paper, microstructured polymer, or sintered polymer (Urusov et al., Towards Lateral Flow Quantitative Assays: Detection Approaches, Biosensors (Basel). 2019 September; 9(3): 89). The lateral flow analysis can use detectors that register colored, fluorescent, magnetic, or conductive labels.

In some embodiments, toehold probes may be used for nucleic acid detection (Toehold Probes for Nucleic Acid Detection, New molecular probe can distinguish DNA and RNA sequences with unprecedented accuracy, Wyss Institute, 2012). Toehold Probes may contain two strands of DNA that are hybridized to each other due to complementary of their nucleotide sequences. One, the "probe strand" is also complementary to a target sequence, for example, in the human genome, while the second "protector strand" copies part of the target DNA. Toeholds—short sequences at the ends of the probe strand that are either complementary to the target sequence or the protector strand—can initiate two exchange reactions. These either result in the probe strand being specifically bound to its target DNA/RNA/XNA (to allow its detection) and the protector strand being released; or, in reverse, in the probe strand re-engaging with the protector strand and leaving the target DNA/RNA/XNA behind. The two competing exchange reactions can lead to an equilibrium that is highly predictable and highly sensitive to perturbations such that the presence of a single non-matching nucleotide (a variant) in the target sequence prevents its detection.

Molecular beacons are hairpin-shaped oligonucleotide probes that become fluorescent upon hybridization to an RNA or DNA or XNA target sequence. Their loops serve as probes and are about 15 to 25 nucleotides long. Their stems serve to bring the two ends of the molecule, which are linked to a fluorophore and a quencher, into close proximity. Although the stems are only 5 to 7 nucleotides long, they keep the labels in close proximity so that the fluorescence of the fluorophore is quenched in the free probes (Tyagi and Kramer, F1000 Med Rep. 2012; 4:10). Molecular Beacons and other probes suitable for real-time PCR typically include a fluorescent reporter molecule at the 5'-end and a quencher molecule at the 3'-end. Probes modified with any one of an extensive group of fluorophores are commercially available. Commercially available fluorescent nucleotide analogues include, for example, Cy3-dCTP, Cy3-dUTP, Cy5-dCTP, Cy5-dUTP (Amersham Biosciences, Piscataway, N.J., USA), fluorescein-12-dUTP, tetramethylrhodamine-6-dUTP, Texas Red®-5-dUTP, Cascade Blue®-7-dUTP, BODIPY® FL-14-dUTP, BODIPY®-14-dUTP, BODIPY®TR-14-dUTP, Rhodamine Green™-5-dUTP, Oregon Green® 488-5-dUTP, Texas Red®-12-dUTP, BODIPY® 630/650-14-dUTP, BODIPY® 650/665-14-dUTP, Alexa Fluor® 488-5-dUTP, Alexa Fluor® 532-5-dUTP, Alexa Fluor® 568-5-dUTP, Alexa Fluor® 594-5-dUTP, Alexa Fluor® 546-14-dUTP, fluorescein-12-UTP, tetramethylrhodamine-6-UTP, Texas Red®-5-UTP, Cascade Blue®-7-UTP, BODIPY® FL-14-UTP, BODIPY® TMR-14-UTP, BODIPY® TR-14-UTP, Rhodamine Green™-5-UTP, Alexa Fluor® 488-5-UTP, Alexa Fluor® 546-14-UTP (Molecular Probes, Inc. Eugene, OR, USA). Other fluorophores available for post-synthetic attachment include, inter alia, Alexa Fluor® 350, Alexa Fluor® 532, Alexa Fluor® 546, Alexa Fluor® 568, Alexa Fluor® 594, Alexa Fluor® 647, BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY 630/650, BODIPY 650/665, Cascade Blue, Cascade Yellow, dansyl, lissamine rhodamine B, Marina Blue, Oregon Green 488, Oregon Green 514, Pacific Blue, rhodamine 6G, rhodamine green, rhodamine red, tetramethylrhodamine, Texas Red (available from Molecular Probes, Inc., Eugene, OR, USA), and Cy2, Cy3.5, Cy5.5, and Cy7 (Amersham Biosciences, Piscataway, N.J. USA, and others). FRET tandem fluorophores may also be used, such as PerCP-Cy5.5, PE-Cy5, PE-Cy5.5, PE-Cy7, PE-Texas Red, and APC-Cy7; also, PE-Alexa dyes (610, 647, 680) and APC-Alexa dyes.

Nucleic acid dyes are fluorescent molecules that are specific for a double-stranded polynucleotide or that at least emits a substantially greater fluorescent signal when associated with a double-stranded polynucleotide than with a single-stranded polynucleotide. Typically, nucleic acid dye molecules associate with double-stranded segments of polynucleotides by intercalating between the base pairs of the double-stranded segment, by binding in the major or minor grooves of the double-stranded segment, or both. Non-limiting examples of nucleic acid dyes include ethidium bromide, DAPI, Hoechst derivatives including without limitation Hoechst 33258 and Hoechst 33342, intercalators comprising a lanthanide chelate (for example but not limited to a napthalene diimide derivative carrying two fluorescent tetradentate 3-diketone-Eu3+ chelates (NDI-(BHHCT-Eu3+)2), see, e.g., Nojima et al., Nucl. Acids Res. Supplement No. 1, 105-06 (2001)), ethidium bromide, and certain unsymmetrical cyanine dyes such as SYBR Green®, PicoGreen® (both available from Molecular Probes-Invitrogen), and BOXTO (TATAA Biocenter AB). In particular embodiments, apparatus 100 is configured to detect the presence, quantitation, or semi-quantitation of an analyte/amplicon/target, etc. of nucleic acids (e.g. deoxyribonucleic acid [DNA], ribonucleic acid [RNA], xeno (synthetic) nucleic acid [XNA]), nuclear material targets, genes of interest (GOI), genomic or somatic mutations. In specific embodiments, apparatus 100 may be disposable (e.g. configured for one-time use). In some embodiments, apparatus 100 may accept cartridges (e.g. including cartridges with different reagent combinations). Apparatus 100 may be battery-powered and portable (e.g. weigh less than 10 pounds, 5 pounds, 1 pound, 400 g, 300 g, 200 g 100 g, 50 g, or less). Apparatus 100 can be configured to accept raw samples and provide analysis or diagnosis of the sample without preparation of the sample prior to the sample being introduced into apparatus 100.

As further described herein, the devices, apparatuses, and methods described herein can be used to detect the presence, absence, or quantity of nucleic acids associated with various biological samples of interest, including, infectious agents such as viruses, bacteria, fungi, protozoa, parasites, as well as host response sequences or patterns of expression associated with infection in humans or other animals. Other non-limiting uses include genomic sequences, somatic mutations, forensics, identification or characterization of genetically-engineered organisms, personalized medicine.

As additionally discussed below, embodiments disclosed herein can be used to detect infectious diseases (including but not limited to HIV, EBV, CMV, influenza, herpes, *Mycoplasma*, pneumonia, cancer, syphilis, fungal and protozoal disease, and hepatitis), diagnosis of cancer, genetic fingerprinting, paternity tests, and forensic analysis. Also provided herein are methods for the identification of non-cultivable or slow-growing microorganisms, such as mycobacteria, anaerobic bacteria, or viruses from tissue culture assays and animal models. Infectious agents of interest also include bacteria pathogens, such as Mycobacteria (e.g., *M. tuberculosis, M bovis, M avium, M leprae*, and *M. africanum*), rickettsia, mycoplasma, chlamydia, and *legionella*. Some examples of bacterial infections include, but are not limited to, infections caused by Gram positive *bacillus* (e.g., *Listeria, Bacillus* such as *Bacillus anthracis*, Erysipelothrix species), Gram negative *bacillus* (e.g., *Bartonella, Brucella, Campylobacter, Enterobacter, Escherichia, Francisella, Hemophilus, Klebsiella, Morganella, Proteus, Providencia, Pseudomonas, Salmonella, Serratia, Shigella, Vibrio* and *Yersinia* species), spirochete bacteria (e.g., *Borrelia* species including *Borrelia burgdorferi* that causes Lyme disease), anaerobic bacteria (e.g., *Actinomyces* and *Clostridium* species), Gram positive and negative coccal bacteria, *Enterococcus* species, *Streptococcus* species, Pneumococcus species, *Staphylococcus* species, and *Neisseria* species. Specific examples of infectious bacteria include, but are not limited to: *Helicobacter pyloris, Legionella pneumophilia, Mycobacterium tuberculosis, Mycobacterium avium, Mycobacterium intracellulare, Mycobacterium kansaii, Mycobacterium gordonae, Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus viridans, Streptococcus faecalis, Streptococcus bovis, Streptococcus pneumoniae, Haemophilus influenzae, Bacillus antracis, Erysipelothrix rhusiopathiae, Clostridium tetani, Enterobacter aerogenes, Klebsiella pneumoniae, Pasteurella multocida, Fusobacterium nucleatum, Streptobacillus moniliformis, Treponema pallidum, Treponema pertenue, Leptospira, Rickettsia*, and *Actinomyces israelii, Acinetobacter, Bacillus, Bordetella, Borrelia, Brucella, Campylobacter, Chlamydia, Chlamydophila, Clostridium, Corynebacterium, Enterococcus, Haemophilus, Helicobacter, Mycobacterium, Mycoplasma, Stenotrophomonas, Treponema, Vibrio, Yersinia, Acinetobacter baumanii, Bordetella pertussis, Brucella abortus, Brucella canis, Brucella*

*melitensis, Brucella suis, Campylobacter jejuni, Chlamydia pneumoniae, Chlamydia trachomatis, Chlamydophila psittaci, Clostridium botulinum, Clostridium difficile, Clostridium perfringens, Corynebacterium diphtherias, Enterobacter sazakii, Enterobacter agglomerans, Enterobacter cloacae, Enterococcus faecalis, Enterococcus faecium, Escherichia coli, Francisella tularensis, Helicobacter pylori, Legionella pneumophila, Leptospira interrogans, Mycobacterium leprae, Mycobacterium tuberculosis, Mycobacterium ulcerans, Mycoplasma pneumoniae, Pseudomonas aeruginosa, Rickettsia rickettsii, Salmonella typhi, Salmonella typhimurium, Salmonella enterica, Shigella sonnei, Staphylococcus epidermidis, Staphylococcus saprophyticus, Stenotrophomonas maltophilia, Vibrio cholerae, Yersinia pestis*, and the like (U.S. Patent Publication No. US20170304829, incorporated herein by reference).

In some embodiments, viral pathogens that may be detected include but are not limited to the herpes virus (e.g., human cytomegalomous virus (HCMV), herpes simplex virus I (HSV-1), herpes simplex virus 2 (HSV-2), varicella zoster virus (VZV), Epstein-Barr virus), influenza A virus and Hepatitis C virus (HCV) or a picornavirus such as Coxsackievirus B3 (CVB3). Other viruses may include, but are not limited to, the hepatitis B virus, HIV, poxvirus, hepadavirus, retrovirus, and RNA viruses such as flavivirus, togavirus, coronavirus, Hepatitis D virus, orthomyxovirus, paramyxovirus, rhabdovirus, bunyavirus, filo virus, Adenovirus, Human herpesvirus, type 8, Human papillomavirus, BK virus, JC virus, Smallpox, Hepatitis B virus, Human bocavirus, Parvovirus B 19, Human astrovirus, Norwalk virus, coxsackievirus, hepatitis A virus, poliovirus, rhinovirus, Severe acute respiratory syndrome virus, Hepatitis C virus, yellow fever virus, dengue virus, West Nile virus, Rubella virus, Hepatitis E virus, and Human immunodeficiency virus (HIV). In some embodiments, the virus is an enveloped virus. Examples of such enveloped viruses include, but are not limited to, viruses that are members of the hepadnavirus family, herpesvirus family, iridovirus family, poxvirus family, flavivirus family, togavirus family, retrovirus family, coronavirus family, filovirus family, rhabdovirus family, bunyavirus family, orthomyxovirus family, paramyxovirus family, and arenavirus family. Other examples include, but are not limited to, Hepadnavirus hepatitis B virus (HBV), woodchuck hepatitis virus, ground squirrel (Hepadnaviridae) hepatitis virus, duck hepatitis B virus, heron hepatitis B virus, Herpesvirus herpes simplex virus (HSV) types 1 and 2, varicella-zoster virus, cytomegalovirus (CMV), human cytomegalovirus (HCMV), mouse cytomegalovirus (MCMV), guinea pig cytomegalovirus (GPCMV), Epstein-Barr virus (EBV), human herpes virus 6 (HHV variants A and B), human herpes virus 7 (HHV-7), human herpes virus 8 (HHV-8), Kaposi's sarcoma—associated herpes virus (KSHV), B virus Poxvirus vaccinia virus, variola virus, smallpox virus, monkeypox virus, cowpox virus, camelpox virus, ectromelia virus, mousepox virus, rabbitpox viruses, raccoon pox viruses, molluscum contagiosum virus, orf virus, milker's nodes virus, bovin papullar stomatitis virus, sheeppox virus, goatpox virus, lumpy skin disease virus, fowlpox virus, canarypox virus, pigeonpox virus, sparrowpox virus, myxoma virus, hare fibroma virus, rabbit fibroma virus, squirrel fibroma viruses, swinepox virus, tanapox virus, Yabapox virus, Flavivirus dengue virus, hepatitis C virus (HCV), GB hepatitis viruses (GBV-A, GBV-B and GBV-C), West Nile virus, yellow fever virus, St. Louis encephalitis virus, Japanese encephalitis virus, Powassan virus, tick-borne encephalitis virus, Kyasanur Forest disease virus, Togavirus, Venezuelan equine encephalitis (VEE) virus, chikungunya virus, Ross River virus, Mayaro virus, Sindbis virus, rubella virus, Retrovirus human immunodeficiency virus (HIV) types 1 and 2, human T cell leukemia virus (HTLV) types 1, 2, and 5, mouse mammary tumor virus (MMTV), Rous sarcoma virus (RSV), lentiviruses, Coronavirus, severe acute respiratory syndrome (SARS) virus, Filovirus Ebola virus, Marburg virus, Metapneumoviruses (MPV) such as human metapneumovirus (HMPV), Rhabdovirus rabies virus, vesicular stomatitis virus, Bunyavirus, Crimean-Congo hemorrhagic fever virus, Rift Valley fever virus, La Crosse virus, Hantaan virus, Orthomyxovirus, influenza virus (types A, B, and C), Paramyxovirus, parainfluenza virus (PIV types 1, 2 and 3), respiratory syncytial virus (types A and B), measles virus, mumps virus, Arenavirus, lymphocytic choriomeningitis virus, Junin virus, Machupo virus, Guanarito virus, Lassa virus, Ampari virus, Flexal virus, Ippy virus, Mobala virus, Mopeia virus, Latino virus, Parana virus, Pichinde virus, Punta torn virus (PTV), Tacaribe virus and Tamiami virus. In some embodiments, the virus is a non-enveloped virus, examples of which include, but are not limited to, viruses that are members of the parvovirus family, circovirus family, polyoma virus family, papillomavirus family, adenovirus family, iridovirus family, reovirus family, birnavirus family, calicivirus family, and picornavirus family. Specific examples include, but are not limited to, canine parvovirus, parvovirus B19, porcine circovirus type 1 and 2, BFDV (Beak and Feather Disease virus, chicken anaemia virus, Polyomavirus, simian virus 40 (SV40), JC virus, BK virus, Budgerigar fledgling disease virus, human papillomavirus, bovine papillomavirus (BPV) type 1, cotton tail rabbit papillomavirus, human adenovirus (HAdV-A, HAdV-B, HAdV-C, HAdV-D, HAdV-E, and HAdV-F), fowl adenovirus A, bovine adenovirus D, frog adenovirus, Reovirus, human orbivirus, human coltivirus, mammalian orthoreovirus, bluetongue virus, rotavirus A, rotaviruses (groups B to G), Colorado tick fever virus, aquareovirus A, cypovirus 1, Fiji disease virus, rice dwarf virus, rice ragged stunt virus, idnoreovirus 1, mycoreovirus 1, Birnavirus, bursal disease virus, pancreatic necrosis virus, Calicivirus, swine vesicular exanthema virus, rabbit hemorrhagic disease virus, Norwalk virus, Sapporo virus, Picornavirus, human polioviruses (1-3), human coxsackieviruses Al-22, 24 (CA1-22 and CA24, CA23 (echovirus 9)), human coxsackieviruses (B1-6 (CB1-6)), human echoviruses 1-7, 9, 11-27, 29-33, vilyuish virus, simian enteroviruses 1-18 (SEVI-18), porcine enteroviruses 1-11 (PEV1-11), bovine enteroviruses 1-2 (BEVI-2), hepatitis A virus, rhinoviruses, hepatoviruses, cardio viruses, aphthoviruses and echoviruses. The virus may be phage. Examples of phages include, but are not limited to T4, T5, λ, phage, T7 phage, G4, P1, φ6, Thermoproteus tenax virus 1, M13, MS2, Qβ, φX174, Φ29, PZA, Φ15, BS32, B103, M2Y (M2), Nf, GA-I, FWLBc1, FWLBc2, FWLLm3, B4. The reference database may comprise sequences for phage that are pathogenic, protective, or both. In some cases, the virus is selected from a member of the Flaviviridae family (e.g., a member of the Flavivirus, Pestivirus, and Hepacivirus genera), which includes the hepatitis C virus, Yellow fever virus; Tick-borne viruses, such as the Gadgets Gully virus, Kadam virus, Kyasanur Forest disease virus, Langat virus, Omsk hemorrhagic fever virus, Powassan virus, Royal Farm virus, Karshi virus, tick-borne encephalitis virus, Neudoerfl virus, Sofjin virus, Louping ill virus and the Negishi virus; seabird tick-borne viruses, such as the Meaban virus, Saumarez Reef virus, and the Tyuleniy virus; mosquito-borne viruses, such as the Arna virus, dengue virus, Kedougou virus, Cacipacore virus, Koutango virus, Japanese encephalitis virus, Murray Valley encephalitis virus, St. Louis encephalitis virus, Usutu virus, West Nile virus, Yaounde virus, Kokobera virus, Bagaza virus, Ilheus virus, Israel turkey meningoencephalo-myelitis virus, Ntaya virus, Tembusu virus, Zika virus, Banzi virus, Bouboui virus, Edge Hill virus, Jugra virus, Saboya virus, Sepik virus, Uganda S virus, Wesselsbron virus, yellow fever virus; and viruses with no known arthropod vector, such as the Entebbe bat virus, Yokose virus, Apoi virus, Cowbone Ridge virus, Jutiapa virus, Modoc virus, Sal Vieja virus, San Perlita virus, Bukalasa bat virus, Carey Island virus, Dakar bat virus, Montana *myotis* leukoencephalitis virus, Phnom Penh bat virus, Rio Bravo virus, Tamana bat virus, and the Cell fusing agent virus. In some cases, the virus is selected from a member of the Arenaviridae family, which includes the Ippy virus, Lassa virus (e.g., the Josiah, LP, or GA391 strain), lymphocytic choriomeningitis virus (LCMV), Mobala virus, Mopeia virus, Amapari virus, Flexal virus, Guanarito virus, Junin virus, Latino virus, Machupo virus, Oliveros virus, Parana virus, Pichinde virus, Pirital virus, Sabia virus, Tacaribe virus, Tamiami virus, Whitewater Arroyo virus, Chapare virus, and Lujo virus. In some cases, the virus is selected from a member of the Bunyaviridae family (e.g., a member of the Hantavirus, Nairovirus, Orthobunyavirus, and Phlebovirus genera), which includes the Hantaan virus, Sin Nombre virus, Dugbe virus, Bunyamwera virus, Rift Valley fever virus, La Crosse virus, Punta Toro virus (PTV), California encephalitis virus, and Crimean-Congo hemorrhagic fever (CCHF) virus. In some cases, the virus is selected from a member of the Filoviridae family, which includes the Ebola virus (e.g., the Zaire, Sudan, Ivory Coast, Reston, and Uganda strains) and the Marburg virus (e.g., the Angola, Ci67, Musoke, POPP, Ravn and Lake Victoria strains); a member of the Togaviridae family (e.g., a member of the Alphavirus genus), which includes the Venezuelan equine encephalitis virus (VEE), Eastern equine encephalitis virus (EEE), Western equine encephalitis virus (WEE), Sindbis virus, rubella virus, Semliki Forest virus, Ross River virus, Barmah Forest virus, O'nyong'nyong virus, and the chikungunya virus; a member of the Poxyiridae family (e.g., a member of the Orthopoxvirus genus), which includes the smallpox virus, monkeypox virus, and vaccinia virus; a member of the Herpesviridae family, which includes the herpes simplex virus (HSV; types 1, 2, and 6), human herpes virus (e.g., types 7 and 8), cytomegalovirus (CMV), Epstein-Barr virus (EBV), Varicella-Zoster virus, and Kaposi's sarcoma associated-herpesvirus (KSHV); a member of the Orthomyxoviridae family, which includes the influenza virus (A, B, and C), such as the H5N1 avian influenza virus or H1N1 swine flu; a member of the Coronaviridae family, which includes the severe acute respiratory syndrome (SARS) virus; a member of the Rhabdoviridae family, which includes the rabies virus and vesicular stomatitis virus (VSV); a member of the Paramyxoviridae family, which includes the human respiratory syncytial virus (RSV), Newcastle disease virus, hendravirus, nipahvirus, measles virus, rinderpest virus, canine distemper virus, Sendai virus, human parainfluenza virus (e.g., 1, 2, 3, and 4), rhinovirus, and mumps virus; a member of the Picomaviridae family, which includes the poliovirus, human enterovirus (A, B, C, and D), hepatitis A virus, and the coxsackievirus; a member of the Hepadnaviridae family, which includes the hepatitis B virus; a member of the Papillamoviridae family, which includes the human papilloma virus; a member of the Parvoviridae family, which includes the adeno-associated virus; a member of the Astroviridae family, which includes the astrovirus; a member of the Polyomaviridae family, which includes the JC virus, BK virus, and SV40 virus; a member of the Calciviridae family, which includes the Norwalk virus; a member of the Reoviridae family, which includes the rotavirus; and a member of the Retroviridae family, which includes the human immunodeficiency virus (HIV; e.g., types I and 2), and human T-lymphotropic virus Types I and II (HTLV-1 and HTLV-2, respectively).

In some embodiments, fungi may be detected including but not limited to *Aspergillus, Blastomyces, Coccidioides, Cryptococcus, Histoplasma, Paracoccidioides, Sporothrix*, and at least three genera of Zygomycetes. In some embodiments, parasites that may be detected include *Plasmodium, Leishmania, Babesia, Treponema, Borrelia, Trypanosoma, Toxoplasma gondii, Plasmodium falciparum, P. vivax, P. ovale, P. malariae, Trypanosoma* spp., or *Legionella* spp.

Results Data

FIG. 34 illustrates a comparative amplification of *Streptococcus pyogenes* DNA segment between an exemplary embodiment of the present disclosure (identified as the "Nuclein™ Device") and an alternate device ("Benchtop qPCR", which is an Applied Biosystems® 7500 Real-Time PCR machine).

FIG. 35 is a graph illustrating on-device detection of *Streptococcus pyogenes* DNA segment using TaqMan probe and an exemplary embodiment of the present disclosure. The graph illustrates PCR detection (in relative fluorescence expressed as a percentage) versus PCR cycle number.

Various Applications

Embodiments provided herein can be used in a broad variety of application areas, including, but not limited to the following: health, environmental monitoring, genomics, forensics, and R&D, as well as other applications.

Nucleic Acids

As noted previously, embodiments of the devices, apparatuses, and methods described herein can be used to detect, among other things, any type of nucleic acid. Nucleic acids, which are essential to all known forms of life, are composed of nucleotides that may contain ribose, in which case the polymer is called RNA (ribonucleic acid), or they may contain deoxyribose, in which case the polymer is called DNA (deoxyribonucleic acid), or they may contain other backbones, including synthetic ones such as threose, cyclohexene, glycol, locked, peptides, fluoro-arabino, 1,5-anhydrohexitol or others, and are collectively called XNA (xenonucleic acid). Types of RNA include, but are not limited to, Messenger RNA (mRNA), Transfer RNA (tRNA), rRNA (Ribosomal RNA), Signal recognition particle RNA (SPR RNA), Transfer-messenger RNA (tmRNA), Guide RNA (gRNA), small nuclear RNA (snRNA), small nucleolar RNA (snoRNA), SmY RNA (SmY), small cajal body-specific RNA (scaRNA), ribonuclease P (RNase P), ribonuclease MRP (RNase MRP), Y RNA, telomerase RNA component (TERC), spliced leader RNA (SL RNA), antisense RNA (aRNA, asRNA), cis-natural antisense transcript (cis-NAT), CRISPR RNA crRNA), long noncoding RNA (lncRNA), microRNA (miRNA), piwi-interacting RNA (piRNA), small interfering RNA (siRNA), short hairpin RNA (shRNA), trans-acting siRNA (tasiRNA), repeat associated siRNA (rasi RNA), 7SK, enhancer RNA (eRNA), vault RNA (vRNA), satellite RNA, viroid, retrotransposon, and many others. DNA may be single stranded (ssDNA) or double stranded (dsDNA) and types of DNA include, but are not limited to, mitochondrial DNA and nuclear DNA, which may also be characterized as autosomal DNA, X-DNA, and Y-DNA, as well as other types of DNA, some of which are referenced herein. In some embodiments, the apparatuses and methods described herein can be used to detect other molecular markers of interest, for instance protein, antibodies, carbohydrates, small molecules, lipids, and combinations of these, such as lipoproteins. In some embodiments, the methods used to detect these non-nucleic acid biomarkers are PLA (Proximity Ligation Assay) or IPCR (Immuno-PCR).

Nucleic acid sequences may be naturally occurring, or they may be modified through genetic engineering techniques, which will be well known to the practitioner. Such techniques can include adding or deleting nucleic acids (in some cases, essentially simultaneously, in order to replace nucleic acids) to a targeted sequence, with changes made by a variety of methods, including, but not limited to, random mutagenesis, random targeting techniques (such as microinjection), or via targeted approaches, such as mutagenesis, zinc finger nucleases, transcription activator-like effector nucleases (TALENS) and Cas-related programmable endonucleases such as the Cas9-guideRNA system, which was adapted from CRISPR. Such techniques performed with a medically therapeutic goal are referred to as gene therapy.

Embodiments of the devices, apparatuses, and methods described herein can also be used to detect nucleic acid analogues, which are structurally similar to naturally occurring RNA and DNA. Such analogues, as referenced previously, are commonly referred to as Xeno Nucleic Acids (or XNA), and they are commonly used in medicine and molecular biology research. While nucleic acids contain a phosphate backbone, a pentose sugar (either ribose or deoxyribose) and a nucleobase (including adenine, cytosine, guanine, thymine, and uracil), a nucleic acid analogue may have any of these altered. Specific examples include, but are not limited to, peptide nucleic acids (PNA), Morpholino and locked nucleic acid (LNA) as well as glycol nucleic acid (GNA) and threose nucleic acid (TNA).

Health

For both humans and animals, the devices, apparatuses, and methods described herein can be used to detect the presence, absence, or quantity of nucleic acids associated with various biological samples of interest, including, infectious agents, including those disclosed herein, such as viruses, bacteria, fungi, protozoa, parasites, as well as host response sequences or patterns of gene expression associated with infection in humans or other animals.

In the cases where the devices, apparatuses, and methods described herein are used in relation to animals, such use may include, but is not limited to, use with pets (e.g., cats, dogs, fish, birds, rabbits, hamsters, mice, ferrets, guinea pigs, etc.), livestock (e.g., cattle, chickens, turkeys, lambs, pigs, etc.), animals used in sports (e.g., racehorses, calves, bulls, and steers, etc.), as well as fish produced in aquaculture (e.g., salmon, cod, tuna, herring, tilapia, catfish, etc.), in addition to any other animal.

Further, the embodiments provided herein can be used for detecting nucleic acid sequences associated with infectious diseases (including, but not limited to, EBV, CMV, influenza, *mycoplasma*, syphilis, fungal and protozoal disease, acute flaccid myelitis, anaplasmosis, anthrax, babesiosis, botulism, brucellosis, campylobacteriosis, Carbapenem-resistant Infection, Chancroid, Chikungunya Virus Infection (Chikungunya), *Chlamydia*, Ciguatera (Harmful Algae Blooms (HABs)), *Clostridium Difficile* Infection, *Clostridium Perfringens* (Epsilon Toxin), Coccidioidomycosis fungal infection (Valley fever), Creutzfeldt-Jacob Disease, transmissible spongiform encephalopathy (CJD), Cryptosporidiosis (Crypto), Cyclosporiasis, Dengue, 1,2,3,4 (Dengue Fever), Diphtheria, *E. coli* infection, Shiga toxin-producing (STEC), Eastern Equine Encephalitis (EEE), Ebola Hemorrhagic Fever (Ebola), Ehrlichiosis, Encephalitis, Arboviral or parainfectious, Enterovirus Infection, Non-Polio (Non-Polio Enterovirus), Enterovirus Infection, D68 (EV-D68), Giardiasis (Giardia), Glanders, Gonococcal Infection (Gonorrhea), Granuloma inguinale, *Haemophilus* Influenza disease, Type B (Hib or H-flu), Hantavirus Pulmonary Syndrome (HPS), Hemolytic Uremic Syndrome (HUS), Hepatitis A (Hep A), Hepatitis B (Hep B), Hepatitis C (Hep C), Hepatitis D (Hep D), Hepatitis E (Hep E), Herpes, Herpes Zoster, zoster VZV (Shingles), Histoplasmosis infection (Histoplasmosis), Human Immunodeficiency Virus/AIDS (HIV/AIDS), Human Papillomavirus (HPV), Influenza (Flu), Lead Poisoning, Legionellosis (Legionnaires Disease), Leprosy (Hansens Disease), Leptospirosis, Listeriosis (*Listeria*), Lyme Disease, Lymphogranuloma venereum infection (LGV), Malaria, Measles, Melioidosis, Meningitis, Viral (Meningitis, viral), Meningococcal Disease, Bacterial (Meningitis, bacterial), Middle East Respiratory Syndrome Coronavirus (MERS-CoV), Mumps, Norovirus, Paralytic Shellfish Poisoning (Paralytic Shellfish Poisoning, Ciguatera), Pediculosis (Lice, Head and Body Lice), Pelvic Inflammatory Disease (PID), Pertussis (Whooping Cough), Plague; Bubonic, Septicemic, Pneumonic (Plague), Pneumococcal Disease (Pneumonia), Poliomyelitis (Polio), Powassan, Psittacosis (Parrot Fever), Pthiriasis (Crabs; Pubic Lice Infestation), Pustular Rash diseases (Small pox, monkeypox, cowpox), Q-Fever, Rabies, Ricin Poisoning, Rickettsiosis (Rocky Mountain Spotted Fever), Rubella, Including congenital (German Measles), *Salmonellosis* gastroenteritis (*Salmonella*), Scabies Infestation (Scabies), Scombroid, Septic Shock (Sepsis), Severe Acute Respiratory Syndrome (SARS), Shigellosis gastroenteritis (*Shigella*), Smallpox, Staphyloccal Infection, Methicillin-resistant (MRSA), Staphylococcal Food Poisoning, Enterotoxin-B Poisoning (Staph Food Poisoning), Staphylococcal Infection, Vancomycin Intermediate (VISA), Staphylococcal Infection, Vancomycin Resistant (VRSA), Streptococcal Disease, Group A (invasive) (Strep A (invasive)), Streptococcal Disease, Group B (Strep-B), Streptococcal Toxic-Shock Syndrome, STSS, Toxic Shock (STSS, TSS), Syphilis, Tetanus Infection, *tetani* (Lock Jaw), Trichomoniasis (*Trichomonas* infection), Trichonosis Infection (Trichinosis), Tuberculosis (TB), Tuberculosis (Latent) (LTBI), Tularemia (Rabbit fever), Typhoid Fever, Group D, Typhus, Vaginosis, bacterial (Yeast Infection), Vaping-Associated Lung Injury (e-Cigarette Associated Lung Injury), Varicella (Chickenpox), *Vibrio cholerae* (Cholera), Vibriosis (*Vibrio*), Viral Hemorrhagic Fever (Ebola, Lassa, Marburg), West Nile Virus, Yellow Fever, Yersenia (*Yersinia*), Zika Virus Infection, or any other infectious disease. Embodiments provided herein can also be used for the detection of nucleic acids associated with infectious agents such as bacteria, including, but not limited to Pneumococcus, *Staphylococcus, Bacillus, Streptococcus*, Meningococcus, Gonococcus, *Escherichia, Klebsiella, Proteus, Pseudomonas, Salmonella, Shigella, Hemophilus, Yersinia, Listeria, Corynebacterium, Vibrio*, Clostridia, *Chlamydia trachomatis, Mycobacterium, Helicobacter* and *Treponema*; protozoan pathogens, and the like. Embodiments provided herein can also be used for the diagnosis of cancer and other illnesses. In the case of cancer, as described previously, this may be achieved either through the detection of circulating tumor DNA (ctDNA) that contains genetic changes useful for detecting cancer. Cancer and other diseases may also be detected by identifying host response sequences or patterns of gene expression associated with diseases.

The embodiments provided herein may also be used for the detection of cell free DNA (cfDNA), which circulates freely in blood. The cfDNA may be cell-free fetal DNA, such as for the detection of genetic defects. The cfDNA may be circulating tumor DNA (ctDNA) that contains genetic changes useful for detecting cancer. The ctDNA may be used for diagnosis, prognosis, monitoring therapy, and estimating tumor volume in a subject (Fiala and Diamandis, BMC Medicine volume 17, Article number: 159 (2019). The cfDNA may be analyzed from a sample of blood. In some embodiments, the process also involves removing serum proteins from the plasma fraction prior to preparing a sequencing library from the cell-free DNA. In some embodiments, removing serum proteins from the plasma fraction involves passing the plasma fraction over a support matrix which adsorbs the serum proteins (U.S. Pat. No. 10,017, 807). In other embodiments, the cfDNA may be analyzed directly without preparing a sequencing library, for example by screening for short sequences of high fragmented, low-molecular weight cfDNA (for example, less than 50 bp, 75 bp, 100 bp, 125 bp, 150 bp, 175 bp, or 200 bp) and detecting sequence differences by use of differential primers in conjunction with a common primer to distinguish SNPs (for example see Woods-Bouwens, et. al., Single-Color Digital PCR Provides High-Performance Detection of Cancer Mutations from Circulating DNA., *Journal of Mol. Diagnostics.*, Vol. 19, No. 5., September 2017, incorporated herein by reference).

Embodiments of the devices, apparatuses, and methods described herein can determine blood type through methods that will be known the practitioner. In some embodiments, ABO blood typing may be performed by using multiplex allele-specific primer sets for the detection of three single-nucleotide polymorphism (SNP) sites (nucleotides 261, 526, and 803) which identify A, B, O01/O02, O03, and cis-AB01 alleles or other SNP sites for the detection of rare A or B subgroups (Lee et al., Rapid Direct PCR for ABO Blood Typing, Journal of Forensic Sciences, 56(s1): S179-S182, 2011; Chen et al., Rapid rare ABO blood typing using a single PCR based on a multiplex SNaPshot reaction, 118(1): 395-400, 2019). Such determination is often critically time-sensitive, and accuracy is paramount. Providing for such determination at a low-cost is also an important consideration in allowing for such determinations to be made on a widespread basis.

Further, embodiments of the devices, apparatuses, and methods described herein can be used on a preventative basis by any patient, doctor, or organization, including, but not limited to, health insurance companies, businesses, and governmental organizations (particularly those which have a need for a high-level of personnel availability, including, but not limited to the military, security forces, law enforcement, peace officers, air traffic controllers, and other essential personnel) that have a desire to proactively monitor to determine if individuals are knowingly or unknowingly infected with a particular pathogen, at increased risk of being infected with a particular pathogen (e.g. by virtue of acquired, innate, or other types of immunodeficiencies), or at risk of becoming ill with a particular disease (for example, due to synergistic coinfection, genetic or epigenetic predisposition, or other factors).

In addition, embodiments of the devices, apparatuses, and methods described herein can be used to rapidly determine the efficacy of gene therapy (e.g. by testing individual tissues, organs, organ systems, or individuals for the presence, absence, or degree of genetic transformation at various points in time, or indirectly by measuring markers related to immune response). Such rapid determination is important to allow rapid adjustments in treatment protocol.

Also, embodiments of the devices, apparatuses, and methods described herein can be used to rapidly determine if someone has suffered a concussion by detecting increased gene expression of various blood-based biomarkers. In some embodiments, the blood-based biomarkers include but are not limited to S1000β for astroglial injury, glial fibrillary acid protein (GFAP) for mild traumatic brain injury, neuron specific enolase (NSE) for neuronal injury, ubiquitin C-terminal hydrolase (UCH-L1) for mild traumatic brain injury, alpha-II spectrin breakdown products for axonal injury, Tau protein for axonal injury, and neurofilaments for axonal injury (Papa, Potential Blood-Based Biomarkers for Concussion, Sports Med Arthrosc, 24(3): 108-115, 2016).

Embodiments of the devices, apparatuses, and methods described herein further provide for a significant number of additional uses related to human and animal health, as will be apparent to the practitioner.

Integration of Other Data

Embodiments of the devices, apparatuses, and methods described herein can be utilized in combination with software applications to proactively monitor for increased risk of infection, as well as, if desired, proactively advise a potential user to use an embodiment of the devices, apparatuses, and methods described herein to test for the presence of one or more infection(s).

Such above-described monitoring may be performed by considering a variety of factors that may be collected either directly by embodiments of the devices, apparatuses, and methods described herein, or by communications between these and other devices, such as wearable technology (e.g., Fitbit®, Oura Ring©, etc.) and audio monitoring technology (e.g., smart phones, Amazon Alexa®, etc.). Such factors may include, but are not limited to, the following: current immune system function (e.g. either directly measured or imputed via physiologic signs, or a combination thereof), time of year, travel history, known or suspected exposures, current and historical epidemiological patterns, particularly including local patterns, or alternatively, patterns among friends and family, with whom someone has had recent direct or indirect contact. Such information may also be obtained through direct input or by indirect methods, such as designing algorithms to analyze social media, email content, travel history, and electronic calendar content.

Additional information that may be considered includes, but is not limited to, any medically relevant biometric data, such as heartrate, heartrate variability, saturation of oxygen levels in the bloodstream, temperature, blood pressure, respiration rate, galvanic skin response, pulse oximetry, voice modulation (particularly differences from known baselines), or other audible data, which may include coughing, sneezing, wheezing, rales, pulmonary crackles, upper airway sounds such as stridor, apnea periods, gastrointestinal disturbances, verbal discussion of symptoms, and overall activity level (particularly differences from baseline), such as changes in total activity or gait whether measured (e.g. by actigraphy) or reported.

Upon analysis of factors including, but not limited to those above, in such a case where it is deemed that the risk of infection or disease (for example, as measured by negative predictive value or positive predictive value) has exceeded a certain threshold, such as 50%, 55%, 60%, 65%, 70%, 75%, 80%, 85%, or 90%, or more preferably, 91%, 92%, 93%, 94%, 95%, 96%, 97%, 98%, 99%, 99.5%, or higher, a particular embodiment of the devices or apparatuses described herein may be automatically ordered by execution of specific algorithm that would be designed using methods that are well known to the practitioner. Such orders may fulfilled by mail or they may be expedited by rapid delivery models, including, but not limited to, courier or drone delivery, as may be offered by any number of expedited retail services (e.g., Prime Now™) in cases where faster delivery is desirable.

Furthermore, in such a case where an embodiment of the devices or apparatuses described herein were used in advance of consideration of the above described data, such data could be used retrospectively to further increase the accuracy of the results. For example, if a test were to conclude that a sample were positive for a rare disease, such as cholera or Ebola, but the sample were contributed from a source which had no apparent exposure route to such rare disease, and otherwise was free from any sign of stress or illness (e.g., biometric data were not indicative of acute pathology), this would increase the likelihood that the test results were erroneous. Alternatively, if the test results were somewhat uncertain (e.g., 50%, 55%, 60%, 65%, 70%, 75%, 80%, 85%, 90%, 91%, 92%, 93%, 94%, 95%, 96%, 97%, 98%, 99%, 99.5%, or higher), and biometric data were indicative of infection, this would increase the likelihood that an infection was in fact present, and such information could be incorporated into the algorithm which determines the test results. In other embodiments, such data may be used to adjust the pretest probability and positive and negative predicative values of a test.

Genomics

In addition to that which is noted above, embodiments of the devices, apparatuses, and methods described herein can be used in the area of genomics. For example, uses may include determining a person's ancestry or an animal's breed (both for live animals and for meat from deceased animals) through methods that will be well understood by the practitioner. In some embodiments, uses may include differentiation of meat of deer from meat of cattle, goats, buffalo, dog, and sheep as well as to differentiate rotten meat (Rajapaksha et al., J Vet Med B Infect Dis Vet Public Health, 49(7): 322-4, 2002, incorporated herein by reference). In some embodiments, uses include differentiation of breeds of dogs (Ezer et al., 87(6):450-5, 1996, incorporated herein by reference) and breeds of cattle (Yoon et al., Asian-Australas J Anim Sci, 18(10), 2005, incorporated herein by reference). Uses may include detecting patterns of SNPs in mitochondrial SNA to trace maternal ancestry. Similarly, uses may include rapid paternity or maternity tests, or establishing other familial relationships, such as sibling, grandmother, grandfather, cousin, aunt, uncle, nephew, niece, or other kinship relationships. Such testing may be of particular interest in time-sensitive situations where familial relation is in doubt, such as situations including immigration or other law enforcement circumstances. There are predictable inheritance patterns at certain locations (called loci) in the human genome, which have been found to be useful in determining identity and biological relationships. These loci contain short tandem repeats (STRs) and the combination of marker sizes found in each person makes up his/her unique genetic profile. Analysis may include Y-chromosome analysis or mitochondrial analysis. Methods to perform such testing with embodiments of the devices, apparatuses, and methods described herein will be well understood by the practitioner.

Further, uses of embodiments of the devices, apparatuses, and methods described herein include identifying the presence, absence, or quantity of particular biologically or medically relevant, non-infectious nucleic acid sequences. These may include, but are not limited to, genes and gene mutations of particular interest. As an example, tests may be used to determine if a person or animal, or other organism, is a genetic carrier (or hereditary carrier), meaning that they have inherited a recessive allele for a genetic trait or mutation, while displaying little or no trait or symptom of the disease (or, in some embodiments cases of epigenetic change or partial or incomplete dominance or imprinting). Such carriers may be autosomal dominant-recessive carriers or gonosomal inheritance carriers or express intermediate, incomplete, partial, or other forms of genetic dominance including imprinting or epigenetic modulation, and varying degrees of phenotypic penetrance. Examples of inherited recessive alleles for genetic disorders include, but are not limited to, those for Down Syndrome, Sickle cell anemia, Cystic fibrosis, Hemophilia, Marfan syndrome, Duchenne muscular dystrophy, spinal muscular dystrophy, Tay-Sachs disease, Fragile X syndrome, GJB2-related hearing loss, Medium-chain acyl-CoA dehydrogenase deficiency, Canavan disease, Familial Dysautonomia, Bloom syndrome, Fanconi Anemia group C, Gaucher disease, Mucolipidosis type IV, Niemann-Pick disease type A, Glycogen Storage 1a, and Maple syrup urine disease (MSUD), including Classic Severe MSUD, Intermediate MSUD, Intermittent MSUD, Thiamine-responsive MSUD and E3-Deficient MSUD with Lactic Acidosis as well as many rare diseases such as those cataloged by Orphanet (updated and available at https://www.orpha.net/consor/cgi-bin/Disease.php, incorporated by reference herein).

Other examples of biologically or medically relevant nucleic acid sequences that the devices, apparatuses, and methods described herein can be used to detect can support personalized medicine, for example, to identify genes related to medication response, (including, but not limited to, Ibuprofen metabolism, Omeprazole metabolism, Pseudocholinesterase deficiency, and Malignant hyperthermia).

Additional examples of biologically or medically relevant nucleic acid sequences that the devices, apparatuses, and methods described herein can be used to identify include those related to various health traits, including genes that relate to commonly occurring genetic sequences and rare mutations. Examples of specific traits may include, but are not limited to, alcohol flush reaction, atopic dermatitis, lactase persistence, prosopagnosia, sleep-related genes (particularly those, such as the ADRB1 and DEC2 genes, which allow individuals to sleep significantly less than approximately eight hours per night, such as four to six hours, yet still feel rested) the RPE65 gene, as well as other traits that will be known the practitioner. Additional examples include genes that relate to diseases, such as those "Variants to Report" listed on the Table at the end of the American College of Medical Genetics and Genomics publication, which is incorporated herein by reference, of "ACMG Recommendations for Reporting of Incidental Findings in Clinical Exome and Genome Sequencing", non-limiting examples of which include the following: BRCA1, BRCA2, TP53, STK11, MLH1, MSH2, MSH6, PMS2, APC, MUTYH, VHL, MEN1, RET, NTRK1, PTEN, RB1, SDHD, SDHAF2, SDHC, SDHB, TSC1, TSC2, WT1, NF2, COL3A1, FBN1, TGFBR2, SMAD3, ACTA2, MYLK, MYH11, MYBPC3, MYH7, TNNT2, TNNI3, TPM1, MYL3, ACTC1, PRKAG2, GLA, MYL2, LMNA, RYR2, PKP2, DSP, DSC2, TMEM43, DSG2, KCNQ1, KCNH2, SCN5A, LDLR, APOB, PCSK9, RYR1, CACNA1S, etc.

Forensics

The devices, apparatuses, and methods described herein may also be used in the area of forensics, which relate to the detection or investigation of crime. Specific non-limiting examples associated with forensic analysis include use to identify the remains of a deceased person or animal through methods of genetic profiling or genetic fingerprinting that will be known to the practitioner, determination of time of death by examining changes in gene expression that occurs post-mortem, as well as determining if a particular suspect or crime victim (e.g., murder victim or kidnapping victim, etc.) had been present at a particular location. Such determinations will be facilitated in cases where a known sample of the individual in question has been previously collected and profiled using methods that will be known to the practitioner, in which case a genetic matching process can be undertaken.

Environmental

The devices, apparatuses, and methods described herein may also be used to detect nucleic acid sequences that exist in environmental samples. Environmental sources from which samples may be collected may include seawater or freshwater (non-limiting examples include lakes, rivers, ponds, streams, and rainwater), terrestrial soil, aquatic soil or sediment, snow, permafrost, or air.

Examples of environmentally-related uses include detecting the presence, absence, or quantity of nucleic acid sequences of interest (such as from environmental DNA or "eDNA") which may be associated with particular organisms of interest. Example sources may include, but are not limited to, feces, mucus, gametes, shed skin, caresses, and hair, as well as other sources described herein, and they can be analyzed through methods that will be known to the practitioner. Such analysis supports biomonitoring, without the collection of a living or deceased organism, and may be used to detect invasive, elusive, or endangered species, in addition to commonly found species. Such information can be particularly useful when studying population size, species distribution, and general population dynamics.

The devices, apparatuses, and methods described herein also be used to determine the presence or absence of infectious agents such as parasites, bacteria, and viruses, many of which have specifically been previously referenced herein, by testing environmental sources for associated DNA (using methods that will be known to the practitioner). In this way, potential infectious agents can be identified and avoided before transmission has taken place. As a non-limiting example, waterborne diseases are a significant health problem, particularly in developing countries. Examples of water borne diseases can include, but are not limited to, the following: typhoid fever, cholera, giardia, dysentery, *Escherichia coli* (*E. coli*), *Salmonella*, and Hepatitis A. By using the devices, apparatuses, and methods described herein, water can be tested before use to ensure that it is free from an infectious agent, that an infectious agent is present, or in some embodiments, that the sample is above or below the minimum infective dose (MID).

Similar to that which is described above, the devices, apparatuses, and methods described herein can be used in ways that will be known the practitioner to test for the presence or absence of nucleic acid sequences associated with infectious agents in and around homes, particularly including, but not limited to, testing residential well water and pools, as well as testing mold, spore, and fungal samples to determine potential toxicity.

Further environmental analysis can be conducted the devices, apparatuses, and methods described herein can be used in ways that will be known the practitioner by municipalities or other governmental organizations to test for the presence or absence of nucleic acid sequences associated with vector-borne diseases carried by mosquitoes (non-limiting examples include chikungunya, dengue fever, lymphatic filariasis, Rift Valley fever, yellow fever, Zika, malaria, Japanese encephalitis, and West Nile fever), sandflies (non-limiting examples Leishmaniasis and Sandfly fever), ticks (non-limiting examples include Crimean-Congo hemorrhagic fever, Lyme disease, relapsing fever [borreliosis], Rickettsial diseases [spotted fever and Q fever], Tick-borne encephalitis and tularemia), Triatomine bugs (a non-limiting example includes Chagas disease [American trypanosomiasis]), tsetse flies (a non-limiting example includes sleeping sickness [African trypanosomiasis]), fleas (non-limiting examples include plague and rickettsiosis), Black flies (a non-limiting example includes onchocerciasis [river blindness]), aquatic snails (a non-limiting example includes schistosomiasis [bilharziasis]), and lice (non-limiting examples include typhus and louse-borne relapsing fever). Additional environmental analysis which can be conducted the devices, apparatuses, and methods described herein by municipalities or other governmental organizations is the localization of infrastructure leaks. Such detection can be accomplished by detecting nucleic acid sequences of organisms associated with such infrastructure leaks using a process that iteratively quantifies the density of such organisms to locate the leak (e.g., the higher the density of associated organisms, the closer the leak).

Beyond the examples noted above, the devices, apparatuses, and methods described herein can be used in ways that will be understood by the practitioner to determine whether a food source, whether plant or animal, has been genetically engineered.

Moreover, the devices, apparatuses, and methods described herein can be used in ways that will be known the practitioner to determine whether a food-borne pathogen exists, either in food itself, or in the areas where the food is being prepared, such as a residential or commercial kitchen or other food preparation location.

Additional Embodiments

Unlike other commonly utilized nucleic acid testing methodologies, the devices, apparatuses, and methods described herein offer the opportunity for individuals to perform tests and receive results in private, with no involvement of third parties necessary. Further, in some embodiments, the test can be performed, and results received, without any data communication with an outside location, server, data repository, or like device. This offers superior levels of privacy and security with regard to health records relative to other common options. In part, this is because the devices, apparatuses, and methods described herein can work in some embodiments on a portable basis, allowing tests to be performed on a stand-alone basis, with no data connectivity or other equipment necessary. It is also due to the devices, apparatuses, and methods described herein requiring no specific technical skills or specialized training to undertake, such that the general public may be able to operate them without third-party assistance.

It is also possible for the devices, apparatuses, and methods described herein to operate in a way such that the included software and hardware can internally validate themselves. For example, in some embodiments, the software may include reference values for variance or operating parameters against which the data may be compared. In other embodiments, the magnitude or character the data (e.g. stochastic or discontinuous change of data) may be used to identify data which is not in concert with plausibly valid data.

Additionally, where desired, the devices, apparatuses, and methods described herein may be used in conjunction with digital communication technologies that will be known the practitioner that can, where an appropriately trained medical professional is not immediately available in person, allow for virtual inclusion of a physician (MD), Physician's Assistant (PA), Advanced Practice Registered Nurse (APRN), Registered Nurse, or other medical appropriately trained medical professional. In various embodiments, such digital communication technologies include wired communication technologies (e.g., Universal Serial Bus, Ethernet) and/or wireless communications technologies. In various embodiments, such wireless communications technologies include any suitable wireless communication protocol network, such as a wireless telephony network (e.g., GSM, CDMA, LTE, etc.), a Wi-Fi network (IEEE 802.11 standards), a WiMAX network, a Bluetooth network, etc. Additionally, or alternatively, such wireless communications technologies include circuitry operable to communicate using a near field communication standard (e.g., ISO/IEC 18092, standards provided by the NFC Forum, etc.). Such inclusion can allow for the immediate review of test results and, where appropriate, provision of a prescription. Particular algorithms that will be known the practitioner can provide for dosage guidelines, and they can take into account the patient's medical condition, using both biometric data described herein, as well as the patient's allergies, other medications, and overall medical condition, as well as considerations relating to the particular geographic area where the patient is then or will soon be located.

In various embodiments of devices, apparatuses, and methods described herein, personal information that uniquely identifies or can be used to identify a specific person may be stored. Such personal information includes but is not limited to names, addresses, demographic data, location-based data, physical addresses, electronic addresses, data or records relating to a user's health or level of fitness (e.g., vital signs measurements, medication information, exercise information), date of birth, etc. The collection, analysis, disclosure, transfer, storage, or other use of such personal information data will comply with well-established privacy policies and/or privacy practices in various embodiments (e.g., encrypted storage, hashing, etc.). In various instances, policies and practices should be adapted for the particular types of personal information data being collected and/or accessed and adapted to applicable laws and standards, including jurisdiction-specific considerations that may serve to impose a higher standard. For instance, in the US, collection of or access to certain health data may be governed by federal and/or state laws, such as the Health Insurance Portability and Accountability Act (HIPAA); whereas health data in other countries may be subject to other regulations and policies and should be handled accordingly.

Further, embodiments of the devices, apparatuses, and methods described herein, by testing for nucleic acid sequences matching certain companion biomarkers can function as companion diagnostic tests, which can be used as a companion to a therapeutic drug to determine its applicability to a specific person. Non-limiting examples are biomarkers for cancer mutations (e.g. BCR-ABL translocations), hypersensitivity or unsuitability to certain medications or therapies (e.g. malignant hyperthermia), intersections of disease-states with potential modalities (e.g. testing for heartworm in anticipation of therapy), mutations in the PIK3CA gene, as well as biomarkers listed for those diseases listed on the "FDA List of Cleared or Approved Companion Diagnostic Devices (In Vitro and Imaging Tools)" which is incorporated herein by reference, e.g. acute myelogenous leukemia, aggressive systemic mastocytosis, B-cell chronic lymphocytic leukemia, breast cancer, cervical cancer, chronic myeloid leukemia, colorectal cancer, esophageal squamous cell carcinoma, gastric and gastroesophageal cancer, gastroesophageal junction adenocarcinoma, gastrointestinal stromal tumors, head and neck squamous cell carcinoma, melanoma, myelodysplastic syndrome/myeloproliferative disease, non-small cell lung cancer, non-transfusion-dependent thalassemia, ovarian cancer, triple-negative breast carcinoma (TNBC), or urothelial carcinoma, etc.

Last, in conjunction with embodiments of the devices, apparatuses, and methods described herein, algorithms that will be known the practitioner can be employed to develop an epidemiological forecasts and patterns that may be valuable in proactive preparation for disease containment.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All examples disclosed herein are non-limiting examples. All such similar substitutes and modifications apparent to those skilled in the art are deemed to be within the spirit, scope and concept of the invention as defined by the appended claims.

V. REFERENCES

The following references, to the extent that they provide exemplary procedural or other details supplementary to those set forth herein, are specifically incorporated herein by reference.

U.S. Pat. No. 6,132,996
U.S. Pat. No. 6,453,242
U.S. Pat. No. 6,503,717
U.S. Pat. No. 6,534,261
U.S. Pat. No. 6,599,692
U.S. Pat. No. 6,689,558
U.S. Pat. No. 6,794,136
U.S. Pat. No. 7,030,215
U.S. Pat. No. 7,067,317
U.S. Pat. No. 7,070,934
U.S. Pat. No. 7,253,273
U.S. Pat. No. 7,262,054
U.S. Pat. No. 7,361,635
U.S. Pat. No. 7,524,652
U.S. Pat. No. 7,888,015
U.S. Pat. No. 8,398,940
U.S. Pat. No. 8,640,555
U.S. Pat. No. 8,720,198
U.S. Pat. No. 9,044,755

U.S. Pat. No. 9,105,384
U.S. Pat. No. 9,427,739
U.S. Pat. No. 9,476,895
U.S. Pat. No. 9,519,000
U.S. Pat. No. 9,623,415
U.S. Pat. No. 9,932,634
U.S. Pat. No. 10,011,841
U.S. Pat. No. 10,017,807
U.S. Pat. No. 10,040,071
U.S. Pat. No. 10,112,196
U.S. Pat. No. 10,196,678
U.S. Pat. No. 8,795,965
U.S. Pat. No. 8,211,202
U.S. Patent App. No. 20100291536
U.S. Patent App. No. 20110059502
U.S. Patent Pub. No. 20180193834
U.S. Patent Pub. No. 20020068357
U.S. Patent Pub. No. 20040014117
U.S. Patent Pub. No. 20050013732
U.S. Patent Pub. No. 20050064474
U.S. Patent Pub. No. 20050267061
U.S. Patent Pub. No. 20060188987
U.S. Patent Pub. No. 20070218528
U.S. Patent Pub. No. 20100137152
U.S. Patent Pub. No. 20110312072
U.S. Patent Pub. No. 20110318728
U.S. Patent Pub. No. 20150079598
U.S. Patent Pub. No. 20150136602
U.S. Patent Pub. No. 20150273472
U.S. Patent Pub. No. 20160263579
U.S. Patent Pub. No. 20170074258
U.S. Patent Pub. No. 20170173588
U.S. Patent Pub. No. 20170247745
U.S. Patent Pub. No. 20170304829
U.S. Patent Pub. No. 20180154364
AU2015210344
CN107653300
WO2014113663
WO2018005870
Antoon L. et. al., *Nucleic Acids Research*, Vol. 40, No. 2 e10. 2012.
Applied Biosystems™ by *Thermo Fischer Scientific*™ "Getting Started Guide," 2015.
Barany F, Proc. *Natl. Acad. Sci.* 88:189-193, 1991.
Bengtsson et al., *Nucleic Acids Res* 31:e45, 2003.
Chia et al.; *Journal of Mechanics*, Vol. 27, Issue 03, pp. 357-364, September 2011.
Choi et al.; *Biosensors and Bioelectronics* 115, 83-90, 2018.
Compton, J., *Nature* 350: 91-92, 1991.
Farrar et al.; *Clinical Chemistry*, 61 (1) 145-153, January 2015.
Fire A, Xu S-Q, Proc. *Natl Acad. Sci. USA* 92:4641-4645, 1995.
French et al., Mol Cell Probes 15:363-374, 2001.
Gootenberg et al., *Science*, 356(6336): 438-442, 2017.
H. J. Karlsson et al., *Bioorganic & Medicinal Chemistry* 11:1035-1040, 2003.
Haugland, Handbook of Fluorescent Probes and Research Chemicals, 6th ed. 1996.
Higuchi et al., *Biotechnology* 10:413-417, 1992.
Holland et al., Proc Natl Acad Sci USA 88:7276-7280, 1991.
Hoser M J, Mansukoski H K, Morrical S W, Eboigbodin K E, *PLOS ONE* 9:e112656, 2014.
http://tools.thermofisher.com/content/sfs/manuals/cms_041902.pdf
https://www.idtdna.com/pages/education/decoded/article/designing-per-primers-and-probes
https://www.idtdna.com/pages/products/custom-dna-rna/oligo-modifications/fluorophores/freedom-dyes
https://www.ncbi.nlm.nih.gov/probe/docs/projtaqman/
Ishiguro et al., *Anal Biochem* 229:207-213, 1995.
Jones, M. E., et al., *Computational Biology Journal*, Article ID 601504, 2015.
Kandimalla and Agrawal, *Bioorg Med Chem* 8:1911-1916, 2000.
Kaur et al., *Biochemistry* 45:7347-7355, 2006.
Kaur H, Arora A, Wengel J, Maiti S., *Biochemistry* 45:7347-7355, 2006.
Kutyavin *Nucleic Acids Res* 38:e29, 2010.
Kutyavin, *Nucleic Acids Res.* 41: e191, 2013.
Lee et al., *Anal Chim Acta;* 457:61-70, 2002.
Legendre et al.; *Anal Chem.;* 78(5):1444-51, 2006.
Li et al., *Nucleic Acids Res* 30:e5, 2002.
Liew, *Clin Chem* 50:1156-1164, 2004.
Liu et al.; *Anal. Chem.*, 76, 1824-1831, 2004.
Monis et al., *Anal Biochem* 340:24-34, 2005.
Morrison et al., *Anal Biochem* 183:231-244, 1989.
Myhrvoid et al., *Science,* 360(6387), 444-448, 2018.
Nazarenko et al., *Nucleic Acids Res* 25:2516-2521, 1997.
Nazarenko et al., *Nucleic Acids Res* 30:e37, 2002.
Nazarenko I A, Bhatnagar S K, Hohman R J, *Nucleic Acids Res* 25:2516-2521, 1997.
Nielsen et al., *Science* 254:1497-1500, 1991.
Niemz et al.; *Trends Biotechnol.,* 29(5): 240-250, 2011.
Notomi T, et al., *Nucleic Acids Res.* 28:e63, 2000.
Pals et al., *J Biochem Biophys Methods,* 47:121-129, 2001.
Piepenburg O, Williams C H, Stemple D L, Armes N A, *PLoS Biology* 4: e204, 2006.
Pons et al., *Chembiochem* 7:1173-1176, 2006.
Prediger, *Integrated Data Technologies,* 2015.
Prediger, *Integrated Data Technologies,* 2018.
Prediger, *Integrated DNA Technologies,* 2013.
Richard P. Haugland, *Handbook of Fluorescent Probes and Research Chemicals* (6th ed. 1996).
Schneeberger et al., *PCR Methods Appl* 4:234-238, 1995.
Sherrill et al., *J Am Chem Soc,* 126:4550-4556, 2004
Tuma et al., *Anal Biochem.,* 268:278-288, 1999.
Tyagi and Kramer, *Nat Biotechnol* 14: 303-8, 1996.
Vincent M, Xu Y, Kong H, *EMBO Rep* 5:795-800, 2004.
Walker G T, Fraiser M S, Schram J L, Little M C, Nadeau J G, Malinowski D P, *Nucleic Acids Res* 20:1691-1696, 1992.
Wang et al., *Anal Biochem* 356:303-305, 2006.
Whitcombe et al., *Nat Biotechnol* 17: 804-807, 1999.
Zanoli and Spoto, *Biosensors* 3(1): 18-43, 2013.
Zhang, et al.; *Sensors and Actuators B*: Chemical, 126924, 2019.
Zhao, S. and Fernald, R. D., *J Comput. Biol.,* 12(8): 1047-1064, 2005.
Lorenz, TC, J Vis Exp., (63):e3998, 2012.
Roux, Cold Spring Harb Protoc., 2009
Robertson and Walsh-Weller, Methods Mol Biol., 98:121-54, 1998.
Zainabadi et al., PLoS One, 14(2): e0210813; 2019.
Kulinski et al., Biomed Microdevices, 11(3): 671-678, 2009.
Darbandi et al., Middle East Fertitility Society Journal, 23(3): 216-219, 2018.
Wu et al., Biotechniques, 58(6): 293-300, 2014.
Sildorova et al., Experimental Dermatology, 2011
Kajivara et al., J Biomol Tech, 26(4):118-124, 2015
Rutledge, R. G., Nucleic Acids Research, Vol. 32, No. 22, 2004.
Liu, W. and Saint, D. A., Biochem. Biophys. Res. Commun., 294,347-353, 2009.

NIST/SEMATECH e-Handbook of Statistical Methods, 2013 http://itl.nist.gov/div898/handbook/, incorporated herein by reference
Zhang G., et al., Macromolecules, 51 (5), pp 1927-1936, 2018.
Drouin et al, J. Polaina and A. P. MacCabe (eds.), *Industrial Enzymes*, 379-401, 2007.
Batista and Pacheco, Journal of Microbiological Methods, 152: 98-104, 2018.
Beerli et al. Nature Biotechnol. 20:135-141, 2002.
Pabo et al. Ann. Rev. Biochem. 70:313-340, 2001.
Isalan et al. Nature Biotechnol. 19:656-660, 2001.
Segal et al. Curr. Opin. Biotechnol. 12:632-637, 2001.
Choo et al. Curr. Opin. Struct. Biol. 10:411-416, 2000.
Gaj et al., Trends in Biotechnology 31(7), 397-405, 2013.
Bartlett J M S, Stirling D, Methods in Molecular Biology, 2003.
Kerry, Joseph; Butler, Paul, Wiley & Sons, 2008.
Haff and Smirnov, Nucl. Acids Res. 25:3749-50, 1997.
Xu et al., Anal. Chem. 69:3595-3602; 1997.
Sauer et al., Nucl. Acids Res. 31:e63, 2003.
Gootenberg et al., Science, 356(6336): 438-442, 2017
Myhrvoid et al., Science, 360(6387), 444-448, 2018.
de la Rica, Anal. Chem., 81, 10, 3830-3835, 2009.
Farrar et al., Molecular Diagnostics, 79-102, 2017.
Omar and MatJafri, Sensors, 9(10): 8311-8335, 2009.
Urusov et al., Biosensors, 9(3): 89; 2019.
Toehold Probes for Nucleic Acid Detection, New molecular probe can distinguish DNA and RNA sequences with unprecedented accuracy, Wyss Institute, 2012
Tyagi and Kramer, F1000 Med Rep, 4:10, 2012.
Nojima et al., Nucleic Acids Symposium Series, Volume 1, Issue 1, 105-06, 2001.
Fiala and Diamandis, BMC Medicine, Volume 17, Article number: 159, 2019.
Woods-Bouwens, et. al., Journal of Mol. Diagnostics., Vol. 19, No. 5, 2017.
Lee et al., Journal of Forensic Sciences, 56(s1): S179-S182, 2011.
Chen et al., Journal of the Formosan Medical Assoc, 118(1): 395-400, 2019.
Papa, Sports Med Arthrosc, 24(3): 108-115, 2016.
Rajapaksha et al., J Vet Med B Infect Dis Vet Public Health, 49(7): 322-4, 2002.
Ezer et al., Journal of Heredity, 87(6):450-5, 1996
Yoon et al., Asian-Australas J Anim Sci, 18(10), 2005.

What is claimed:

1. An apparatus for performing molecular diagnostics, the apparatus comprising:
   a housing comprising a first end and a second end;
   a piston disposed within the housing;
   a first heat source proximal to the first end of the housing; and
   an actuator configured to move the piston in a cycle from a first position proximal to the first end of the housing, to a second position proximal to the second end of the housing, and back to the first position proximal to the first end of the housing, wherein: the piston is configured to direct a fluid to the second end of the housing when the piston is in the first position; the piston is configured to direct the fluid to the first end of the housing when the piston is in the second position; and the fluid moves in an opposite direction to the piston during the cycle from the first position proximal to the first end of the housing, to the second position proximal to the second end of the housing, and back to the first position proximal to the first end of the housing.

2. The apparatus of claim 1 wherein:
   the piston has an outer diameter;
   the housing has an inner diameter; and
   the ratio of the outer diameter of the piston to the inner diameter of the housing is between 0.90 and 0.999.

3. The apparatus of claim 1, further comprising a second heat source proximal to the second end of the housing, wherein:
   the first heat source comprises a first heat source configured to increase the temperature of the first end of the housing when electric current is applied to the first heat source; and
   the second heat source comprises a second heat source configured to increase the temperature of the second end of the housing when electric current is applied to the second heat source.

4. The apparatus of claim 1 further comprising a reaction chamber insert configured to be inserted into the housing, wherein the reaction chamber insert contains a reaction fluid during use.

5. The apparatus of claim 1 wherein the housing comprises a fluid configured to amplify a nucleic acid via thermal cycling.

6. The apparatus of claim 1 wherein the fluid comprises polymerase chain reaction (PCR) reagents or reverse transcriptase polymerase chain reaction (RT-PCR) reagents.

7. The apparatus of claim 1 further comprising an illumination module configured to illuminate an analyte contained in the fluid.

8. The apparatus of claim 7 further comprising a detection module configured to detect a response from the analyte contained in the fluid, wherein the detection module detects a response from the analyte in real time during amplification.

9. The apparatus of claim 8 wherein the detection module detects a response from the analyte within an amplification cycle.

10. The apparatus of claim 9, wherein the amplification cycle has a variable length.

11. The apparatus of claim 1 further comprising a controller configured to control the actuator, and the first heat source, wherein the controller is configured to: control the first heat source to heat the fluid proximal to the first end of the housing to a temperature between about 92 and 98 degrees Celsius; control a second heat source to heat the fluid proximal to the second end of the housing to a temperature between about 60 and 65 degrees Celsius; and cycle the piston from the first position to the second position and back to the first position between about 30 and 50 cycles.

12. The apparatus of claim 1 wherein the actuator comprises:
   at least one coil; and
   a magnetic element disposed within the housing, wherein the at least one coil is configured to exert a force on the magnetic element when electric current is applied to the at least one coil.

13. The apparatus of claim 1 wherein the actuator comprises:
   a first coil proximal to the first end of the housing;
   a second coil proximal to the second end of the housing; and
   a first magnetic element disposed within the housing; and
   a second magnetic element disposed within the housing wherein:
     the first coil is configured to exert a first force on the first magnetic element when electric current is applied to the first coil; and the second coil is configured to exert a second force on the second magnetic element when electric current is applied to the second coil.

14. The apparatus of claim 13 wherein:
the first coil is configured to increase the temperature of the first end of the housing when electric current is applied to the first coil; and
the second coil is configured to increase the temperature of the second end of the housing when electric current is applied to the second coil.

15. The apparatus of claim 1 further comprising an input port in fluid communication with the housing.

* * * * *